US010100127B2

(12) United States Patent
Daiss et al.

(10) Patent No.: US 10,100,127 B2
(45) Date of Patent: Oct. 16, 2018

(54) PASSIVE IMMUNIZATION FOR STAPHYLOCOCCUS INFECTIONS

(71) Applicant: UNIVERSITY OF ROCHESTER, Rochester, NY (US)

(72) Inventors: John L. Daiss, Rochester, NY (US); Edward Schwarz, Rochester, NY (US); John J. Varrone, Rochester, NY (US); James Brodell, Jr., Rochester, NY (US); Sheila N. Bello-Irizarry, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 15/104,104

(22) PCT Filed: Dec. 15, 2014

(86) PCT No.: PCT/US2014/070337
§ 371 (c)(1),
(2) Date: Jun. 13, 2016

(87) PCT Pub. No.: WO2015/089502
PCT Pub. Date: Jun. 18, 2015

(65) Prior Publication Data
US 2016/0311925 A1    Oct. 27, 2016

Related U.S. Application Data

(60) Provisional application No. 61/915,953, filed on Dec. 13, 2013.

(51) Int. Cl.
| C07K 16/40 | (2006.01) |
| A61K 39/40 | (2006.01) |
| D21H 27/30 | (2006.01) |
| D21H 27/38 | (2006.01) |
| D21H 11/02 | (2006.01) |
| D21H 11/08 | (2006.01) |
| B32B 29/00 | (2006.01) |
| A61K 45/06 | (2006.01) |
| G01N 33/569 | (2006.01) |
| A61K 39/00 | (2006.01) |

(52) U.S. Cl.
CPC .............. *C07K 16/40* (2013.01); *A61K 39/40* (2013.01); *A61K 45/06* (2013.01); *B32B 29/005* (2013.01); *D21H 11/02* (2013.01); *D21H 11/08* (2013.01); *D21H 27/30* (2013.01); *D21H 27/38* (2013.01); *G01N 33/56938* (2013.01); *A61K 2039/505* (2013.01); *A61K 2039/507* (2013.01); *B32B 2250/26* (2013.01); *B32B 2262/0261* (2013.01); *B32B 2262/062* (2013.01); *B32B 2262/067* (2013.01); *B32B 2307/54* (2013.01); *B32B 2307/72* (2013.01); *B32B 2439/00* (2013.01); *B32B 2439/70* (2013.01); *C07K 2317/14* (2013.01); *C07K 2317/21* (2013.01); *C07K 2317/24* (2013.01)

(58) Field of Classification Search
None
See application file for complete search history.

(56) References Cited

U.S. PATENT DOCUMENTS

| 8,101,190 B2 | 1/2012 | Cyncynatus et al. |
| 8,211,431 B2 | 7/2012 | Throsby et al. |
| 8,426,139 B2 | 4/2013 | Arie |
| 2008/0177045 A1 | 7/2008 | Lee et al. |
| 2011/0092372 A1 | 4/2011 | Almagro et al. |
| 2013/3011029 | 5/2013 | Schwarz et al. |
| 2014/0371428 A1 | 12/2014 | Schwarz et al. |

FOREIGN PATENT DOCUMENTS

| WO | 2006/032472 A2 | 3/2006 |
| WO | 2010/119343 A2 | 10/2010 |
| WO | 2013/066876 A1 | 5/2013 |

OTHER PUBLICATIONS

Vajdos et al. (J Mol Biol. Jul. 5, 2002;320(2):415-28.*
Brown et al. (J Immunol. May 1996;156(9):3285-91.*
Supplementary European Search Report for European Application No. 14870387.9 (dated Jul. 7, 2017).
Bello-Irizarry et al., "Anti-Amidase Monoclonal Antibodies as a Passive Immunization Against Methicillin-Resistant *Staphylococcus aureus* (MRSA) Implant-Associated Osteomyelitis," Abstracts of the General Meeting of the American Society for Microbiology, 114th General Meeting of the American-Society-for-Microbiology, Boston, MA 114:2604 (2014).
Bello-Irizarry et al., "Complete Protection from Methicillin-Resistant *Staphylococcus aureus* (MRSA) Implant-Associated Osteomyelitis in Mice Passively Immunization with Anti-Autolysin Monoclonal Antibodies as Determined by Inhibition of Osteolysis, Biofilm and Staphylococcal Abscess Communities (SAC)," 2016 Orthopaedic Research Society Annual Meeting, Orlando, FL, Poster No. 2095 (Mar. 7-8, 2016) (http://www.ors.org/Transactions/62/2095.pdf).

(Continued)

*Primary Examiner* — Brian Gangle
(74) *Attorney, Agent, or Firm* — LeClairRyan PLLC

(57) ABSTRACT

Disclosed herein are monoclonal antibodies or binding portion thereof that bind specifically to a *Staphylococcus* spp. autolysin N-acetylmuramoyl-L-alanine amidase catalytic domain and/or cell wall binding domain, as well as pharmaceutical compositions containing the same. Cell lines expressing the monoclonal antibodies, including hybridomas, are also disclosed. Methods of using the monoclonal antibodies for installation of orthopedic implants, grafts or medical devices, treating or preventing a *Staphylococcus* infection, and treating osteomyelitis are described, as are diagnostic methods for the detection of *Staphylococcus* in a sample.

41 Claims, 9 Drawing Sheets
Specification includes a Sequence Listing.

(56) References Cited

OTHER PUBLICATIONS

Bose et al., "Contribution of the *Staphylococcus aureus* Atl AM and GL Murein Hydrolase Activities in Cell Divison, Autolysis, and Biofilm Formation," PLoS ONE 7(7):e42244 (2012).

Garcia et al., "Preparation of Antiserum Against the Pneumococcal Autolysin-Inhibition of Autolysin Activity and Some Autolytic Processes by the Antibody," FEMS Microbiology Letters 14:133-136 (1982).

Nelson et al., "Endolysins as Antimicrobials," in "Advances in Virus Research," Academic Press, US, Chapter 7, vol. 83:299-365 (2012).

Oshida et al., "A *Staphylococcus aureus* Autolysin that has an N-acetylmuramoyl-L-alanine Amidase Domain and an Endo-Beta-N-Acetylglucosaminidase Domain: Cloning, Sequence Analysis, and Characterization," Microbiology 92:285-289 (1995).

Sugai et al., "Identification of Endo-Beta-N-Acetylglucosaminidase and N-acetylmuramyl-L-Alanine Amidase as Cluster-Dispersing Enzymes in *Staphylococcus aureus*," Journal of Bacteriology 177(6):1491-1496 (1995).

Sugai et al., "Localized Perforation of the Cell Wall by a Major Autolysin: atl Gene Products and the Onset of Penicillin-Induced Lysis of *Staphylococcus aureus*," Journal of Bacteriology 179(9):2958-2962 (1997).

Yamada et al., "An Autolysin Ring Associated with Cell Separation of *Staphylococcus aureus*," Journal of Bacteriology 178(6):1565-1571 (1996).

Gedbjerg et al., "Anti-glucosaminidase IgG in Sera as a Biomarker of Host Immunity Against *Staphylococcus aureus* in Orthopaedic Surgery Patients," J Bone Joint Surg Am. 95:1-9 (2013).

Kawamura et al., "Distribution of *Staphylococcus* Species among Human Clinical Specimens and Emended Description of *Staphylococcus caprae*," J of Clinical Microbiology 36(7):2038-2042 (1998).

Office Action for counterpart European Application No. 14870387.9 (dated Jun. 4, 2018).

Martin, Andrew C.R., "Protein Sequence and Structure Analysis of Antibody Variable Domains," Antibody Engineering, Chapter 3, vol. 2:33-51 (2010).

* cited by examiner

FIG. 6A IgG control
FIG. 6B Anti-Amd
FIG. 6C Anti-Amd + Anti-Gmd
FIG. 6D Δatl

PBS    Anti-Amd    Anti-Gmd    1.6 + 1C11

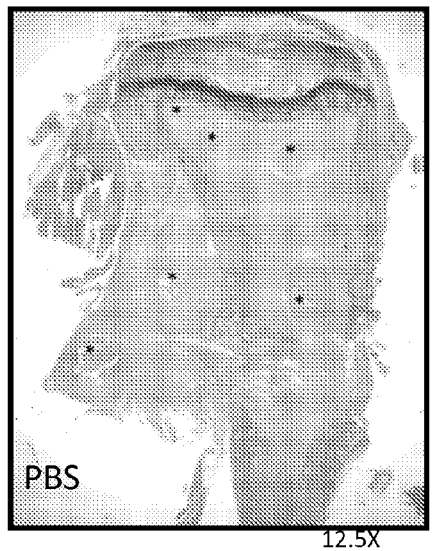
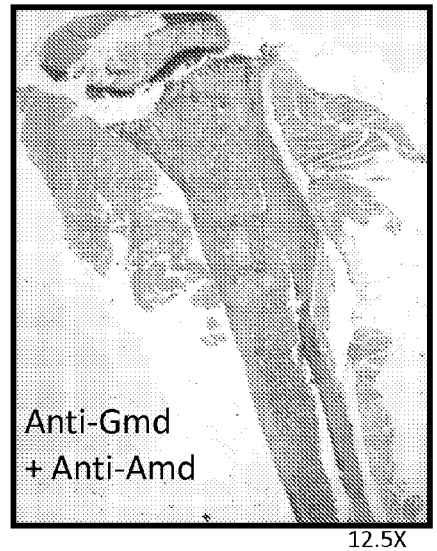
* abscess
FIG. 8A
FIG. 8B
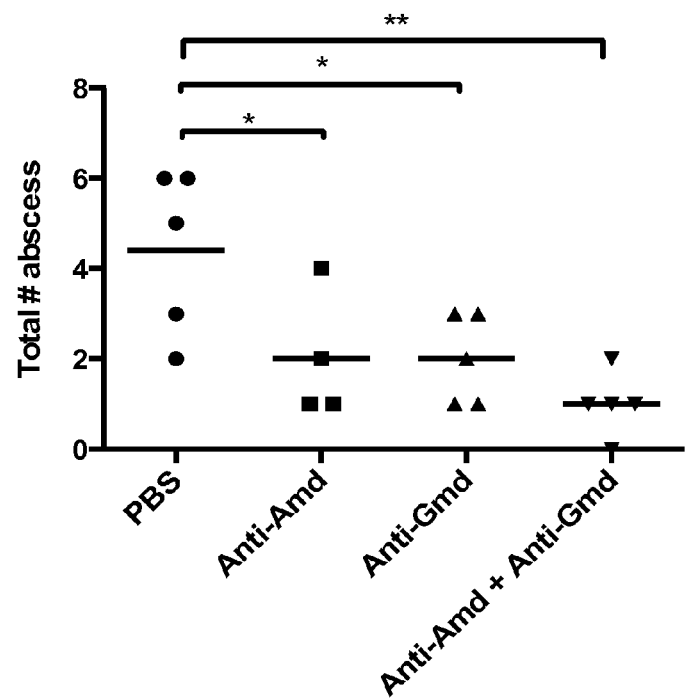
FIG. 8C

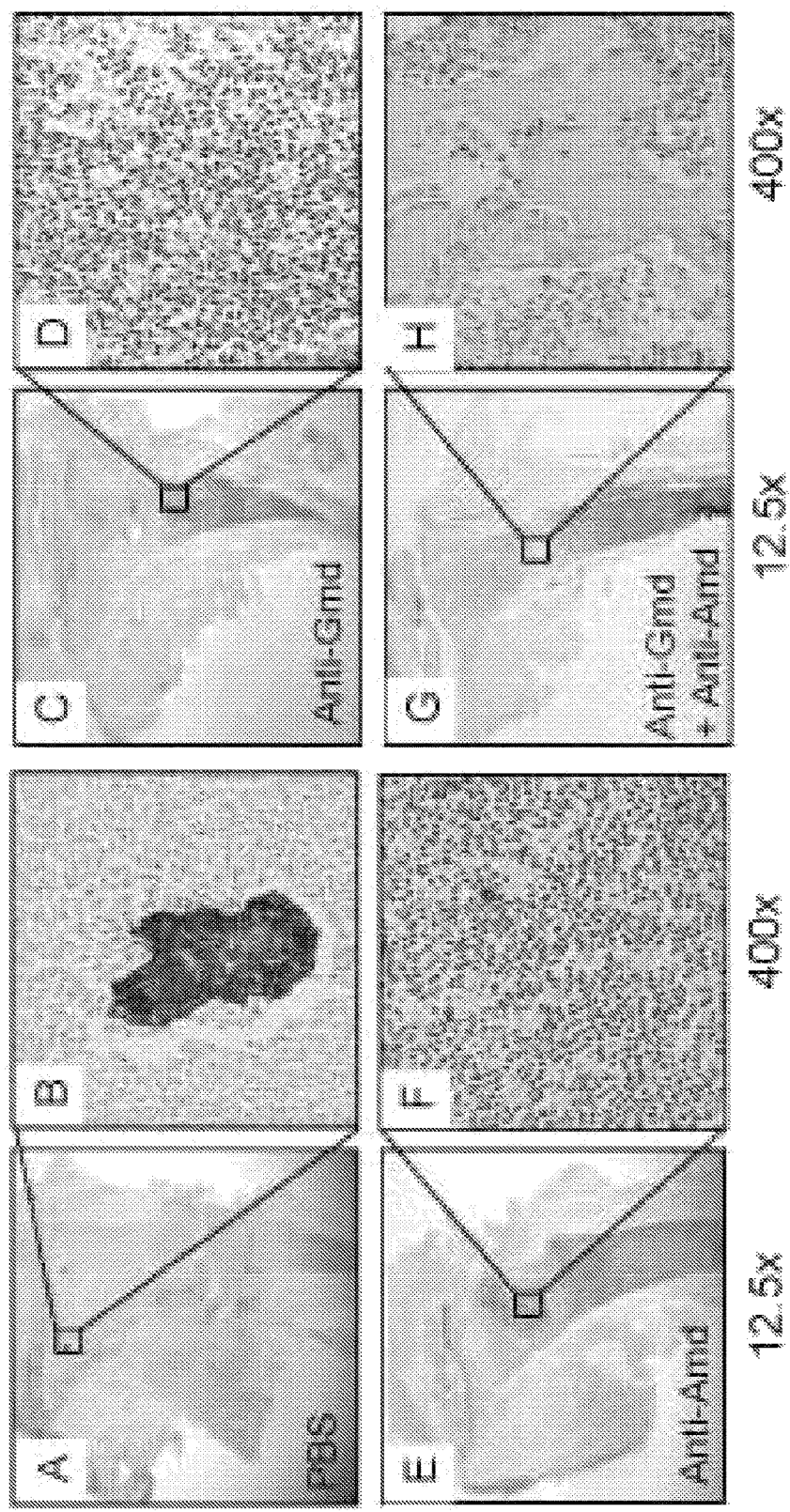
FIGS. 9A-H

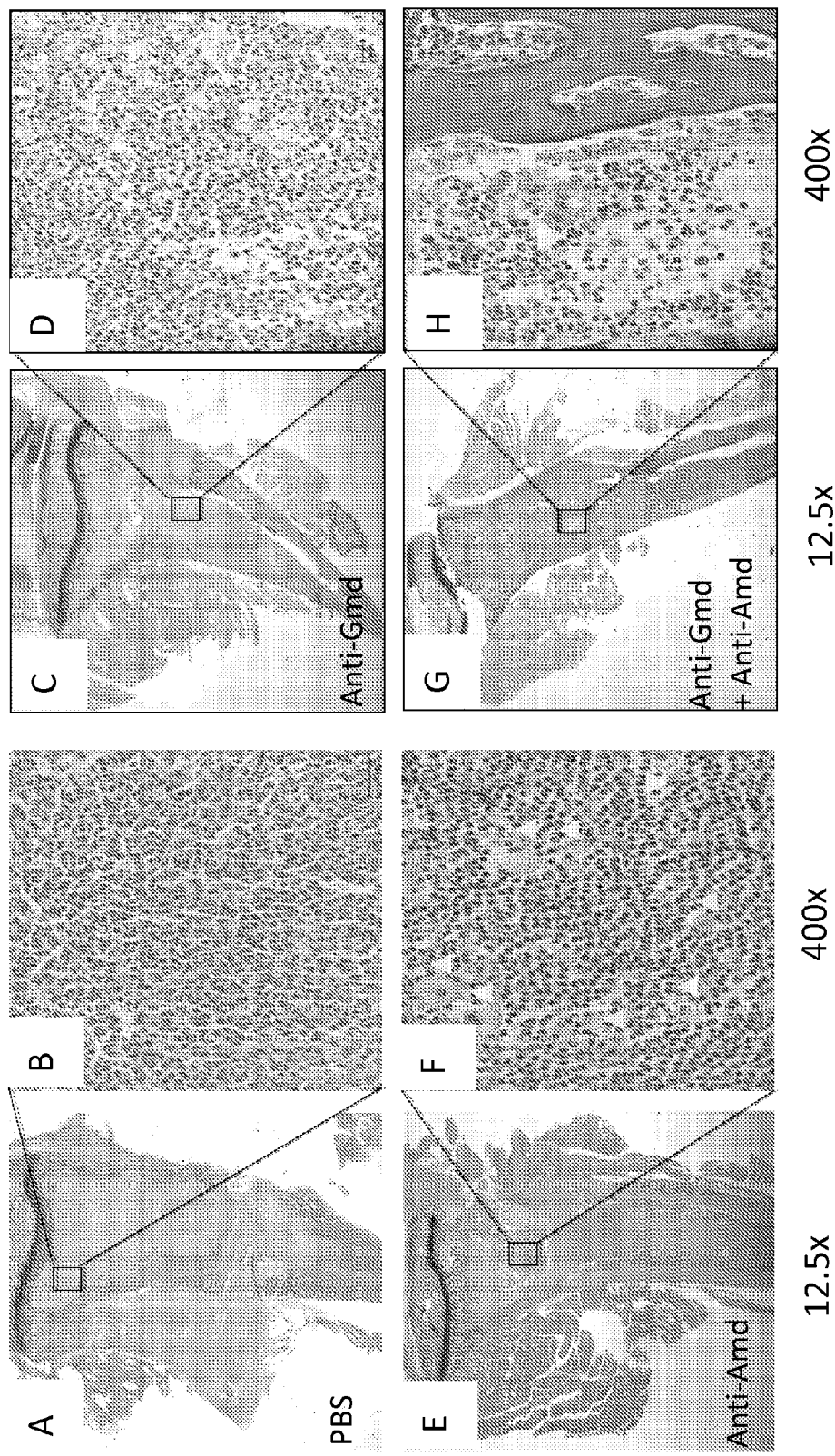
FIGS. 10A-H

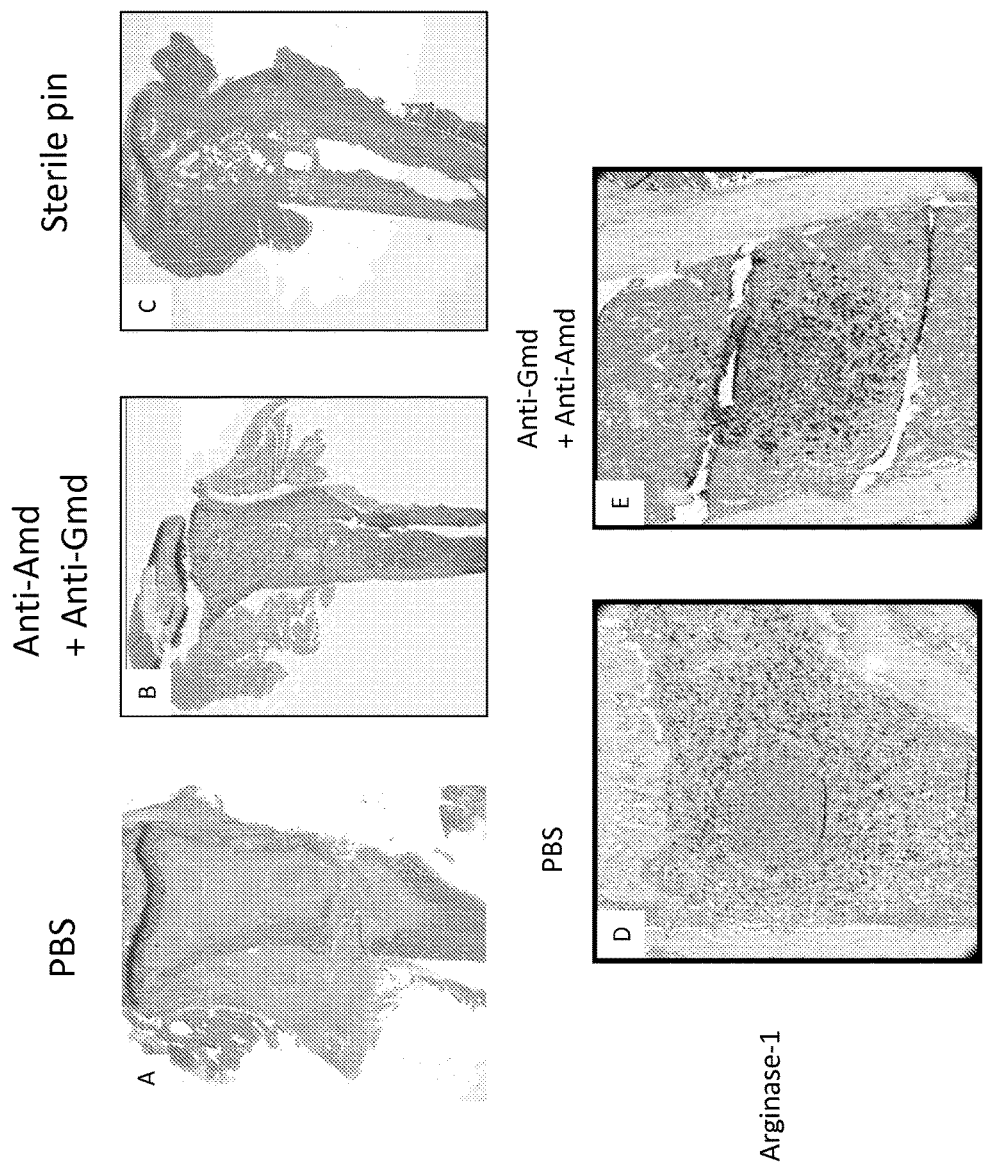
FIGS. 11A-E

PASSIVE IMMUNIZATION FOR *STAPHYLOCOCCUS* INFECTIONS

This application is a national stage application under 35 U.S.C. § 371 of PCT Application No. PCT/US2014/070337, filed 15 Dec. 2014, which claims the priority benefit of U.S. Provisional Patent Application Ser. No. 61/915,953, filed Dec. 13, 2013, which is hereby incorporated by reference in its entirety.

FIELD OF USE

Disclosed herein are methods and compositions for the passive immunization against *Staphylococcus* infection, particularly for the prevention or treatment of osteomyelitis and for infections arising from implantation of a medical device, or an orthopedic implant or graft. Antibodies that bind specifically to a *Staphylococcus* spp. autolysin N-acetylmuramoyl-L-alanine amidase catalytic domain and/or cell wall binding domain, and pharmaceutical compositions containing the same can be used for these purposes.

BACKGROUND

There is a great need for novel interventions of chronic osteomyelitis (OM) as approximately 112,000 orthopedic device-related infections occur per year in the US, at an approximate hospital cost of $15,000-70,000 per incident (Darouiche, "Treatment of Infections Associated With Surgical Implants," *N. Engl. J. Med.* 350(14):1422-9 (2004)). Although improvements in surgical technique and aggressive antibiotic prophylaxis have decreased the infection rate following orthopedic implant surgery to 1-5%, osteomyelitis (OM) remains a serious problem and appears to be on the rise from minimally invasive surgery (Mahomed et al., "Rates and Outcomes of Primary and Revision Total Hip Replacement in the United States Medicare Population," *J. Bone Joint Surg. Am.* 85(A-1):27-32 (2003); WHO Global Strategy for Containment of Antimicrobial Resistance, 2001). The significance of this resurgence, 80% of which is due to *Staphylococcus aureus*, is amplified by the fact that ~50% of clinical isolates are methicillin resistant *S. aureus* (MRSA). While the infection rates for joint prostheses and fracture-fixation devices have been only 0.3-11% and 5-15% of cases, respectively, over the last decade (Lew and Waldvogel, "Osteomyelitis," *Lancet* 364(9431):369-79 (2004); Toms et al., "The Management of Peri-Prosthetic Infection in Total Joint Arthroplasty," *J. Bone Joint Surg. Br.* 88(2): 149-55 (2006)), this result may lead to amputation or death. Additionally, the popularization of "minimally invasive surgery" for elective total joint replacements (TJR) in which the very small incision often leads to complications from the prosthesis contacting skin during implantation, has markedly increased the incidence of OM (Mahomed et al., "Rates and Outcomes of Primary and Revision Total Hip Replacement in the United States Medicare Population," *J. Bone Joint Surg. Am.* 85(A-1):27-32 (2003); WHO Global Strategy for Containment of Antimicrobial Resistance, 2001). These infections require a very expensive two-stage revision surgery, and recent reports suggest that success rates could be as low as 50% (Azzam et al., "Outcome of a Second Two-stage Reimplantation for Periprosthetic Knee Infection," *Clin. Orthop. Relat. Res.* 467(7):1706-14 (2009)). However, the greatest concern is the emergence of drug-resistant staphylococcal strains, most notably MRSA, which has surpassed HIV as the most deadly pathogen in North America, and continues to make the management of chronic OM more difficult and expensive, resulting in a great demand for novel therapeutic interventions to treat patients with these infections. There is a great need for alternative interventional strategies, particularly for immune-compromised elderly who are the primary recipients of TJR.

Presently, there are no prophylactic treatments that can protect high-risk patients from MRSA, most notably the aging "baby boomers" who account for most of the 1.5 million TJR performed annually in the United States. A vaccine that would decrease the MRSA incidence by 50-80% would not only reduce the number one complication of joint replacement and open fracture repair procedures, but also cut the healthcare burden by a similar amount.

Studies have documented that 80% of chronic OM is caused by *S. aureus*. These bacteria contain several factors that make them bone pathogens including several cell-surface adhesion molecules that facilitate their binding to bone matrix (Flock et al., "Cloning and Expression of the Gene for a Fibronectin-Binding Protein from *Staphylococcus aureus*," *EMBO J.* 6(8):2351-7 (1987)), toxins capable of stimulating bone resorption (Nair et al., "Surface-Associated Proteins from *Staphylococcus aureus* Demonstrate Potent Bone Resorbing Activity," *J. Bone Miner. Res.* 10(5): 726-34 (1995)), and degradation of bone by stimulating increased osteoclast activity (Marriott et al., "Osteoblasts Express the Inflammatory Cytokine Interleukin-6 in a Murine Model of *Staphylococcus aureus* Osteomyelitis and Infected Human Bone Tissue," *Am. J. Pathol.* 164(4):1399-406 (2004)). The rate-limiting step in the evolution and persistence of infection is the formation of biofilm around implanted devices (Costerton et al., "Bacterial Biofilms: A Common Cause of Persistent Infections," *Science* 284 (5418):1318-22 (1999)). Shortly after implantation, a conditioning layer composed of host-derived extracellular matrix components (including fibrinogen, fibronectin, and collagen) forms on the surface of the implant and invites the adherence of either free-floating bacteria derived from hematogenous seeding, or bacteria from a contiguous nidus of infection such as from the skin adjacent to a wound, surgical inoculation of bacteria into bone, or trauma coincident with significant disruption of the associated soft tissue bone envelope (Darouiche, "Treatment of Infections Associated With Surgical Implants," *N. Engl. J. Med.* 350(14): 1422-9 (2004)). Over the next few days, increased colonial adhesion, bacterial cell division, recruitment of additional planktonic organisms, and secretion of bacterial extracellular polymeric substances (such as those that form the glycocalyx) produces a bacterial biofilm. This biofilm serves as a dominant barrier to protect the bacteria from the action of antibiotics, phagocytic cells and antibodies and impairs host lymphocyte functions (Gray et al., "Effect of Extracellular Slime Substance from *Staphylococcus epidermidis* on the Human Cellular Immune Response," *Lancet* 1(8373):365-7 (1984); Johnson et al., "Interference with Granulocyte Function by *Staphylococcus epidermidis* Slime," *Infect. Immun.* 54(1):13-20 (1986); Naylor et al., "Antibiotic Resistance of Biomaterial-Adherent Coagulase-Negative and Coagulase-Positive Staphylococci," *Clin. Orthop. Relat. Res.* 261:126-33 (1990)).

Another recent discovery is that *S. aureus* not only colonizes bone matrix, but is also internalized by osteoblasts in vitro (Ellington et al., "Involvement of Mitogen-Activated Protein Kinase Pathways in *Staphylococcus aureus* Invasion of Normal Osteoblasts," *Infect. Immun.* 69(9):5235-42 (2001)) and in vivo (Reilly et al., "In Vivo Internalization of *Staphylococcus aureus* by Embryonic Chick Osteoblasts," *Bone* 26(1):63-70 (2000)). This provides yet another layer of antibody and antibiotic resistance. This phase of infection occurs under conditions of markedly reduced metabolic activity and sometimes appears as so-called small-colony variants that likely accounts for its persistence (Proctor et al., "Persistent and Relapsing Infections Associated with Small-Colony Variants of *Staphylococcus aureus*," *Clin. Infect. Dis.* 20(1):95-102 (1995)). At this point the bacteria may also express phenotypic resistance to antimicrobial treatment, also explaining the high failure rate of short courses of therapy (Chuard et al., "Resistance of *Staphylococcus aureus* Recovered From Infected Foreign Body in Vivo to Killing by Antimicrobials," *J. Infect. Dis.* 163(6): 1369-73 (1991)). Due to these extensive pathogenic mechanism, OM is notorious for its tendency to recur even after years of quiescence, and it is accepted that a complete cure is an unlikely outcome (Mader and Calhoun, "Long-Bone Osteomyelitis Diagnosis and Management," *Hosp. Pract. (Off Ed)* 29(10):71-6, 9, 83 passim (1994)).

One of the key questions in the field of chronic OM is why current knowledge of factors that regulate chronic OM is so limited. Supposedly, the experimental tools necessary to elucidate bacterial virulence genes have been available for over a century. There are three explanations for this anomaly. First, although the total number of osteomyelitis cases is high, its incidence of 1-5% is too low for rigorous prospective clinical studies, with the possible exception of revision arthroplasty. Second, it is well known that in vitro cultures rapidly select for growth of organisms that do not elaborate an extracellular capsule, such that biofilm biology can only be studied with in vivo models (Costerton et al., "Bacterial Biofilms: A Common Cause of Persistent Infections," *Science* 284(5418):1318-22 (1999)). This leads to the "greatest obstacle" in this field, which is the absence of a quantitative animal model that can assess the initial planktonic growth phase of the bacteria prior to biofilm formation. To date, much of the knowledge of its pathogenesis comes from animal models (Norden, "Lessons Learned from Animal Models of Osteomyelitis," *Rev. Infect. Dis.* 10(1):103-10 (1988)), which have been developed for the chicken (Daum et al., "A Model of *Staphylococcus aureus* Bacteremia, Septic Arthritis, and Osteomyelitis in Chickens," *J. Orthop. Res.* 8(6):804-13 (1990)), rat (Rissing et al., "Model of Experimental Chronic Osteomyelitis in Rats," *Infect. Immun.* 47(3):581-6 (1985)), guinea pig (Passl et al., "A Model of Experimental Post-Traumatic Osteomyelitis in Guinea Pigs," *J. Trauma* 24(4):323-6 (1984)), rabbit (Worlock et al., "An Experimental Model of Post-Traumatic Osteomyelitis in Rabbits," *Br. J. Exp. Pathol.* 69(2):235-44 (1988)), dog (Varshney et al., "Experimental Model of Staphylococcal Osteomyelitis in Dogs," *Indian J. Exp. Biol.* 27(9):816-9 (1989)), sheep (Kaarsemaker et al., "New Model for Chronic Osteomyelitis With *Staphylococcus aureus* in Sheep," *Clin. Orthop. Relat. Res.* 339:246-52 (1997)) and most recently mouse (Marriott et al., "Osteoblasts Express the Inflammatory Cytokine Interleukin-6 in a Murine Model of *Staphylococcus aureus* Osteomyelitis and Infected Human Bone Tissue," *Am. J. Pathol.* 164(4):1399-406 (2004)). While these models have been used to confirm the importance of bacterial adhesins identified from in vitro assays (Chuard et al., "Susceptibility of *Staphylococcus aureus* Growing on Fibronectin-Coated Surfaces to Bactericidal Antibiotics," *Antimicrob. Agents Chemother.* 37(4): 625-32 (1993); Buxton et al., "Binding of a *Staphylococcus aureus* Bone Pathogen to Type I Collagen," *Microb. Pathog.* 8(6):441-8 (1990); Switalski et al., "A Collagen Receptor on *Staphylococcus aureus* Strains Isolated From Patients With Septic Arthritis Mediates Adhesion to Cartilage," *Mol. Microbiol.* 7(1):99-107 (1993)), they do not have an outcome measure of in vivo growth, bacterial load, or osteolysis. Thus, they cannot be efficiently used to assess drug effects, bacterial mutants, and the role of host factors with transgenic mice.

Based on over 150 years of research, a clear paradigm to explain staphylococcal pathogenesis has emerged. This model also applies to OM. The initial step of infection occurs when a unicellular *bacterium* invades the body. At this point the microbe must respond to environmental changes and express virulence genes that will help it defeat innate immunity and provide it with adhesin receptors to attach to the host. The *bacterium* is also dependent on the stochastic availability of host adhesion targets from necrotic tissue or a foreign body such as an implant for adherence and surface colonization to occur. Successful completion of these steps leads to an exponential biofilm growth phase, which ceases at the point of nutrient exhaustion and/or the development of adaptive immunity. Following the exponential growth phase the bacteria persist under dormant growth conditions within a multilayered biofilm until quorum sensing-driven changes in gene expression allow for portions of the biofilm to detach as planktonic cells or mobile segments of biofilm patches (Yarwood, et al., "Quorum Sensing in *Staphylococcus aureus* Biofilms," *J. Bact.* 186(6): 1838-1850 (2004)). However, at this point the infection is now chronic and cannot be eradicated by drugs or host immunity. Thus, the focus in this field has been on cell surface extracellular matrix components that specifically interact with a class of bacterial adhesins known as MSCRAMMs (microbial surface components recognizing adhesive matrix molecules) (Patti et al., "MSCRAMM-Mediated Adherence of Microorganisms to Host Tissues," *Annu. Rev. Microbiol.* 48:585-617 (1994)). In fact, essentially all anti-*S. aureus* vaccines developed to date have been directed against MSCRAMMs that are important for host tissue colonization and invasion. The goal of these vaccines is to generate antibodies that bind to these bacterial surface antigens, thereby inhibiting their attachment to host tissue and suppressing the biofilm formation which serves as a long term reservoir of infection. By opsonizing the bacterial surface, these antibodies can also mediate *S. aureus* clearance by phagocytic cells. Unfortunately, *S. aureus* has many adhesins, such that inhibition of one or more may not be sufficient to prevent bacterial attachment. Furthermore, bacterial clearance by phagocytic cells may be limited in avascular tissue such as bone such that an antibody alone may need additional anti-microbial mechanisms of action to significantly reduce the in vivo planktonic growth of *S. aureus* and prevent the establishment of chronic OM or reinfection during revision total joint replacement surgery.

While PCT Publication Nos. WO2011/140114 and WO2013/066876 to Schwarz et al. describe several monoclonal antibodies (hereinafter "mAbs") that bind specifically to *Staphylococcus* glucosaminidase and inhibit in vivo growth of a *Staphylococcus* strain, there remains a need to identify additional mAbs that bind specifically to a different *Staphylococcus* target and inhibit its function.

The disclosed invention is directed to overcoming these and other deficiencies in the art.

SUMMARY OF THE DISCLOSURE

A first aspect relates to a monoclonal antibody or binding portion thereof that binds specifically to a *Staphylococcus* spp. autolysin N-acetylmuramoyl-L-alanine amidase catalytic domain or cell wall binding domain.

A second aspect relates to a cell line that expresses a monoclonal antibody or binding portion thereof as disclosed herein.

A third aspect relates to a pharmaceutical composition that includes a carrier and one or more monoclonal antibodies or monoclonal antibody binding portions as disclosed herein.

A fourth aspect relates to a method of introducing an orthopedic implant or medical device into a patient that involves administering to a patient in need of an orthopedic implant an effective amount of a monoclonal antibody or monoclonal antibody binding portion according to the first aspect as disclosed herein, a pharmaceutical composition according to the third aspect as disclosed herein, or a combination thereof, and introducing the orthopedic implant, tissue graft, or medical device into the patient.

A fifth aspect relates to a method of treating or preventing a Staphylococcus infection that includes administering to a patient susceptible to or having a Staphylococcus infection an effective amount of a monoclonal antibody or monoclonal antibody binding portion according to the first aspect as disclosed herein, a pharmaceutical composition according to the third aspect as disclosed herein, or a combination thereof.

A sixth aspect relates to a method of treating osteomyelitis that involves administering to a patient having a Staphylococcus bone or joint infection an effective amount of a monoclonal antibody or monoclonal antibody binding portion according to the first aspect as disclosed herein, a pharmaceutical composition according to the third aspect as disclosed herein, or a combination thereof.

A seventh aspect relates to a method of determining the presence of Staphylococcus in a sample that involves exposing a sample to a monoclonal antibody or binding portion according to the first aspect as disclosed herein, and detecting whether an immune complex forms between the monoclonal antibody or binding portion and Staphylococcus or a Staphylococcus amidase present in the sample, whereby the presence of the immune complex after said exposing indicates that presence of Staphylococcus in the sample.

Staphylococcus N-acetylmuramoyl-L-alanine amidase (hereinafter "Amd" or "amidase") has several properties that make it an attractive target for passive immunization. The amidase is involved in multiple crucial cell functions including bacterial cell adhesion, cell division, secretion and biofilm glycocalyx formation through its mediation of autolysis which produces glycocalyx extracellular DNA; it is highly conserved among S. aureus clinical isolates; it is the target of vancomycin and it expressed throughout the cell cycle. Further, because Amd is displayed on the cell wall, it is accessible to antibodies present in the extracellular milieu.

The monoclonal antibodies and binding portions thereof, as well as pharmaceutical compositions containing the same, are therapeutic agents suitable for immunotherapy in patients with or at risk for infection by Staphylococcus strains. The power of these monoclonal antibodies is derived from their multiple activities that will hinder growth, adhesion, and immune evasion by Staphylococcus strains. First, as antibodies, they will promote phagocytosis by neutrophils at the site of incipient Staphylococcus infections. Second, as inhibitors of the Staphylococcus amidase, an enzyme with multiple roles in Staphylococcus survival and surface colonization, these antibodies potentially hinder one or both of cell division and biofilm formation. Finally, as demonstrated herein, the disclosed antibodies reduce Staphylococcus spread, as evidenced by the formation of fewer abscesses, and afford macrophage invasion of abscesses, which promotes the formation of sterile abscesses and accelerates bone healing.

BRIEF DESCRIPTION OF THE DRAWINGS

FIGS. 6A-E illustrate the effect of passive immunization with anti-Amd monoclonal antibodies and a combination of anti-Amd and anti-Gmd monoclonal antibodies on biofilm formation on implants in vivo as compared to autolysin deficiency. Six-to-ten week old, female Balb/c mice (n≥3) were passively immunized intraperitoneally with anti-Amd (Amd1.6), a combination of anti-Amd and anti-Gmd (Amd1.6+1C11) or an IgG isotype-matched control mAb at a dose of 40 mg/kg. One day later each mouse was infected with a trans-tibial stainless steel pin contaminated with USA300 LAC CA-MRSA strain or its isogenic Δatl mutant. The pins were left in place to allow the biofilm-based infection to mature. On Day 14 post-infection the pins were removed and examined by scanning electron microscopy (SEM). Representative micrographs showing the extent of biofilm formation on the infected implants (pins) are shown: IgG control (FIG. 6A); anti-Amd (Amd1.6, FIG. 6B); anti-Amd+anti-Gmd (Amd1.6+1C11, FIG. 6C); and infected with Δatl mutant (FIG. 6D). The percentage of the region of interest (the 0.5×2.0 mm face of the flat pin) covered with biofilm was quantified with NIH software (Image J) and shown in FIG. 6E; * $p<0.05$.

FIGS. 8A-C illustrate the effects of passive immunization with Amd1.6, which show significantly reduced bacterial spread as evidenced by the formation of fewer abscesses in the medullary canal. 6-10 week old, female Balb/c mice (n=5) were immunized intraperitoneally with PBS (negative control), anti-Gmd mAb 1C11, anti-Amd mAb Amd1.6 or a combination (1C11+Amd1.6) at a total dose of 40 mg/kg. Twenty-four hours later each mouse had inserted through its right tibia a pin contaminated with USA300 LAC::lux, a bioluminescent CA-MRSA strain. The resulting infection was allowed to progress for fourteen days when the animals were sacrificed and the infected tibiae were harvested, fixed, decalcified and sectioned for histological analysis. Representative infected tibiae stained with Orange G/alcian blue (ABG/OH) are depicted for (FIG. 8A) untreated controls and (FIG. 8B) mice treated with the combination of anti-Gmd 1C11 and anti-Amd Amd1.6. The number of abscesses observed in each group of mice is presented in (FIG. 8C). *, $p<0.05$; **, $p<0.01$.

FIGS. 9A-H illustrate the effect of passive immunization with anti-Amd, anti-Gmd, and a combination of anti-Amd and anti-Gmd monoclonal antibodies in preventing formation of staphylococcal abscess communities (SACs), which leads to sterile abscesses. Mice (n=5) were immunized i.p. with PBS (negative control) or mAbs 1C11, Amd1.6 or a combination (1C11+Amd1.6) at a 40 mg/kg dose. Twenty-four hours later all mice received a trans-tibial pin contaminated with USA300 LAC::lux bioluminescent CA-MRSA strain. Representative infected tibias from Day 14 post-infection are shown for histology sections that were Gram-stained to reveal the bacteria. PBS-treated tibias show typical SAC pathology, containing a central nidus of bacteria surrounded by an eosinophilic pseudocapsule within the abscess area (FIGS. 9A-B) that are absent in mice treated with the following mAbs: 1C11 (FIGS. 9C-D), Amd1.6 (FIGS. 9E-F), and combination 1C11+Amd1.6 (FIGS. 9G-H).

FIGS. 10A-H illustrate the effect of passive immunization with anti-Amd, anti-Gmd, and a combination of anti-Amd and anti-Gmd monoclonal antibodies on recruitment of macrophage-like cells within the abscess. Six-to-ten week old female Balb/c mice (n=5) were immunized i.p. with PBS or mAb 1C11, Amd1.6 or a combination (1C11+Amd1.6) at a 40 mg/kg dose. Twenty-four hours later all mice received an trans-tibial pin contaminated with USA300 LAC::lux bioluminescent CA-MRSA strain. Representative infected tibias from Day 14 post-infection are shown for histology sections that were stained with Orange G/alcian blue (ABG/OH). Passive immunization with anti-Amd, anti-Gmd, and a combination of anti-Amd and anti-Gmd mAbs recruits macrophage-like cells to the center of abscess (FIGS. 10C-H, arrowheads) while the PBS immunized mice do not show macrophage-like cell recruitment within the abscess (FIGS. 10A-B) and display cells that morphologically resemble neutrophils. Multiple abscesses are present in PBS treated tibias (FIG. 10A) in the medullary canal and soft tissue around the bone, compared to a single abscess in Amd1.6 and combination 1C11+Amd1.6 treated mice (FIGS. 10E and 10G, respectively), or two abscess structures in 1C11 treated mice (FIG. 10C).

FIGS. 11A-E illustrate the effect of passive immunization with a combination of anti-Amd and anti-Gmd monoclonal antibodies, which accelerates bone healing by recruiting M2 macrophages within the sterile abscess. Six-to-ten week old female Balb/c mice (n=5) were immunized i.p. with PBS or mAb 1C11, Amd1.6 or a combination (1C11+Amd1.6) at a 40 mg/kg dose. Twenty-four hours later all mice received an trans-tibial pin contaminated with USA300 LAC::lux bioluminescent CA-MRSA strain. Representative tibias from Day 14 post-surgery are shown for histology sections that were stained with Orange G/alcian blue (ABG/OH) (FIGS. 11A-C). Remarkable healing is evident in mice immunized with the mAbs comparable to those receiving a sterile pin control (FIGS. 11A-C). To determine correlation of healing with macrophage phenotype associated with remodeling and wound healing process, immunohistochemistry was performed with anti-Arginase-1 antibody to stain M2 macrophages. M2 macrophages are recruited to the center of the abscess (brown staining) on mice that were passively immunized (FIG. 11E), but excluded from abscess center on negative control PBS group (FIG. 11D).

DETAILED DESCRIPTION

Figure 1:
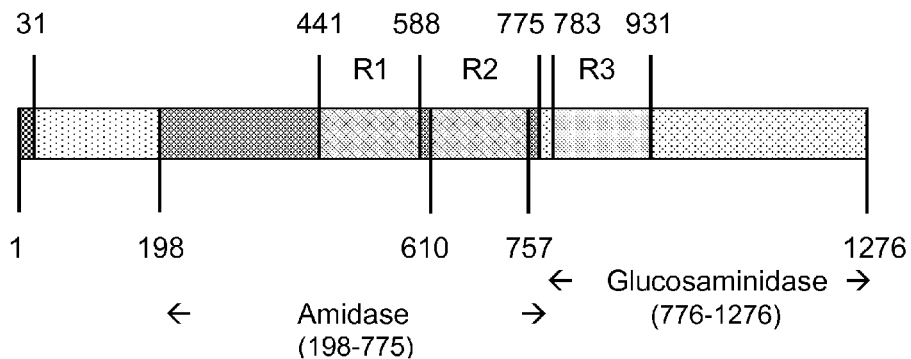
FIG. 1 is a schematic illustration of the domain structure of S. aureus bifunctional autolysin (At1A), which is representative of all Staphylococcus spp. bifunctional autolysin proteins. Bifunctional autolysin is synthesized as a 1276 amino acid pre-pro-enzyme. The 31-amino acid signal peptide (aa 1-31) is removed during secretion and the 167-amino acid pro-peptide (aa 32-197) is removed when the autolysin is inserted into the cell wall. After cell division, the mature autolysin is cleaved at amino acid 775 to yield independent AmdR1R2 (N-acetylmuramoyl-L-alanine amidase, or amidase (Amd); aa 198-775) and R3Gmd (endo-β-N-acetylglucosaminidase (Gmd); aa 776-1276).

Disclosed herein are one or more monoclonal antibodies or binding portions thereof that binds specifically to a *Staphylococcus* spp. autolysin N-acetylmuramoyl-L-alanine amidase (Amd) catalytic domain or cell wall binding domain.

As used herein, the term "antibody" is meant to include immunoglobulins derived from natural sources or from recombinant sources, as well as immunoreactive portions (i.e. antigen binding portions) of immunoglobulins. The monoclonal antibodies disclosed herein may exist in or can be isolated in a variety of forms including, for example, substantially pure monoclonal antibodies, antibody fragments or binding portions, chimeric antibodies, and humanized antibodies (Ed Harlow and David Lane, USING ANTIBODIES: A LABORATORY MANUAL (Cold Spring Harbor Laboratory Press, 1999), which is hereby incorporated by reference in its entirety).

The monoclonal antibodies disclosed herein are characterized by specificity for binding to *Staphylococcus* N-acetylmuramoyl-L-alanine-amidase or fragments thereof. The antibody specifically binds to an epitope, typically though not exclusively an immuno-dominant epitope, in the amidase sub-unit of *Staphylococcus* autolysin (Atl). In certain embodiments, these monoclonal antibodies inhibit in vivo growth of a *Staphylococcus* strain. In other embodiments, these monoclonal antibodies inhibit biofilm establishment on metal, plastic and/or organic surfaces. In still further embodiments, one or more monoclonal antibodies can be used together to inhibit both in vivo growth of a *Staphylococcus* strain and biofilm establishment on metal, plastic and/or organic surfaces.

In accordance with this and all other aspects disclosed herein, the *Staphylococcus* strain is a strain that is, or can be, pathogenic to humans or animals. The *Staphylococcus* can be either coagulase-positive or coagulase-negative. Exemplary *Staphylococcus* strains include, without limitation, *S. aureus, S. epidermidis, S. lugdunensis, S. saprophyticus, S. haemolyticus, S. caprae*, and *S. simiae*. In one embodiment, the monoclonal antibodies disclosed herein are effective against antibiotic-resistant strains of *Staphylococcus*, including methicillin-resistant or vancomycin-resistant strains.

In certain embodiments, the epitope of the amidase subunit (that is bound by the mAb or binding fragment thereof) is an immuno-dominant epitope. Immuno-dominant antigen is a part of the antigenic determinant that is most easily recognized by the immune system and thus exerts the most influence on the specificity of the induced antibody. An "immuno-dominant epitope" refers to the epitope on an antigen that selectively provokes an immune response in a host organism to the substantial exclusion of other epitopes on that antigen.

Usually, the antigen likely to carry an immuno-dominant epitope can be identified by selecting antigens on the outer surface of the pathogenic organism. For example, most simple organisms, such as fungi, bacteria and viruses have one or two proteins that are exposed on the outer surface of the pathogenic organism. These outer surface proteins are most likely to carry the appropriate antigen. The proteins most likely to carry an immuno-dominant epitope can be identified in a Western assay in which total protein is run on a gel against serum from an organism infected with the pathogenic organism. Bound antibodies from the serum are identified by labeled anti-antibodies, such as in one of the well-known ELISA techniques. The immuno-dominant epitope can be identified by examining serum from a host organism infected with the pathogenic organism. The serum is evaluated for its content of antibodies that bind to the identified antigens that are likely to cause an immune response in a host organism. If an immuno-dominant epitope is present in these antigens, substantially all antibodies in the serum will bind to the immuno-dominant epitope, with little binding to other epitopes present in the antigen.

AtlA is one of the catalytically distinct peptidoglycan hydrolases in *Staphylococcus aureus* that is required to digest the cell wall during mitosis (Baba and Schneewind, "Targeting of Muralytic Enzymes to the Cell Division Site of Gram-Positive Bacteria: Repeat Domains Direct Autolysin to the Equatorial Surface Ring of *Staphylococcus aureus*," *EMBO. J.* 17(16):4639-46 (1998), which is hereby incorporated by reference in its entirety). In addition to being an essential gene for growth, scanning electron microscopy studies have demonstrated that anti-AtlA antibodies bound to *S. aureus* during binary fission localize to regions of the bacteria that are not covered by the cell wall (Yamada et al., "An Autolysin Ring Associated With Cell Separation of *Staphylococcus aureus*," *J. Bacteriol.* 178(6): 1565-71 (1996), which is hereby incorporated by reference in its entirety).

The AtlA enzyme is comprised of an amidase (62 kD) and glucosaminidase (53 kD), which are produced from the same AtlA precursor protein via a cleavage process (Baba and Schneewind, "Targeting of Muralytic Enzymes to the Cell Division Site of Gram-Positive Bacteria: Repeat Domains Direct Autolysin to the Equatorial Surface Ring of *Staphylococcus aureus*," *Embo. J.* 17(16):4639-46 (1998); Komatsuzawa et al., "Subcellular Localization of the Major Autolysin, ATL and Its Processed Proteins in *Staphylococcus aureus*," *Microbiol Immunol.* 41:469-79 (1997); Oshida et al., "A *Staphylococcus aureus* Autolysin That Has an N-acetylmuramoyl-L-alanine Amidase Domain and an Endo-beta-N-acetylglucosaminidase Domain: Cloning, Sequence Analysis, and Characterization," *Proc. Nat'l. Acad. Sci. U.S.A.* 92(1):285-9 (1995), which are hereby incorporated by reference in their entirety). The autolysin is held to the cell wall by three ~150 amino acid cell wall binding domains, which are designated as R1, R2, and R3. In the final maturation step, proteolytic cleavage separates the amidase domain and its associated R1 and R2 domains (collectively, "Amd") from the glucosaminidase and its associated N-terminal R3 domain (collectively, "Gmd"). See FIG. 1.

Exemplary encoded consensus protein and encoding open reading frame sequences for His-Amd are identified as SEQ ID NOS: 1 and 2 below.

SEQ ID NO: 1
MHHHHHHSASAQPRSVAATPKTSLPKYKPQVNSSINDYIRKNNLKAPKIE

EDYTSYFPKYAYRNGVGRPEGIVVHDTANDRSTINGEISYMKNNYQNAFV

HAFVDGDRIIETAPTDYLSWGVGAVGNPRFINVEIVHTHDYASFARSMNN

-continued

YADYAATQLQYYGLKPDSAEYDGNGTVWTHYAVSKYLGGTDHADPHGYLR

SHNYSYDQLYDLINEKYLIKMGKVAPWGTQSTTTPTTPSKPTTPSKPSTG

KLTVAANNGVAQIKPTNSGLYTTVYDKTGKATNEVQKTFAVSKTATLGNQ

KFYLVQDYNSGNKFGWVKEGDVVYNTAKSPVNVNQSYSIKPGTKLYTVPW

GTSKQVAGSVSGSGNQTFKASKQQQIDKSIYLYGSVNGKSGWVSKAYLVD

TAKPTPTPTPKPSTPTTNNKLTVSSLNGVAQINAKNNGLFTTVYDKTGKP

TKEVQKTFAVTKEASLGGNKFYLVKDYNSPTLIGWVKQGDVIYNNAKSPV

NVMQTYTVKPGTKLYSVPWGTYKQEAGAVSGTGNQTFKATKQQQIDKSIY

LFGTVNGKSGWVSKAYLAVPAAPKKAVAQPKTAVK

SEQ ID NO: 2
ATGCACCATCACCACCACCACAGCGCAAGCGCACAGCCTCGTTCCGTCGC

CGCCACCCCGAAAACCAGCTTGCCGAAGTACAAACCGCAAGTTAATAGCA

GCATCAACGACTACATCCGCAAAAACAACCTGAAGGCCCCGAAAATTGAA

GAGGACTATACCAGCTATTTCCCGAAATATGCTTACCGTAATGGTGTCGG

TCGTCCGGAGGGTATTGTGGTCCACGACACCGCGAATGACCGTAGCACCA

TCAACGGTGAGATTAGCTACATGAAAAACAATTACCAAAACGCGTTCGTG

CACGCCTTCGTCGATGGCGATCGCATCATCGAAACCGCGCCAACCGACTA

TCTGTCCTGGGGTGTGGGTGCCGTTGGCAACCCGCGTTTCATCAATGTGG

AGATTGTTCATACCCACGACTACGCGAGCTTTGCACGTAGCATGAACAAC

TACGCCGATTATGCTGCAACGCAGCTGCAGTACTACGGCCTGAAACCGGA

TAGCGCGGAGTATGACGGTAACGGTACGGTGTGGACGCATTATGCGGTGA

GCAAATACCTGGGTGGTACCGATCATGCTGATCCGCATGGCTACCTGCGC

TCTCACAACTATAGCTACGACCAGTTGTACGACCTGATCAATGAGAAATA

TCTGATTAAGATGGGTAAGGTTGCACCGTGGGGTACGCAGAGCACCACGA

CGCCGACCACGCCGAGCAAACCGACGACCCCGTCCAAACCGTCTACCGGC

AAACTGACGGTCGCGGCTAATAACGGTGTCGCGCAGATTAAACCGACCAA

CAGCGGTCTGTACACCACCGTCTATGATAAAACGGGCAAAGCCACCAATG

AGGTTCAAAAGACGTTCGCAGTTAGCAAAACGGCGACCCTGGGTAACCAA

AAGTTCTACCTGGTTCAGGATTACAATAGCGGCAACAAATTTGGTTGGGT

GAAAGAAGGCGACGTTGTGTACAATACCGCGAAGTCCCCGGTGAACGTTA

ATCAGAGCTATAGCATCAAGCCGGGTACCAAATTGTATACGGTGCCGTGG

GGTACCAGCAAGCAAGTTGCGGGTAGCGTCAGCGGCTCTGGTAACCAGAC

CTTCAAGGCGTCTAAGCAACAACAAATTGACAAAAGCATTTACCTGTATG

GTAGCGTTAATGGTAAAAGCGGCTGGGTGTCTAAAGCGTATCTGGTCGAC

ACCGCAAAGCCGACGCCAACGCCGACCCCGAAGCCGAGCACCCCAACCAC

CAACAACAAGCTGACGGTCAGCTCCCTGAATGGTGTTGCGCAAATCAATG

CGAAGAATAATGGCCTGTTTACCACCGTTTACGATAAGACGGGCAAGCCA

ACGAAAGAAGTCCAGAAAACCTTTGCTGTCACCAAAGAAGCCAGCCTGGG

CGGTAACAAGTTCTATCTGGTTAAGGACTACAACTCCCCGACGCTGATCG

GTTGGGTCAAACAAGGCGATGTCATTTACAATAACGCGAAAAGCCCGGTT

AATGTGATGCAAACCTATACCGTCAAACCGGGTACGAAGCTGTATTCCGT

TCCGTGGGGCACGTACAAACAAGAAGCAGGCGCGGTGAGCGGTACCGGCA

ATCAGACCTTTAAGGCCACCAAGCAGCAGCAGATCGATAAATCTATTTAC

TTGTTTGGCACCGTGAATGGCAAGAGCGGTTGGGTTTCTAAGGCATACCT

GGCGGTGCCGGCAGCACCGAAGAAGGCGGTGGCGCAGCCAAAGACCGCAG

TGAAG

The *Staphylococcus* Amd can be synthesized by solid phase or solution phase peptide synthesis, recombinant expression, or can be obtained from natural sources. Automatic peptide synthesizers are commercially available from numerous suppliers, such as Applied Biosystems, Foster City, Calif. Standard techniques of chemical peptide synthesis are well known in the art (see e.g., SYNTHETIC PEPTIDES: A USERS GUIDE 93-210 (Gregory A. Grant ed., 1992), which is hereby incorporated by reference in its entirety). Protein or peptide production via recombinant expression can be carried out using bacteria, such as *E. coli*, yeast, insect or mammalian cells and expression systems. Procedures for recombinant protein/peptide expression are well known in the art and are described by Sambrook et al, Molecular Cloning: A Laboratory Manual (C.S.H.P. Press, NY 2d ed., 1989).

Recombinantly expressed peptides can be purified using any one of several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC and/or dialysis.

In certain embodiments, the monoclonal antibodies or binding portions may bind specifically to an epitope of the Amd catalytic domain. As used herein, the Amd catalytic domain is at least 70% identical to amino acids 9-252 of SEQ ID NO: 1, or at least 75% or 80% identical to amino acids 9-252 of SEQ ID NO: 1, or even at least 85% or 90% identical to amino acids 9-252 of SEQ ID NO: 1. In certain embodiments, the amidase catalytic domain is at least 95% identical to amino acids 9-252 of SEQ ID NO: 1.

In certain embodiments, the monoclonal antibody or binding portion is produced by a hybridoma cell line designated as Amd1.6, Amd1.10, Amd1.13, Amd1.16, Amd1.17, Amd2.1, or Amd2.2.

In another embodiment, the monoclonal antibody or binding portion binds to an epitope wholly or partly within the Amd R1 or R2 cell wall binding domain. As used herein, the R1 or R2 cell wall binding domains are at least 70% identical to amino acids 253-399 or 421-568 of SEQ ID NO: 1, respectively; or at least 75% or 80% identical to amino acids 253-399 or 421-568 of SEQ ID NO: 1, respectively; or even at least 85% or 90% identical to amino acids 253-399 or 421-568 of SEQ ID NO: 1, respectively. In certain embodiments, the cell wall binding domains are at least 95% identical to amino acids 253-399 or 421-568 of SEQ ID NO: 1, respectively.

In certain embodiments, the monoclonal antibody or binding portion is produced by a hybridoma cell line designated Amd1.1, Amd1.2, Amd1.5, Amd1.7, Amd1.8, Amd1.9, Amd1.11, Amd1.12, Amd1.14, Amd1.15, Amd2.4, or Amd2.5.

In certain embodiments the monoclonal antibody disclosed herein binds to the Amd catalytic domain or cell wall binding domain with an affinity greater than $10^{-8}$ M or $10^{-9}$ M, but preferably greater than $10^{-10}$M.

As noted above, in certain embodiments the monoclonal antibodies or binding portions also inhibit in vivo growth of *Staphylococcus*. Inhibition of in vivo growth of *Staphylococcus* can be measured according to a number of suitable standards. In one such embodiment, the in vivo growth of *Staphylococcus* can be assessed according to a bioluminescence assay. By way of example, bioluminescent *S. aureus* (Xen 29; ATCC 12600) (Francis et al., "Monitoring Bioluminescent *Staphylococcus aureus* Infections in Living Mice Using a Novel luxABCDE Construct," *Infect. Immun.* 68(6): 3594-600 (2000); see also Contag et al., "Photonic Detection of Bacterial Pathogens in Living Hosts," *Mol. Microbiol.* 18(4):593-603 (1995), each of which is hereby incorporated by reference in its entirety) is used to dose a transtibial implant with 500,000 CFU prior to surgical implant. Five week old female BALB/cJ mice can receive an intraperitoneal injection of saline or 1 mg of purified antibody/antibody fragment in 0.25 ml saline 3 days prior to surgery. The mice can be imaged to assess bioluminescence on various days (e.g., 0, 3, 5, 7, 11, and 14) and a comparison of BLI images can be compared to assess whether the antibody inhibits in vivo growth of *S. aureus* relative to the saline control or a control mouse injected with a placebo antibody.

In another embodiment, the in vivo growth of *Staphylococcus* can be assessed according to biofilm formation. By way of example, female Balb/c mice can be passively immunized intraperitoneally with antibody/antibody fragment or control at a dose of 40 mg/kg, and one day later each mouse can be infected with a trans-tibial stainless steel pin contaminated with a MRSA strain. On day 14 post-infection the pins can be removed and examined by scanning electron microscopy (SEM), and the percentage of a region of interest (e.g., 0.5×2.0 mm face of the flat pin) covered with biofilm can be quantified with NIH software (Image J).

In yet another embodiment, the Osteolytic Volume of infected bone can be measured using MicroCT imaging. By way of example, female Balb/c mice can be passively immunized intraperitoneally with antibody/antibody fragment or control at a dose of 40 mg/kg, and one day later each mouse can be infected with a trans-tibial stainless steel pin contaminated with a MRSA strain. After 14 days, the mice can be euthanized and the tibia harvested. Using the resulting images, the lesion area can be measured in two different views (e.g., medial and lateral), which are added together and multiplied by the cortical thickness (see Varrone et al., "Passive Immunization With Anti-Glucosaminidase Monoclonal Antibodies Protects Mice From Implant-Associated Osteomyelitis by Mediating Opsonophagocytosis of *Staphylococcus aureus* Megaclusters," *J Orthop Res* 32(10):1389-96 (2014), which is hereby incorporated by reference in its entirety).

In yet another embodiment, in vivo growth of *Staphylococcus* can be assessed by the presence (including frequency) or absence of *Staphylococcus* abscess communities (SACs) in the medullary canal or soft tissue surrounding the bone. By way of example, female Balb/c mice can be passively immunized intraperitoneally with antibody/antibody fragment or control at a dose of 40 mg/kg, and one day later each mouse can be infected with a trans-tibial stainless steel pin contaminated with a MRSA strain. After 14 days, the mice can be euthanized and the tibia and associated soft tissue harvested. Histological samples can be prepared and stained with Orange G/alcian blue (ABG/OH), and then the presence or absence of abscesses can be determined upon analysis of the histologic samples.

According to one embodiment, the monoclonal antibody or binding portion comprises a $V_H$ domain comprising one of the following amino acid sequences (CDR domains underlined):

```
SEQ ID NO: 5 (Amd1.2):
PELVKPGASVKMSCKASGYTFTSYIMHWVKQKPGQGLEWIGYINPYNDGT

KYNEKFKGKATLTSDKSSTTAYMELSSLTSEDXAVYYCARLDGYYDCFDY

WGQGTTLTVSS
where X can be any amino acid. This amino acid
sequence is encoded by the following nucleotide
sequence (SEQ ID NO: 6):

CCTGAGCTGGTAAAGCCTGGGGCTTCAGTGAAGATGTCCTGCAAGGCTTC

TGGATACACATTCACTAGCTATATTATGCACTGGGTGAAGCAGAAGCCTG

GGCAGGGCCTTGAGTGGATTGGATATATTAATCCTTACAATGATGGTACT

AAGTACAATGAGAAGTTCAAAGGCAAGGCCACACTGACTTCAGACAAATC

CTCCACCACAGCCTACATGGAGCTCAGCAGCCTGACCTCTGAGGACTNTG

CGGTCTATTACTGTGCAAGACTTGATGGTTACTACGACTGCTTTGACTAC

TGGGGCCAAGGCACCACTCTCACAGTCTCNTCAGCCAAAACGACACCCCC

ATCTGTCTATCCACTGGCCCCTGGATCTGCTGCCCAAACTAACTCCATGG

TGACCCTGGGATGCCNGGTCAAGGG
where each N can be A, T, C, or G, as long as the
nucleic acid molecule encodes the amino acid
sequence of SEQ ID NO: 5.

SEQ ID NO: 7 (Amd1.1):
QQSGAELVKPGASVKLSCTASGFNIKDTYIHWVKQRPEQGLEWIGRIDPA

NGITNYDPKFQGRATITADTSSNIAYLQLTSLTSEGTAVYYCARGGYLSP

YAMDYWGQGTSVTVSS

This amino acid sequence is encoded by the
following nucleotide sequence (SEQ ID NO: 8):
NTGCAGCAGTCTGGGGCAGAGCTTGTGAAGCCAGGGGCCTCAGTCAAGTT

GTCCTGCACAGCTTCTGGCTTCAACATTAAAGACACCTATATACATTGGG

TGAAGCAGAGGCCTGAACAGGGCCTGGAGTGGATTGGAAGGATTGATCCT

GCGAATGGTATTACTAATTATGACCCGAAGTTCCAGGGCAGGGCCACTAT

AACAGCAGACACATCCTCCAATATAGCCTACCTGCAGCTCACCAGCCTGA

CATCTGAGGGCACTGCCGTCTACTACTGTGCTAGAGGGGGTTACCTATCC

CCTTATGCTATGGACTACTGGGGTCAAGGAACCTCAGTCACCGTCTCCTC
```

```
AGCCAAAACGACACCCCCATCTGTCTATCCACTGGCCCCTGGATCTGCTG

CCCAAACTAACTCCATGGTGACCCTGGGATGCCTGGTCAAGGGCTATTNC

CCTGAGCCAG
```
where each N can be A, T, C, or G, as long as the
nucleic acid molecule encodes the amino acid
sequence of SEQ ID NO: 7.

SEQ ID NO: 9 (Amd1.5):
QQSGAELVRPGALVKLSCKAS<u>GFNIQDYYLH</u>WMKQRPEQGLEWIGW<u>IDPE</u>

<u>NDNT</u>VYDPKFRDRASLTADTFSNTAYLQLSGLTSEDTAVYYCARR<u>DGITT</u>

<u>ATRAMDY</u>WGQGTSVTVSS

This amino acid sequence is encoded by the
following nucleotide sequence (SEQ ID NO: 10):
```
TGCAGCAGTCTGGGGCTGAGCTTGTGAGGCCAGGGGCCTTAGTCAAATTG

TCCTGCAAAGCTTCTGGCTTCAACATTCAAGACTACTATCTACACTGGAT

GAAACAGAGGCCTGAGCAGGGCCTGGAGTGGATTGGATGGATTGATCCTG

AGAATGATAATACTGTATATGACCCGAAGTTCCGGGACAGGGCCAGTTTA

ACAGCAGACACATTTTCCAACACAGCCTACCTACAGCTCAGCGGCCTGAC

ATCTGAAGACACTGCCGTCTATTACTGTGCTAGAAGAGACGGCATTACTA

CGGCTACGCGGGCTATGGACTACTGGGGTCAAGGAACCTCAGTCACCGTC

TCCTCAGCCAAAACGACACCCCCATCTGTCTATCCACTGGCCCCTGGATC

TGCTGCCCAAACTAACTCCATGGTGACCCTGGGATGCCTGGTCAAGGGCN

NNNNCCTGAGCCAG
```
where each N can be A, T, C, or G, as long as the
nucleic acid molecule encodes the amino acid
sequence of SEQ ID NO: 9.

SEQ ID NO: 11 (Amd1.6):
QSGTVLARPGTSVKMSCKAS<u>GYSFTNYW</u>MHWVRQRPGQGLEWIGS<u>IYPGN</u>

<u>SDTT</u>YNQKFKDKAKLTAVTSASTAYMELSSLTNEDSAVYYCTG<u>DDYSRFS</u>

<u>YW</u>GQGTLVTVSA

This amino acid sequence is encoded by the
following nucleotide sequence (SEQ ID NO: 12):
```
CAGTCTGGGACTGTACTGGCAAGGCCTGGGACTTCCGTGAAGATGTCCTG

CAAGGCTTCTGGCTACAGCTTTACCAACTACTGGATGCACTGGGTAAGAC

AGAGGCCTGGACAGGGTCTAGAATGGATTGGTTCTATTTATCCTGGAAAT

AGTGATACTACCTACAACCAGAAGTTCAAGGACAAGGCCAAACTGACTGC

AGTCACATCCGCCAGCACTGCCTACATGGAGCTCAGCAGCCTGACAAATG

AGGACTCTGCGGTCTATTACTGTACGGGGGATGATTACTCTCGGTTTTCT

TACTGGGGCCAAGGGACTCTGGTCACTGTCTCTGCAGCCAAAACGACACC

CCCATCGTCTATCCACTGGCCCCTGGATCTGCTGCCCAAACTAACTCCA

TGGTGACCCTGGGATGCCTNGTCAAGGGCTNTTTCCCNGAGCCA
```
where each N can be A, T, C, or G, as long as the
nucleic acid molecule encodes the amino acid
sequence of SEQ ID NO: 11.

SEQ ID NO 13: (Amd1.7):
QQSGPELVKPGASVKISCKAS<u>GYTFTDYNMH</u>WVKQSHGKSLEWIGY<u>IFPY</u>

<u>NGDT</u>DYNQKFKNKATLTVDNSSSTAYMDLRSLTSEDSAVYYCSR<u>WGSYFD</u>

<u>YW</u>GQGTTLTVSS

This amino acid sequence is encoded by the
following nucleotide sequence (SEQ ID NO: 14):
```
TGCAGCAGTCAGGACCTGAGCTGGTGAAACCTGGGGCCTCAGTGAAGATA

TCCTGCAAGGCTTCTGGATACACATTCACTGACTACAACATGCACTGGGT

GAAGCAGAGCCATGGAAAGAGCCTTGAGTGGATTGGATATATTTTTCCTT

ACAATGGTGATACTGACTACAACCAGAAATTCAAGAACAAGGCCACATTG

ACTGTAGACAATTCCTCCAGCACAGCCTACATGGACCTCCGCAGCCTGAC

ATCTGAGGACTCTGCAGTCTATTACTGTTCAAGATGGGGTCTTACTTTG

ACTACTGGGGCCAAGGCACCACTCTCACAGTCTCCTCAGCCAAAACGACA

CCCCCATCTGTCTATCCACTGGCCCCTGGATCTGCTGCCCAAACTAACTC

CATGGTGACCCTGGGATGCCTGNGTCAAGGGCT
```
where each N can be A, T, C, or G, as long as the
nucleic acid molecule encodes the amino acid
sequence of SEQ ID NO: 13.

SEQ ID NO: 15 (Amd1.9):
VESGGGLVKPGGSLKLSCAAS<u>GFTFSSYAM</u>SWVRQTPKKSLEWVAS<u>ITSG</u>

<u>GSA</u>YYPDSVKGRFTISRDNARNILNLQMSSLRSEDTAMYYCAR<u>DDGYFDY</u>

WGQGTTLTVSS

This amino acid sequence is encoded by the
following nucleotide sequence (SEQ ID NO: 16):
```
GTGGAGTCTGGGGGAGGCTTAGTGAAGCCTGGAGGGTCCCTGAAACTCTC

CTGTGCAGCCTCTGGATTCACTTTCAGTAGCTATGCCATGTCTTGGGTTC

GCCAGACTCCAAAAAAGAGTCTGGAGTGGGTCGCATCCATTACTAGTGGT

GGTAGCGCCTACTATCCAGACAGTGTGAAGGGCCGATTCACCATCTCCAG

AGATAATGCCAGGAACATCCTGAACCTGCAGATGAGCAGTCTGAGGTCTG

AGGACACGGCCATGTATTACTGTGCAAGAGACGACGGGTACTTTGACTAC

TGGGGCCAAGGCACCACTCTCACAGTCTCCTCAGCCAAAACGACACCCCC

ATCTGTCTATCCACTGGCCCCTGGATCTGCTGCCCAAACTAACTCCATGG

TGACCCTGGGATGCCTGGTCAA
```

SEQ ID NO: 17 (Amd1.11):
QIQLVQSGPELKKPGETVKISCKAS<u>GYTFTNYG</u>MNWVKQAPGKGLEWMGW

<u>INTYTGEP</u>TYADDFKGRFAFSLETSASTAYLLINNLKNEDTATYFCARR<u>D</u>

<u>GYFDAMDY</u>WGQGTSVTVSS

This amino acid sequence is encoded by the
following nucleotide sequence (SEQ ID NO: 18):
```
NNCCTGATGGCAGCTGCCCAAAGTGCCCAAGCACAGATCCAGTTGGTGCA

GTCTGGACCTGAGCTGAAGAAGCCTGGAGAGACAGTCAAGATCTCCTGCA

AGGCTTCTGGGTATACCTTCACAAACTATGGAATGAACTGGGTGAAGCAG

GCTCCAGGAAAGGGTTTAGAGTGGATGGGCTGGATAAACACCTACACTGG

AGAGCCAACTTATGCTGATGACTTCAAGGGACGCTTTGCCTTCTCTTTGG

AAACCTCTGCCAGCACTGCCTATTTGCTGATCAACAACCTCAAAAATGAG

GACACGGCTACATATTTCTGTGCAAGAAGGGATGGTTACTTCGATGCTAT

GGACTACTGGGGTCAAGGAACCTCAGTCACCGTCTCCTCAGCCAAAACGA
```

CACCCCCATCTGTCTATCCACTGGCCCCTGGATCTGCTGCCCAAACTAAC

TCCATGGTGACCCTGGGATGCCTGGTCAAGGG
where each N can be A, T, C, or G, as long as the
nucleic acid molecule encodes the amino acid
sequence of SEQ ID NO: 17.

SEQ ID NO: 19 (Amd1.12):
QQSGAELVRPGTSVKVSCKTS<u>GYAFTNYLI</u>EWVNQRPGQGLEWIGV<u>INPG</u>

<u>SGGT</u>NYNEKFKAKATLTADKSSSTAYMQLSSLTSDDSAVYFCAR<u>SERGYY</u>

<u>GNYGAMDY</u>WGQGTSVTVSS

This amino acid sequence is encoded by the
following nucleotide sequence (SEQ ID NO: 20):
NNGCAGCAGTCTGGAGCTGAGCTGGTAAGGCCTGGGACTTCAGTGAAGGT

GTCCTGCAAGACTTCTGGATACGCCTTCACTAATTACTTGATAGAGTGGG

TAAATCAGAGGCCTGGACAGGGCCTTGAGTGGATTGGGGTGATTAATCCT

GGAAGTGGTGGTACTAACTACAATGAGAAGTTCAAGGCCAAGGCAACACT

GACTGCAGACAAATCCTCCAGCACTGCCTACATGCAGCTCAGCAGCCTGA

CATCTGATGACTCTGCGGTCTATTTCTGTGCAAGATCAGAGCGAGGCTAC

TATGGTAACTACGGAGCTATGGACTACTGGGGTCAAGGAACCTCAGTCAC

CGTCTCCTCAGCCAAAACGACACCCCATCTGTCTATCCACTGGCCCCTG

GATCTGCTGCCCAAACTAACTCCATGGTGACCCTGGGATGCCTGGTCAAG

GGCTATNTCCCTGAGCCAG
where each N can be A, T, C, or G, as long as the
nucleic acid molecule encodes the amino acid
sequence of SEQ ID NO: 19.

SEQ ID NO: 21 (Amd1.13):
QQPGPELVKPGASLKISCKAS<u>GYSFSSSW</u>MNWVKQRPGQGLEWIGR<u>IYPV</u>

<u>DGDT</u>NYNGKFKGKATLTTDKSSSTAYMQLSSLTSVDSAVYFCAR<u>TGPYAM</u>

<u>DY</u>WGRGTSVTVSS

This amino acid sequence is encoded by the
following nucleotide sequence (SEQ ID NO: 22):
NNGCAGCAGCCTGGACCTGAGCTGGTGAAGCCTGGGGCCTCACTGAAGAT

TTCCTGCAAAGCTTCTGGCTACTCATTCAGTTCCTCTTGGATGAACTGGG

TGAAGCAGAGGCCTGGACAGGGTCTTGAGTGGATTGGACGGATTTATCCT

GTAGATGGAGATACTAACTACAATGGGAAGTTCAAGGGCAAGGCCACACT

GACTACAGACAAATCCTCCAGCACAGCCTACATGCAGCTCAGCAGCCTGA

CCTCTGTGGACTCTGCGGTCTATTTCTGTGCAAGAACTGGGCCCTATGCT

ATGGACTACTGGGGTCGAGGAACCTCAGTCACCGTCTCCTCAGCCAAAAC

GACACCCCATCTGTCTATCCACTGGCCCCTGGATCTGCTGCCCAAACTA

ACTCCATGGTGACCCTGGGATGCCTGGTCAAGGG
where each N can be A, T, C, or G, as long as the
nucleic acid molecule encodes the amino acid
sequence of SEQ ID NO: 21.

SEQ ID NO: 23 (Amd1.16):
GAELVRPGSSVKISCKAS<u>GYTFSTYW</u>MNWVKQRPGQGLEWIG<u>QIYPGDGD</u>

<u>T</u>NYNGKFKGKATLTADKSSSTAYMQLSSLTSDDSAVYFCAR<u>SMVTNYYFA</u>

<u>MDY</u>WGQGTSVTVSS

This amino acid sequence is encoded by the
following nucleotide sequence (SEQ ID NO: 24):
GGGGCTGAGCTGGTGAGGCCTGGGTCCTCAGTGAAGATTTCCTGCAAGGC

TTCTGGCTATACATTCAGTACCTACTGGATGAACTGGGTGAAGCAGAGAC

CTGGACAGGGTCTTGAGTGGATTGGACAGATTTATCCTGGAGATGGTGAT

ACTAACTACAATGGAAAATTCAAGGGTAAAGCCACACTGACTGCAGACAA

ATCCTCCAGCACAGCCTACATGCAGCTCAGCAGCCTAACATCTGACGACT

CTGCGGTCTATTTCTGTGCAAGATCGATGGTAACGAACTATTACTTTGCT

ATGGACTACTGGGGTCAAGGAACCTCAGTCACCGTCTCCTCAGCCAAAAC

GACACCCCATCTGTCTATCCACTGGCCCCTGGATCGCTGCCCAAACTAA

CTCCATGGTGACCCTGGGATGCCNGGTCAAGGG
where each N can be A, T, C, or G, as long as the
nucleic acid molecule encodes the amino acid
sequence of SEQ ID NO: 23.

SEQ ID NO: 25 (Amd1.17):
GGLVKPGGSLKLSCAAS<u>GFTFSDYY</u>MYWVRQTPEKKLEWVAT<u>ISDGGSYT</u>

YYPDSVKGRFTISRDNAKNNLYLQMSSLKSEDTAMYYCVR<u>GLLGFDY</u>WGQ

GTTLTVSS

This amino acid sequence is encoded by the
following nucleotide sequence (SEQ ID NO: 26):
GGGGAGGCTTAGTGAAGCCTGGAGGGTCCCTGAAACTCTCCTGTGCAGCC

TCTGGATTCACTTTCAGTGACTATTACATGTATTGGGTTCGCCAGACTCC

GGAAAAGAAACTGGAGTGGGTCGCAACCATTAGTGATGGTGGTAGTTACA

CCTACTATCCAGACAGTGTGAAGGGGCGATTCACCATCTCCAGAGACAAT

GCCAAGAACAACCTGTACCTGCAAATGAGCAGTCTGAAGTCTGAGGACAC

AGCCATGTATTACTGTGTAAGGGGGCTACTGGGTTTTGACTACTGGGGCC

AAGGCACCACTCTCACAGTCTCCTCAGCCAAAACGACACCCCATCTGTC

TATCCACTGGCCCCTGGATCTGCTGCCCAAACTAACTCCATGGTGACCCT

GGGATGCCTGGTCAAGG

SEQ ID NO: 27 (Amd2.1):
GFVKPGGSLKLSCAAS<u>GFTFSSYA</u>MSWVRQTPEMRLEWVAS<u>ISSGGSXTY</u>

YPDSVMGRFTISRDNARNILNLQMSSLRSEDTAMYYCAR<u>VGLYYDYYYSM</u>

<u>DY</u>WGQGTSVTVSS where X can be any amino acid. This amino acid
sequence is encoded by the following nucleotide
sequence (SEQ ID NO: 28):
GGCTTCGTGAAGCCTGGAGGGTCCCTGAAACTCTCCTGTGCAGCCTCTGG

ATTCACTTTCAGTAGCTATGCCATGTCTTGGGTTCGCCAGACTCCAGAGA

TGAGGCTGGAGTGGGTCGCATCCATTAGTAGTGGTGGTAGNNNCACCTAC

TATCCAGACAGTGTGATGGGCCGATTCACCATCTCCAGAGATAATGCCAG

GAACATCCTGAACCTGCAAATGAGCAGTCTGAGGTCTGAGGACACGGCCA

TGTATTACTGTGCAAGAGTGGGTCTCTACTATGATTATTACTATTCTATG

GACTACTGGGGTCAAGGAACCTCAGTCACCGTCCTCAG
where each N can be A, T, C, or G, as long as the
nucleic acid molecule encodes the amino acid
sequence of SEQ ID NO: 27.

SEQ ID NO: 29 (Amd2.2):
ESGPELVKPGASVKISCKAS<u>GYTFTDYN</u>MHWVRQSHGKSLEWIGY<u>IYPY</u>

<u>NGGT</u>GYNQKFKSKATLTVDNSSSTAYMELRSLTSEDSAVYYCAR<u>EDGYY</u>

<u>GYFDY</u>WGQGTTLTGSS

This amino acid sequence is encoded by the following nucleotide sequence (SEQ ID NO: 30):
GAGTCAGGACCTGAGCTGGTGAAACCTGGGGCCTCAGTGAAGATATCCT

GCAAGGCTTCTGGATACACATTCACTGACTATAACATGCACTGGGTGAG

GCAGAGCCATGGAAAGAGCCTTGAGTGGATTGGATATATTTATCCTTAC

AATGGTGGTACTGGCTACAACCAGAAGTTCAAGAGTAAGGCCACATTGA

CTGTAGACAATTCCTCCAGCACAGCCTACATGGAGCTCCGCAGCCTGAC

ATCTGAGGACTCTGCAGTCTATTACTGTGCAAGAGAGGATGGTTACTAC

GGCTACTTTGAGTACTGGGGCCAAGGCACCACTCTCACAGGCTCCTCAG

SEQ ID NO: 31 (Amd2.4):
QIQLVQSGPELKKPGETVKISCKAS<u>GYTFTNYG</u>MNWVKQAPGKGLKWMG

<u>WINTYTGEP</u>TYADDFKGRFAFSLETSASAAYLQINNLKNEDTATYFCAR

<u>DYDGYYYYAMDY</u>WGQGTSVTVSS

This amino acid sequence is encoded by the following nucleotide sequence (SEQ ID NO: 32):
CAGATCCAGTTGGTGCAGTCTGGACCTGAGCTGAAGAAGCCTGGAGAGA

CAGTCAAGATCTCCTGCAAGGCTTCTGGGTATACCTTCACAAACTATGG

AATGAACTGGGTGAAGCAGGCTCCAGGAAAGGGTTTAAAGTGGATGGGC

TGGATAAACACCTACACTGGAGAGCCAACATATGCTGATGACTTCAAGG

GACGGTTTGCCTTCTCTTTGGAAACCTCTGCCAGCGCTGCCTATTTGCA

GATCAACAACCTCAAAAATGAGGACACGGCTACATATTTCTGTGCAAGG

GACTATGATGGTTACTATTACTATGCCTACTCGGGTCAAGGAACCTCAG

TCACCGTCTCTCATATACG

According to one embodiment, the monoclonal antibody or binding portion comprises a V$_L$ domain comprising one of the following amino acid sequences (CDR domains underlined):

SEQ ID NO: 33 (Amd1.1):
ENVLTQSPAIMSASLGEKVTMTCRAS<u>SSVNY</u>MFWFQQKSDASPKLWIY<u>YTS</u>NLAPGVPARFSGS

GSGNSYSLTISSMEGEDAATYYCQEFTSFPYTFG

This amino acid sequence is encoded by the following nucleotide sequence (SEQ ID NO: 34):
NTCAGTGTCTCAGTTGTAATGTCCAGAGGAGAAAATGTGCTCACCCAGTCTCCAGCAATCATGT

CTGCATCTCTAGGGGAGAAGGTCACCATGACCTGCAGGGCCAGCTCAAGTGTAAATTACATGTT

CTGGTTCCAGCAGAAGTCAGATGCCTCCCCCAAATTGTGGATTTATTATACATCCAACCTGGCT

CCTGGAGTCCCAGCTCGCTTCAGTGGCAGTGGGTCTGGGAACTCTTATTCTCTCACAATCAGCA

GCATGGAGGGTGAAGATGCTGCCACTTATTACTGCCAGGAGTTTACTAGTTTCCCGTACACGTT

CGGA
where each N can be A, T, C, or G, as long as the nucleic acid molecule encodes the amino acid sequence of SEQ ID NO: 33.

SEQ ID NO: 35 (Amd1.2):
DIVLTQSPATLSVTPGDSVSLSCRAS<u>QSISNN</u>LHWYQQKSHESPRLLIK<u>YAS</u>QSISGIPSRFSG

SGSGTDFTLSINSVETEDFGMYFCQQSNSWPQYTF

This amino acid sequence is encoded by the following nucleotide sequence (SEQ ID NO: 36):
TTATGCTTTTTTGGATTTCAGCCTCCAGAGGTGATATTGTGCTAACTCAGTCTCCAGCCACCCT

GTCTGTGACTCCAGGAGATAGCGTCAGTCTTTCCTGCAGGGCCAGCCAAAGTATTAGCAACAAC

CTACACTGGTATCAACAAAAATCACATGAGTCTCCAAGGCTTCTCATCAAGTATGCTTCCCAGT

CCATCTCTGGGATCCCCTCCAGGTTCAGTGGCAGTGGATCAGGGACAGATTTCACTCTCAGTAT

CAACAGTGTGGAGACTGAAGATTTTGGAATGTATTTCTGTCAACAGAGTAACAGCTGGCCTCAG

TACACGTTCGG

SEQ ID NO: 37 (Amd1.6):
SIVMTQTPKFLLVSAGDRLTITCKAS<u>QSVSND</u>VAWYQQKPGQSPKLLIY<u>YTS</u>NRYTGVPDRFTG

SGYGTDFTFTISTVQAEDLAVYFCQQDYNSPWTFGGGTK

This amino acid sequence is encoded by the following nucleotide sequence (SEQ ID NO: 38):
CCAGGTCTTCGTATTTCTACTGCTCTGTGTGTCTGGTGCTCATGGGAGTATTGTGATGACCCAG

ACTCCCAAATTCCTGCTTGTATCAGCAGGAGACAGGCTTACCATAACCTGCAAGGCCAGTCAGA

GTGTGAGTAATGATGTAGCTTGGTACCAACAGAAGCCAGGGCAGTCTCCTAAACTGCTGATATA

CTATACATCCAATCGCTACACTGGAGTCCCTGATCGCTTCACTGGCAGTGGATATGGGACGGAT

TTCACTTTCACCATCAGCACTGTGCAGGCTGAAGACCTGGCAGTTTATTTCTGTCAGCAGGATT

ATAACTCTCCGTGGACGTTCGGTGGAGGCACCAAG

SEQ ID NO: 39 (Amd1.7):
SIVMTQTPKFLLVSAGDRLTITCKAS<u>QSVSND</u>VAWYQQKPGQSPKLLIY<u>YTS</u>NRYTGVPDRFTG

SGYGTDFTFTISTVQAEDLAVYFCQQDYNSPWTFGGGTK

This amino acid sequence is encoded by the following nucleotide sequence (SEQ ID NO: 40):
TGGTGCTCATGGGAGTATTGTGATGACCCAGACTCCCAAATTCCTGCTTGTATCAGCAGGAGAC

AGGCTTACCATAACCTGCAAGGCCAGTCAGAGTGTGAGTAATGATGTAGCTTGGTACCAACAGA

AGCCAGGGCAGTCTCCTAAACTGCTGATATACTATACATCCAATCGCTACACTGGAGTCCCTGA

TCGCTTCACTGGCAGTGGATATGGGACGGATTTCACTTTCACCATCAGCACTGTGCAGGCTGAA

GACCTGGCAGTTTATTTCTGTCAGCAGGATTATAACTCTCCGTGGACGTTCGGTGGAGGCACCA

AGC

SEQ ID NO: 41 (Amd1.8):
DIVMTQSPATLSVTPGDRVSLSCRAS<u>QSISDY</u>LHWYQQRSHESPRLLIK<u>YVS</u>QSISGIPSRFSG

SGSGSDFTLSINSVEPEDVGVYYCQNGHSFPYTFG

This amino acid sequence is encoded by the following nucleotide sequence (SEQ ID NO: 42):
CTTGGACTTTTGCTTTTCTGGACTTCAGCCTCCAGATGTGACATTGTGATGACTCAGTCTCCAG

CCACCCTGTCTGTGACTCCAGGAGATAGAGTCTCTCTTTCCTGCAGGGCCAGCCAGAGTATTAG

CGACTACTTACACTGGTATCAACAAAGATCACATGAGTCTCCAAGGCTTCTCATCAAATATGTT

TCCCAATCCATCTCTGGGATCCCCTCCAGGTTCAGTGGCAGTGGATCAGGGTCAGATTTCACTC

TCAGTATCAACAGTGTGGAACCTGAAGATGTTGGAGTGTATTATTGTCAAAATGGTCACAGCTT

TCCGTACACGTTCGGA

SEQ ID NO: 43 (Amd1.9):
DIQMTQSPASLSVSVGETVTITCRTS<u>ENIFSN</u>FAWYQQQPGKSPQLLVY<u>GAT</u>NLADGVPSRFSG

SGSGTQYSLKITSLQSEDFGSYYCQHFWGSPWTF

This amino acid sequence is encoded by the following nucleotide sequence (SEQ ID NO: 44):
TTACAGATGCCAGATGTGACATCCAGATGACTCAGTCTCCAGCCTCCCTATCTGTATCTGTGGG

AGAAACTGTCACCATCACATGTCGAACAAGTGAAAATATTTTCAGTAATTTCGCATGGTATCAG

CAGCAACCGGGAAAATCTCCTCAGCTCCTGGTCTATGGTGCAACAAACTTAGCAGATGGTGTGC

CATCAAGGTTCAGTCGCAGTGGATCAGGCACACAGTATTCCCTCAAGATCACCAGCCTGCAGTC

TGAAGATTTTGGGAGTTATTACTGTCAACATTTTTGGGGTAGTCCGTGGACGTTCGG

SEQ ID NO: 45 (Amd1.10):
QIVLTQSPALMSASPGEKVTMTCSAS<u>SSVSY</u>MYWYQQKPRSSPKPWIY<u>LTS</u>NLASGVPARFSGS

GSGTSYSLTISSMEAEDAATYYCQQWSSNPPYTFG

This amino acid sequence is encoded by the following nucleotide sequence (SEQ ID NO: 46):
TCAGTGCCTCAGTCATAATGTCCAGGGGACAAATTGTTCTCACCCAGTCTCCAGCACTCATGTC

TGCATCTCCAGGGGAGAAGGTCACCATGACCTGCAGTGCCAGCTCAAGTGTAAGTTACATGTAC

TGGTACCAGCAGAAGCCAAGATCCTCCCCCAAACCCTGGATTTATCTCACATCCAACCTGGCTT

CTGGAGTCCCTGCTCGCTTCAGTGGCAGTGGGTCTGGGACCTCTTACTCTCTCACAATCAGCAG

CATGGAGGCTGAAGATGCTGCCACTTATTACTGCCAGCAGTGGAGTAGTAACCCACCCTACACG

TTCGGA

SEQ ID NO: 47 (Amd1.11):
DILLTQSPAILSVSPGERVSFSCRAS<u>QSIGTS</u>IHWYQQRTNGSPRLLIK<u>YAS</u>ESISGIPSRFSG

SGSGTDFTLSINSVESEDIADYYCQQSNSWPALTFG

This amino acid sequence is encoded by the following nucleotide sequence (SEQ ID NO: 48):
GGACTTTTGCTTTTCTGGATTCCAGCCTCCAGAGGTGACATCTTGCTGACTCAGTCTCCAGCCA

TCCTGTCTGTGAGTCCAGGAGAAAGAGTCAGTTTCTCCTGCAGGGCCAGTCAGAGCATTGGCAC

AAGCATACACTGGTATCAACAAAGAACAAATGGTTCTCCAAGGCTTCTCATAAAGTATGCTTCT

GAGTCTATCTCTGGGATCCCTTCCAGGTTTAGTGGCAGTGGATCAGGGACAGATTTTACTCTTA

GCATCAACAGTGTGGAGTCTGAAGATATTGCAGATTATTACTGTCAACAAAGTAATAGCTGGCC

AGCGCTCACGTTCGGT

SEQ ID NO: 49 (Amd1.12):
DIQMTQSPASLSASVGDTVTITCRAS<u>ENIYSY</u>LAWYQQKQGKSPQLLVY<u>NAK</u>TFAEGVRSRFSG

SGSGTQFSLQITSLQPEDFGSYYCQHHYGSPYTF

This amino acid sequence is encoded by the following nucleotide sequence (SEQ ID NO: 50):
TCTGCTGCTGTGGCTTACAGGTGCCAGATGTGACATCCAGATGACTCAGTCTCCAGCCTCCCTA

TCTGCATCTGTGGGAGATACTGTCACCATCACATCTCGAGCAAGTGAGAATATTTACAGTTATT

TAGCATGGTATCACCAGAAACAGGGAAAATCTCCTCAGCTCCTGGTCTATAATGCAAAAACCTT

CGCAGAAGGTGTGCGATCAAGGTTCAGTGGCAGTGGATCAGGCACACAGTTTTCTCTGCAGATC

ACCAGCCTGCAGCCTGAAGATTTTGGGAGTTATTACTGTCAACATCATTATGGTTCTCCGTACA

CGTTCGG

SEQ ID NO: 51 (Amd1.13):
DIVMTQSPSSLTVTAGEKVTMSCKSS<u>QSLLNSGNQKNYL</u>TWYQQKPGQPPKLLIS<u>WAS</u>TRESGV

PDRFTGSGSGTDFTLTISSVQAEDLAVYYCQNDYSYPFTFG

This amino acid sequence is encoded by the following nucleotide sequence (SEQ ID NO: 52):
GGTACCTGTGGGACATTGTGATGACGCAGTCTCCATCCTCCCTGACTGTGACAGCAGGAGAGA

AGGTCACTATGAGGTGCAAGTCCAGTCAGAGTCTGTTAAACAGTGGAAATCAAAAAAACTACTT

GACCTGGTACCAGCAGAAACCAGGGCAGCCTCCTAAACTGTTGATCTCCTGGGCATCCACTAGG

GAATCTGGGGTCCCTGATCGCTTCACAGGCAGTGGATCTGGAACAGATTTCACTCTCACCATCA

GCAGTGTGCAGGCTGAAGACCTGGCAGTTTATTACTGTCAGAATGACTATAGTTATCCATTCAC

GTTCGGC

SEQ ID NO: 53 (Amd1.15):
DIAMTQSHKFMSTSVGDRVSITCKAS<u>QDVSTA</u>VAWYQQKPGQSPKLLIY<u>SAS</u>YRYTGVRDRFXG

SRCGTDFTFPISSVQGEDLAVYYCQQHYSIHSRS where X can be any amino acid. This amino acid sequence is encoded by the following
nucleotide sequence (SEQ ID NO: 54):
NCTGCTATTCTGCTATGGGTATCTGGTGTTGACGGAGACATTGCGATGACCCAGTCTCACAAAT

TCATGTCCACATCAGTAGGAGACAGGGTCAGCATCACCTGCAAGGCCAGTCAGGATGTGAGTAC

TGCTGTAGCCTGGTATCAACAGAAACCAGGACAATCTCCTAAACTACTGATTTACTCGGCATCC

TACCGGTACACTGGAGTCCGTGATCGCTTCANTGGCAGTCGATGTGGGACGGATTTCACTTTCC

CCATCAGCAGTGTGCAGGGTGAAGACCTGGCAGTTTATTACTGTCAGCAACATTATAGTATCCA

TTCACGTTCGG
where each N can be A, T, C, or G, as long as the nucleic acid molecule encodes the
amino acid sequence of SEQ ID NO: 53.

SEQ ID NO: 55 (Amd1.17):
DVLMTQTPLSLPVSLGDQASISCRSS<u>QSIVHSNGNTY</u>LEWYLQKPGQSPKLLIY<u>RVS</u>NRFSGVP

DRFSGSGSGTDFTLKISRVEAEDLGVYYCFQGSHVPWTFGGGT

-continued

This amino acid sequence is encoded by the following nucleotide sequence (SEQ ID NO: 56):
TGGATCCCTGCTTCCAGCAGTGATGTTTTGATGACCCAAACTCCACTCTCCCTGCCTGTCAGTC

TTGGAGATCAAGCCTCCATCTCTTGCAGATCTAGTCAGAGCATTGTACATAGTAATGGAAACAC

CTATTTAGAATGGTACCTGCAGAAACCAGGCCAGTCTCCAAAGCTCCTGATCTACAGAGTTTCC

AACCGATTTTCTGGGGTCCCAGACAGGTTCAGTGGCAGTGGATCAGGGACAGATTTCACACTCA

AGATCAGCAGAGTGGAGGCTGAGGATCTGGGAGTTTATTACTGCTTTCAAGGTTCACATGTTCC

GTGGACGTTCGGTGGAGGCACCAA

SEQ ID NO: 57 (Amd 2.1):
DIVMTQSPSSLTVTAGEKVTMSCKSSQSLLYSGNQKNYLTWYQQKPGQPPKMLIYWASTRESGV

PDRFTGSGSGTHFTLTISSVQAEDLAIYYDQNDYSYPVTFGAGTKLELK

This amino acid sequence is encoded by the following nucleotide sequence (SEQ ID NO: 58):
GACATTGTGATGACACAGTCTCCATCCTCCCTGACTGTGACAGCAGGAGAGAAGGTCACTATGA

GCTGCAAGTCCAGTCAGAGTCTGTTATACAGTGGAAATCAAAAGAACTACTTGACCTGGTACCA

GCAGAAACCAGGGCAGCCTCCTAAAATGTTGATCTACTGGGCATCCACTAGGGAATCTGGGGTC

CCTGATCGCTTCACAGGCAGTGGATCTGGAACACATTTCACTCTCACCATCAGCAGTGTGCAGG

CTGAAGACCTGGCAATTTATTACTGTCAGAATGATTATAGTTATCCGGTCACGTTCGGTGCTGG

GACCAAGCTGGAGCTGAAAC

SEQ ID NO: 59 (Amd 2.2):
EIVLTQSPAITAASLGQKVTITCSASSSVNYMHWYQQKSGTSPKPWIYEISKLASGVPARFSGS

GSGTSYSLTISSMEAEDAAIYYCQQWNYPLITFGAGTKLELK

This amino acid sequence is encoded by the following nucleotide sequence (SEQ ID NO: 60):
GAAATTGTGCTCACTCAGTCTCCAGCCATCACAGCTGCATCTCTGGGGCAAAAGGTCACCATCA

CCTGCAGTGCCAGCTCAAGTGTAAATTACATGCACTGGTACCAGCAGAAGTCAGGCACCTCCCC

CAAACCATGGATTTATGAAATATCCAAACTGGCTTCTGGAGTCCCAGCTCGCTTCAGTGGCAGT

GGGTCTGGGACCTCTTACTCTCTCACAATCAGCAGCATGGAGGCTGAAGATGCTGCCATTTATT

ACTGCCAGCAGTGGAATTATCCTCTTATCACGTTCGGTGCTGGGACCAAGCTGGAGCTGAAAC

SEQ ID NO: 61 (Amd 2.4):
ENALTQSPAIMSASPGEKVTMTCSASSSVSYMHWYQQKSSMSPKLWIYDTSKLASGVPGRFSGS

GSGNSYSLTISSMEAEEVATYYCFQGSGFPVHVRRGDQVGNKT

This amino acid sequence is encoded by the following nucleotide sequence (SEQ ID NO: 62):
GAAAATGCTCTCACCCAGTCTCCAGCAATCATGTCTGCATCTCCAGGGGAAAAGGTCACCATGA

CCTGCAGTGCCAGCTCAAGTGTAAGTTACATGCACTGGTACCAGCAGAAGTCAAGCATGTCCCC

CAAACTCTGGATTTATGACACATCCAAACTGGCTTCTGGAGTCCCAGGTCGCTTCAGTGGCAGT

GGGTCTGGAAACTCTTACTCTCTCACGATCAGCAGCATGGAGGCTGAAGAGGTTGCCACTTATT

ACTGTTTTCAGGGGtAGTGGGTTCCCAGTACACGTTCGGAGGGGGGACCAAGTTGGAAATAAAA

C

SEQ ID NO: 63 (Amd 2.5):
DIQMTQSPASLSASVGETITITCRASGNIHNYLAWYQQKQGKSPHLLVFHARSLADGVPSRFSG

SGSGTQYSLNINSLQPEDFGIYYCQHFWYTPYTFGGGTKLEIK

This amino acid sequence is encoded by the following nucleotide sequence (SEQ ID NO: 64):
GACATCCAGATGACTCAGTCTCCAGCCTCCCTATCTGCATCTGTGGGAGAAACTATCACCATCA

CATGTCGAGCAAGTGGGAATATTCACAATTATTTAGCATGGTATCAGCAGAAACAGGGAAAATC

TCCTCACCTCCTGGTCTTTCATGCAAGATCCTTAGCAGATGGTGTGCCATCAAGGTTCAGTGGC

-continued

```
AGTGGATCAGGAACACAATATTCTCTCAATATCAACAGCCTGCAGCCTGAAGATTTTGGGATTT

ATTACTGTCAACATTTTTGGTATACTCCGTACACGTTCGGAGGGGGGACCAAGCTGGAAATAAA

AC
```

Also encompassed by this disclosure are Amd antibodies, and Amd binding portions thereof, that bind to the same epitope of Amd as one or more of the disclosed anti-Amd antibodies. Additional antibodies and Amd binding antibody portions can therefore be identified based on their ability to cross-compete (e.g., to competitively inhibit the binding of, in a statistically significant manner) with the disclosed antibodies in Amd binding assays. The ability of a test antibody to inhibit the binding of an anti-Amd reference antibody disclosed herein to an Amd protein (e.g., an Amd protein or polypeptide having at least part of the sequence of SEQ ID NO:1, such as the catalytic domain or amino acids 9-252 of SEQ ID NO: 1 or the cell wall binding domain) demonstrates that the test antibody can compete with the reference antibody for binding to Amd. Such an antibody may, according to non-limiting theory, bind to the same or a related (e.g., a structurally similar or spatially proximal) epitope on the Amd protein as the reference antibody with which it competes. In certain embodiments, the antibody that binds to the same epitope on Amd as a reference antibody disclosed herein is a humanized antibody. In certain embodiments, the antibody that binds to the same epitope on Amd as a reference antibody disclosed herein is a human antibody. The Amd-binding antibodies and Amd binding antibody portions can also be other mouse or chimeric Amd-binding antibodies and Amd binding antibody portions which bind to the same epitope as the reference antibody.

The capacity to block or compete with the reference antibody binding indicates that an Amd-binding test antibody or Amd-binding antibody portion binds to the same or similar epitope as that defined by the reference antibody, or to an epitope which is sufficiently proximal to the epitope bound by the reference Amd-binding antibody. Such antibodies are especially likely to share the advantageous properties identified for the reference antibody.

The capacity to block or compete with the reference antibody may be determined using techniques known in the art such as a competition binding assay. With a competition binding assay, the antibody or Amd-binding antibody portion under test is examined for ability to inhibit specific binding of the reference antibody to an Amd protein or a portion of an Amd protein (e.g., the catalytic domain or amino acids 9-252 of SEQ ID NO: 1, or the cell wall binding domain). A test antibody competes with the reference antibody fir specific binding to the Amd protein or portion thereof, as antigen, if an excess of the test antibody substantially inhibits binding of the reference antibody. Substantial inhibition means that the test antibody reduces specific binding of the reference antibody usually by at least 10%, 25%, 50%, 75%, or 90%.

Known competition binding assays can be generally applied or routinely adapted to assess competition of an Amd-binding antibody or Amd-binding antibody portion with the reference Amd-binding antibody for binding to an Amd protein or portion thereof. Such competition binding assays include, but are not limited to solid phase direct or indirect radioimmunoassay (RIA), solid phase direct or indirect enzyme immunoassay (HA), sandwich competition assay (see Stähli et al., "Distinction of Epitopes by Monoclonal Antibodies," *Methods in Enzymology* 92:242-253, (1983), which is hereby incorporated by reference in its entirety); solid phase direct biotin-avidin EIA (see Kirkland et al., "Analysis of the Fine Specificity and Cross-reactivity of Monoclonal Anti-lipid A Antibodies," *J. Immunol*. 137: 3614-3619 (1986), which is hereby incorporated by reference in its entirety); solid phase direct labeled assay, solid phase direct labeled sandwich assay (Ed Harlow and David Lane, USING ANTIBODIES: A LABORATORY MANUAL (Cold Spring Harbor Laboratory Press, 1999), which is hereby incorporated by reference in its entirety); solid phase direct label RIA using I-125 label (see Morel et al., "Monoclonal Antibodies to Bovine Serum Albumin: Affinity and Specificity Determinations," *Molec. Immunol*. 25:7-15 (1988), which is hereby incorporated by reference in its entirety); solid phase direct biotin-avidin EIA (Cheung et al., "Epitope-Specific Antibody Response to the Surface. Antigen of Duck Hepatitis B Virus in Infected Ducks," *Virology* 176:546-552 (1990), which is hereby incorporated by reference in its entirety); and direct labeled RIA (Moldenhauer et al., "Identity of HML-1 Antigen on Intestinal Intraepithelial T Cells and of B-1y7 Antigen on Hairy Cell Leukaemia," *Scand. J. Immunol*. 32:77-82 (1990), which is hereby incorporated by reference in its entirety). Typically, such an assay involves the use of purified antigen bound to a solid surface or cells bearing either of these, an unlabeled test Amd-binding antibody and a labeled reference antibody. Competitive inhibition is measured by determining the amount of label bound to the solid surface or cells in the presence of the test antibody. Usually the test antibody is present in excess. Antibodies and antigen binding antibody portions identified by competition assay (competing antibodies) include antibodies and antigen binding antibody portions that bind to the same epitope as the reference antibody and antibodies binding to an adjacent epitope sufficiently proximal to the epitope bound by the reference antibody for steric hindrance to occur.

In some embodiments, the antibody, or Amd binding portion thereof, binds specifically to Amd and cross competes with an anti-Amd antibody described herein. In further embodiments, the antibody, or Amd binding portion thereof, binds specifically to Amd and cross competes with an anti-Amd antibody selected from Amd1.1, Amd1.2, Amd1.5, Amd1.6, Amd1.7, Amd1.8, Amd1.9, Amd1.10, Amd1.11, Amd1.12, Amd1.13, Amd1.14, Amd1.15, Amd1.16, Amd1.17, Amd2.1, Amd2.2, Amd2.4, and Amd2.5. In particular embodiments, the antibody, or Amd binding portion thereof, binds specifically to Amd and cross competes with antibody Amd1.6. In other embodiments, the antibody, or Amd binding portion thereof, binds specifically to Amd and cross competes with antibody Amd2.1. In further embodiments, the antibody, or Amd binding portion thereof, binds specifically to Amd, cross competes with one or more of the above anti-Amd antibodies, and inhibits Amd catalytic activity.

In additional embodiments, the antibody, or Amd binding portion thereof, binds to the same epitope as an antibody described herein. In further embodiments, the antibody, or Amd binding portion thereof, binds to the same epitope as an antibody selected from Amd1.1, Amd1.2, Amd1.5, Amd1.6, Amd1.7, Amd1.8, Amd1.9, Amd1.10, Amd1.11, Amd1.12, Amd 1.13, Amd 1.14, Amd 1.15, Amd 1.16, Amd 1.17, Amd2.1, Amd2.2, Amd2.4, and Amd2.5. In particular embodiments, the antibody, or Amd binding portion thereof, binds to the same epitope as antibody Amd1.6. In other embodiments, the antibody, or Amd binding portion thereof, binds to the same epitope as antibody Amd2.1. In further embodiments, the antibody, or Amd binding portion thereof, binds to the same epitope as one or more of the above anti-Amd antibodies and inhibits Amd catalytic activity.

In some embodiments, the antibody, or Amd binding portion thereof, binds specifically to Amd and cross competes with an anti-Amd antibody that binds a *Staphylococcus* spp. Amd catalytic domain. In further embodiments, the antibody, or Amd binding portion thereof, binds specifically to Amd and cross competes with an anti-Amd antibody selected from Amd 1.6, Amd 1.10, Amd 1.13, Amd 1.16, Amd 1.17, Amd2.1, and Amd2.2. In further embodiments, the antibody, or Amd binding portion thereof, binds specifically to Amd, cross competes with one or more of the above-identified anti-Amd antibodies, and inhibits Amd catalytic activity.

In additional embodiments, the antibody, or Amd binding portion thereof, binds to the same epitope of an Amd catalytic domain as an antibody described herein. In further embodiments, the antibody, or Amd binding portion thereof, binds to the same epitope of an Amd catalytic domain as an antibody selected from Amd1.6, Amd1.10, Amd1.13, Amd1.16, Amd1.17, Amd2.1, and Amd2.2. In further embodiments, the antibody, or Amd binding portion thereof, binds to the same epitope as one or more of the above-identified anti-Amd antibodies and inhibits Amd catalytic activity.

In some embodiments, the antibody, or Amd binding portion thereof, binds specifically to Amd and cross competes with an anti-Amd antibody that binds a *Staphylococcus* spp. Amd cell wall binding domain. In additional embodiments, the antibody, or Amd binding portion thereof, binds specifically to Amd and cross competes with an anti-Amd antibody described herein that binds a cell wall binding domain. In further embodiments, the antibody, or Amd binding portion thereof, binds specifically to Amd and cross competes with an antibody selected from Amd1.1, Amd1.2, Amd1.5, Amd1.7, Amd1.8, Amd1.9, Amd 1.11, Amd1.12, Amd 1.14, Amd 1.15, Amd2.4, and Amd2.5.

In some embodiments, the antibody, or Amd binding portion thereof, binds to the same epitope of an Amd cell wall binding domain as an anti-Amd antibody described herein. In further embodiments, the antibody, or Amd binding portion thereof, binds to the same epitope of an Amd cell wall binding domain as an antibody selected from Amd1.1, Amd1.2, Amd1.5, Amd1.7, Amd1.8, Amd1.9, Amd 1.11, Amd1.12, Amd1.14, Amd1.15, Amd2.4, and Amd2.5.

Antibodies disclosed herein may also be synthetic antibodies. A synthetic antibody is an antibody which is generated using recombinant DNA technology, such as, for example, an antibody expressed by a bacteriophage. Alternatively, the synthetic antibody is generated by the synthesis of a DNA molecule encoding the antibody, followed by the expression of the antibody (i.e., synthesis of the amino acid specifying the antibody) where the DNA or amino acid sequence has been obtained using synthetic DNA or amino acid sequence technology which is available and well known in the art.

In certain embodiments, the synthetic antibody is generated using one or more of the CDRs of a heavy chain variable domain as identified above, combinations of CDRs from different heavy chain variable domains as identified above, one or more of the CDRs of a light chain variable domain as identified, or combinations of CDRs from different light chain variable domains as identified above. By way of example, Amd1.6 and Amd2.1 include the following CDRs:

| Source & CDR | Sequence | SEQ ID NO: |
|---|---|---|
| Amd1.6 $V_H$, CDR1 | GYSFTNYW | 65 |
| Amd1.6 $V_H$, CDR2 | IYPGNSDT | 66 |
| Amd1.6 $V_H$, CDR3 | DDYSRFSY | 67 |
| Amd1.6 $V_L$, CDR1 | QSVSND | 68 |
| Amd1.6 $V_L$, CDR2 | YTS | 69 |
| Amd2.1 $V_H$, CDR1 | GFIFSSYA | 70 |
| Amd2.1 $V_H$, CDR2 | ISSGGSKT | 71 |
| Amd2.1 $V_H$, CDR3 | VGLYYDYYYSMDY | 72 |
| Amd2.1 $V_L$, CDR1 | QSILLYSGNQKNY | 73 |
| Amd2.1 $V_L$, CDR2 | WAS | 74 |

In Amd2.1 $V_H$, CDR2 (SEQ ID NO: 71), X can be any amino acid.

In one embodiment, the monoclonal antibody or binding portion is partially humanized or fully human.

Humanized antibodies are antibodies that contain minimal sequences from non-human (e.g. murine) antibodies within the variable regions. Such antibodies are used therapeutically to reduce antigenicity and human anti-mouse antibody responses when administered to a human subject. In practice, humanized antibodies are typically human antibodies with minimum to no non-human sequences. A human antibody is an antibody produced by a human or an antibody having an amino acid sequence corresponding to an antibody produced by a human.

An antibody can be humanized by substituting the complementarity determining region (CDR) of a human antibody with that of a non-human antibody (e.g. mouse, rat, rabbit, hamster, etc.) having the desired specificity, affinity, and capability (Jones et al., "Replacing the Complementarity-Determining Regions in a Human Antibody With Those From a Mouse," *Nature* 321:522-525 (1986); Riechmann et al., "Reshaping Human Antibodies for Therapy," *Nature* 332:323-327 (1988); Verhoeyen et al., "Reshaping Human Antibodies: Grafting an Antilysozyme Activity," *Science* 239:1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

Humanized antibodies can be produced using various techniques known in the art. Immortalized human B lymphocytes immunized in vitro or isolated from an immunized individual that produce an antibody directed against a target antigen can be generated (see e.g. Reisfeld et al., MONOCLONAL ANTIBODIES AND CANCER THERAPY 77 (Alan R. Liss ed., 1985) and U.S. Pat. No. 5,750,373 to Garrard, which are hereby incorporated by reference in their entirety). Also, the humanized antibody can be selected from a phage library, where that phage library expresses human antibodies (Vaughan et al., "Human Antibodies with Sub-Nanomolar Affinities Isolated from a Large Non-immunized Phage Display Library," *Nature Biotechnology*, 14:309-314 (1996); Sheets et al., "Efficient Construction of a Large Nonimmune Phage Antibody Library: The Production of High-Affinity Human Single-Chain Antibodies to Protein Antigens," *Proc. Nat'l. Acad. Sci. U.S.A.* 95:6157-6162 (1998); Hoogenboom et al., "By-passing Immunisation. Human Antibodies from Synthetic Repertoires of Germline VH Gene Segments Rearranged in vitro," *J. Mol. Biol.* 227:381-8 (1992); Marks et al., "By-passing Immunization. Human Antibodies from V-gene Libraries Displayed on Phage," *J. Mol. Biol.* 222: 581-97 (1991), which are hereby incorporated by reference in their entirety). Humanized antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety.

In certain embodiments, the humanized monoclonal antibody is IgG1, IgG2, IgG3 class or IgG4 class. The IgG3 class is particularly preferred because of its diminished Protein A binding (see Natsume et al., "Engineered Antibodies of IgG1/IgG3 Mixed Isotype with Enhanced Cytotoxic Activities," *Cancer Res* 68(10):3863-72 (2008), which is hereby incorporated by reference in its entirety).

Circulating half-life of these antibody classes can be enhanced with modifications to the Fc domains, such as the N434A and T307A/E380A/N434A substitutions described by Petkova et al. ("Enhanced Half-life of Genetically Engineered Human IgG1 Antibodies in a Humanized FcRn Mouse Model: Potential Application in Humorally Mediated Autoimmune Disease," *International Immunology* 18(12): 1759-1769 (2006), which is hereby incorporated by reference in its entirety) or the N297Q substitution described by Balsitis et al. ("Lethal Antibody Enhancement of Dengue Disease in Mice Is Prevented by Fc Modification," *PloS Pathogens* 6(2): e1000790 (2010), which is hereby incorporated by reference in its entirety).

The heavy and light chain sequences identified above as SEQ ID NOS: 5, 7, 9, 11, 13, 15, 17, 19, 21, 23, 25, 27, 29, 31, 33, 35, 37, 39, 41, 43, 45, 47, 49, 51, 53, 55, 57, 59, 61, and 63, respectively, can be used to identify codon-optimized DNA sequences, which can be introduced into suitable expression systems for the production of recombinant, chimeric antibodies in accordance with the present invention. Alternatively, the DNA sequences identified above can be used for the preparation of suitable expression systems for the production of recombinant, chimeric antibodies in accordance with the present invention.

In addition to whole antibodies, the present invention encompasses Amd binding portions of such antibodies. Such Amd binding portions include, without limitation, the monovalent Fab fragments, Fv fragments (e.g., single-chain antibody, scFv), single variable $V_H$ and $V_L$ domains, and the bivalent F(ab')$_2$ fragments, Bis-scFv, diabodies, triabodies, and minibodies. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983); Ed Harlow and David Lane, ANTIBODIES: A LABORATORY MANUAL (Cold Spring Harbor Laboratory, 1988); Houston et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA* 85:5879-5883 (1988); Bird et al, "Single-Chain Antigen-Binding Proteins," *Science* 242:423-426 (1988), which are hereby incorporated by reference in their entirety, or other methods known in the art.

In some embodiments, the antibody, or Amd binding portion thereof, comprises a framework in which amino acids have been substituted into the antibody framework from the respective human $V_H$ or $V_L$ germline sequences. Example 6, infra, identifies germline sequences for a number of antibodies described herein.

It may further be desirable, especially in the case of antibody fragments, to modify the antibody to increase its serum half-life. This can be achieved, for example, by incorporation of a salvage receptor binding epitope into the antibody fragment by mutation of the appropriate region in the antibody fragment or by incorporating the epitope binding site into a peptide tag that is then fused to the antibody fragment at either end or in the middle (e.g., by DNA or peptide synthesis).

Antibody mimics are also suitable for use in accordance with the present invention. A number of antibody mimics are known in the art including, without limitation, those known as adnectins or monobodies, which are derived from the tenth human fibronectin type III domain ($^{10}$Fn3) (Koide et al., "The Fibronectin Type III Domain as a Scaffold for Novel Binding Proteins," *J. Mol. Biol.* 284:1141-1151 (1998); Koide et al., "Probing Protein Conformational Changes in Living Cells by Using Designer Binding Proteins: Application to the Estrogen Receptor," *Proc. Natl. Acad. Sci. USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol.* 15(8):772-777 (1997), which is hereby incorporated by reference in its entirety).

In preparing these antibody mimics the CDRs of the $V_H$ and/or $V_L$ chains can be spliced or grafted into the variable loop regions of these antibody mimics. The grafting can involve a deletion of at least two amino acid residues up to substantially all but one amino acid residue appearing in a particular loop region along with the substitution of the CDR sequence. Insertions can be, for example, an insertion of one CDR at one loop region, optionally a second CDR at a second loop region, and optionally a third CDR at a third loop region. Any deletions, insertions, and replacements on the polypeptides can be achieved using recombinant techniques beginning with a known nucleotide sequence (see infra).

Methods for monoclonal antibody production may be achieved using the techniques described herein or others well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., *Staphylococcus* N-acetylmuramoyl-L-alanine amidase or peptide fragments thereof).

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur. J. Immunol.* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

Thus, a second aspect of present invention relates to a cell line that expresses a monoclonal antibody or binding portion disclosed herein. In one embodiment the monoclonal antibody disclosed herein is produced by a hybridoma cell line designated Amd1.1, Amd1.2, Amd1.3, Amd1.5, Amd1.6, Amd1.7, Amd1.8, Amd1.9, Amd1.10, Amd1.11, Amd1.12, Amd1.13, Amd1.14, Amd1.15, Amd1.16, Amd1.17, Amd2.1, Amd2.2, Amd2.4, and Amd2.5.

As noted above, monoclonal antibodies can be made using recombinant DNA methods as described in U.S. Pat. No. 4,816,567 to Cabilly et al., which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, generate host cells that express and secrete monoclonal antibodies. Also, recombinant monoclonal antibodies or fragments thereof of the desired species can be isolated from phage display libraries (McCafferty et al., "Phage Antibodies: Filamentous Phage Displaying Antibody Variable Domains," *Nature* 348:552-554 (1990); Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety).

Still a further aspect relates to a DNA construct comprising a DNA molecule that encodes an antibody or binding portion disclosed herein, a promoter-effective DNA molecule operably coupled 5' of the DNA molecule, and a transcription termination DNA molecule operably coupled 3' of the DNA molecule. The present invention also encompasses an expression vector into which the DNA construct is inserted. A synthetic gene for the polypeptides can be designed such that it includes convenient restriction sites for ease of mutagenesis and uses specific codons for high-level protein expression (Gribskov et al., "The Codon Preference Plot: Graphic Analysis of Protein Coding Sequences and Prediction of Gene Expression," *Nucl. Acids. Res.* 12:539-549 (1984), which is hereby incorporated by reference in its entirety).

The gene may be assembled as follows: first the gene sequence can be divided into parts with boundaries at designed restriction sites; for each part, a pair of oligonucleotides that code opposite strands and have complementary overlaps of about 15 bases can be synthesized; the two oligonucleotides can be annealed and single strand regions can be filled in using the Klenow fragment of DNA polymerase; the double-stranded oligonucleotide can be cloned into a vector, such as, the pET3a vector (Novagen) using restriction enzyme sites at the termini of the fragment and its sequence can be confirmed by a DNA sequencer; and these steps can be repeated for each of the parts to obtain the whole gene. This approach takes more time to assemble a gene than the one-step polymerase chain reaction (PCR) method (Sandhu et al., "Dual Asymetric PCR: One-Step Construction of Synthetic Genes," *BioTech.* 12:14-16 (1992), which is hereby incorporated by reference in its entirety). Mutations could likely be introduced by the low fidelity replication by Taq polymerase and would require time-consuming gene-editing. Recombinant DNA manipulations can be performed according to SAMBROOK & RUSSELL, MOLECULAR CLONING: A LABORATORY MANUAL (2d ed. 1989), which is hereby incorporated by reference in its entirety, unless otherwise stated. To avoid the introduction of mutations during one-step PCR, high fidelity/low error polymerases can be employed as is known in the art.

Desired mutations can be introduced to the polypeptide sequence(s) using either cassette mutagenesis, oligonucleotide site-directed mutagenesis techniques (Deng & Nickoloff, "Site-Directed Mutagenesis of Virtually any Plasmid by Eliminating a Unique Site," *Anal. Biochem.* 200:81-88 (1992), which is hereby incorporated by reference in its entirety), or Kunkel mutagenesis (Kunkel et al., "Rapid and Efficient Site-Specific Mutagenesis Without Phenotypic Selection," *Proc. Natl. Acad. Sci. USA* 82:488-492 (1985); Kunkel et al., "Rapid and Efficient Site-Specific Mutagenesis Without Phenotypic Selection," *Methods Enzymol.* 154:367-382 (1987), which are hereby incorporated by reference in their entirety).

Both cassette mutagenesis and site-directed mutagenesis can be used to prepare specifically desired nucleotide coding sequences. Cassette mutagenesis can be performed using the same protocol for gene construction described above and the double-stranded DNA fragment coding a new sequence can be cloned into a suitable expression vector. Many mutations can be made by combining a newly synthesized strand (coding mutations) and an oligonucleotide used for the gene synthesis. Regardless of the approach utilized to introduce mutations into the nucleotide sequence encoding a polypeptide according to the present invention, sequencing can be performed to confirm that the designed mutations (and no other mutations) were introduced by mutagenesis reactions.

In contrast, Kunkel mutagenesis can be utilized to randomly produce a plurality of mutated polypeptide coding sequences which can be used to prepare a combinatorial library of polypeptides for screening. Basically, targeted loop regions (or C-terminal or N-terminal tail regions) can be randomized using the NNK codon (N denoting a mixture of A, T, G, C, and K denoting a mixture of G and T) (Kunkel et al., "Rapid and Efficient Site-Specific Mutagenesis Without Phenotypic Selection," *Methods Enzymol.* 154:367-382 (1987), which is hereby incorporated by reference in its entirety).

Regardless of the approach used to prepare the nucleic acid molecules encoding the antibody or Amd binding portion, the nucleic acid can be incorporated into host cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements (promoters, suppressers, operators, transcription termination sequences, etc.) for the transcription and translation of the inserted protein-coding sequences. A recombinant gene or DNA construct can be prepared prior to its insertion into an expression vector. For example, using conventional recombinant DNA techniques, a promoter-effective DNA molecule can be operably coupled 5' of a DNA molecule encoding the polypeptide and a transcription termination (i.e., polyadenylation sequence) can be operably coupled 3' thereof.

In accordance with this aspect, the polynucleotides are inserted into an expression system or vector to which the molecule is heterologous. The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art as described by SAMBROOK & RUSSELL, MOLECULAR CLONING: A LABORATORY MANUAL (Cold Springs Laboratory Press, 2001), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

Suitable expression vectors include those which contain replicon and control sequences that are derived from species compatible with the host cell. For example, if *E. coli* is used as a host cell, plasmids such as pUC19, pUC18 or pBR322 may be used. When using insect host cells, appropriate transfer vectors compatible with insect host cells include, pVL1392, pVL1393, pAcGP67 and pAcSecG2T, which incorporate a secretory signal fused to the desired protein, and pAcGHLT and pAcHLT, which contain GST and 6× His tags (BD Biosciences, Franklin Lakes, N.J.). Viral vectors suitable for use in carrying out this aspect include, adenoviral vectors, adeno-associated viral vectors, vaccinia viral vectors, nodaviral vectors, and retroviral vectors. Other suitable expression vectors are described in SAMBROOK AND RUSSELL, MOLECULAR CLONING: A LABORATORY MANUAL (Cold Springs Laboratory Press, 2001), which is hereby incorporated by reference in its entirety. Many known techniques and protocols for manipulation of nucleic acids, for example in preparation of nucleic acid constructs, mutagenesis, sequencing, introduction of DNA into cells and gene expression, and analysis of proteins, are described in detail in CURRENT PROTOCOLS IN MOLECULAR BIOLOGY (Fred M. Ausubel et al. eds., 2003), which is hereby incorporated by reference in its entirety.

Different genetic signals and processing events control many levels of gene expression (e.g., DNA transcription and messenger RNA ("mRNA") translation) and subsequently the amount of antibodies or antibody fragments that are produced and expressed by the host cell. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression. Depending upon the host system utilized, any one of a number of suitable promoters may be used. For instance, when using *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. When using insect cells, suitable baculovirus promoters include late promoters, such as 39K protein promoter or basic protein promoter, and very late promoters, such as the p10 and polyhedron promoters. In some cases it may be desirable to use transfer vectors containing multiple baculoviral promoters. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR. The promoters can be constitutive or, alternatively, tissue-specific or inducible. In addition, in some circumstances inducible (TetOn) promoters can be used.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and promote binding of mRNA to ribosomes by duplexing with the rRNA to allow correct positioning of the ribosome. For a review on maximizing gene expression, see Roberts and Lauer, "Maximizing Gene Expression on a Plasmid Using Recombination in vitro," *Methods in Enzymology*, 68:473-82 (1979), which is hereby incorporated by reference in its entirety.

The present invention also includes a host cell transformed with the DNA construct disclosed herein. The host cell can be a prokaryote or a eukaryote. Host cells suitable for expressing the polypeptides disclosed herein include any one of the more commonly available gram negative bacteria. Suitable microorganisms include *Pseudomonas aeruginosa, Escherichia coli, Salmonella gastroenteritis (typhimirium), S. typhi, S. enteriditis, Shigella flexneri, S. sonnie, S. dysenteriae, Neisseria gonorrhoeae, N. meningitides, Haemophilus influenzae, H. pleuropneumoniae, Pasteurella haemolytica, P. multilocida, Legionella pneumophila, Treponema pallidum, T. denticola, T. orales, Borrelia burgdorferi, Borrelia* spp., *Leptospira interrogans, Klebsiella pneumoniae, Proteus vulgaris, P. morganii, P. mirabilis, Rickettsia prowazeki, R. typhi, R. richettsii, Porphyromonas* (Bacteriodes) *gingivalis, Chlamydia psittaci, C. pneumoniae, C. trachomatis, Campylobacter jejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitensis, B. canis, Spirillum minus, Pseudomonas mallei, Aeromonas hydrophila, A. salmonicida*, and *Yersinia pestis*.

In addition to bacteria cells, animal cells, in particular mammalian and insect cells, yeast cells, fungal cells, plant cells, or algal cells are also suitable host cells for transfection/transformation of the recombinant expression vector carrying an isolated polynucleotide molecule of the type disclosed herein. Mammalian cell lines commonly used in the art include Chinese hamster ovary cells, HeLa cells, baby hamster kidney cells, COS cells, and many others. Suitable insect cell lines include those susceptible to baculoviral infection, including Sf9 and Sf21 cells.

Methods for transforming/transfecting host cells with expression vectors are well-known in the art and depend on the host system selected, as described in SAMBROOK & RUSSELL, MOLECULAR CLONING: A LABORATORY MANUAL (Cold Springs Laboratory Press, 2001), which is hereby incorporated by reference in its entirety. For bacterial cells, suitable techniques include calcium chloride transformation, electroporation, and transfection using bacteriophage. For eukaryotic cells, suitable techniques include calcium phosphate transfection, DEAE-Dextran, electroporation, liposome-mediated transfection, and transduction using retrovirus or any other viral vector. For insect cells, the transfer vector containing the polynucleotide construct is co-transfected with baculovirus DNA, such as AcNPV, to facilitate the production of a recombinant virus. Subsequent recombinant viral infection of Sf cells results in a high rate of recombinant protein production. Regardless of the expression system and host cell used to facilitate protein production, the expressed antibodies, antibody fragments, or antibody mimics can be readily purified using standard purification methods known in the art and described in PHILIP L. R. BONNER, PROTEIN PURIFICATION (Routledge 2007), which is hereby incorporated by reference in its entirety.

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a humanized (or chimeric) antibody, as discussed above. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density combinatorial mutagenesis of the variable region can be used to optimize specificity and affinity of a monoclonal antibody.

A further aspect relates to a pharmaceutical composition comprising a carrier and one or more monoclonal antibodies or one or more Amd binding portions thereof in accordance with the present invention. This pharmaceutical composition may contain two or more antibodies or binding fragments where all antibodies or binding fragments recognize the same epitope. Alternatively, the pharmaceutical composition may contain an antibody or binding fragment mixture where one or more antibodies or binding fragments recognize one epitope of *Staphylococcus* Amd and one or more antibodies or binding fragments recognize a different epitope of *Staphylococcus* Amd. For example, the mixture may contain one or more antibodies that bind specifically to an R1 or R2 domain of *Staphylococcus* Amd in combination with any other antibody that binds to Amd, such as an antibody that binds to the catalytic domain of Amd. The pharmaceutical composition may further contain a pharmaceutically acceptable carrier or other pharmaceutically acceptable components as described infra. In a preferred embodiment, the carrier is an aqueous solution.

A pharmaceutical composition containing the antibodies disclosed herein can be administered to a subject having or at risk of having *Staphylococcus* infection. Various delivery systems are known and can be used to administer the antibodies disclosed herein. Methods of introduction include but are not limited to intradermal, intramuscular, intraperitoneal, intravenous, subcutaneous, intranasal, epidural, and oral routes. The therapeutic agent can be administered, for example by infusion or bolus injection, by absorption through epithelial or mucocutaneous linings (e.g., oral mucosa, rectal and intestinal mucosa, and the like) and can be administered together with other biologically active agents, such as chemotherapeutic agents, antibiotic agents, or other immunotherapeutic agents. Administration can be systemic or local, i.e., at a site of Staph infection or directly to a surgical or implant site.

The pharmaceutical composition may also include a second therapeutic agent to the patient, wherein the second therapeutic agent is an antibiotic agent or immunotherapeutic agent. Exemplary antibiotic agents include, without limitation, vancomycin, tobramycin, cefazolin, erythromycin, clindamycin, rifampin, gentamycin, fusidic acid, minocycline, co-trimoxazole, clindamycin, linezolid, quinupristin-dalfopristin, daptomycin, tigecycline, dalbavancin, telavancin, oritavancin, ceftobiprole, ceftaroline, iclaprim, the carbapenem CS-023/RO-4908463, and combinations thereof. Exemplary immunotherapeutic agents include, without limitation, tefibazumab, BSYX-A110, Aurexis™, and combinations thereof. The above lists of antibiotic agents and immunotherapeutic agents are intended to be non-limiting examples; thus, other antibiotic agents or immunotherapeutic agents are also contemplated. Combinations or mixtures of the second therapeutic agent can also be used for these purposes. These agents can be administered contemporaneously or as a single formulation.

In one embodiment, the immunotherapeutic agent includes a second monoclonal antibody or binding portion thereof that binds specifically to a *Staphylococcus* glucosaminidase (Gmd) and inhibits in vivo growth of a *Staphylococcus* strain. Preferably, the second monoclonal antibody is produced by a hybridoma cell line designated 1C11, 1E12, 2D11, 3A8, 3H6, or 4A12, a humanized variant thereof, or a binding portion thereof (PCT Publication Nos. WO2011/140114 and WO2013/066876 to Schwarz et al., which are hereby incorporated by reference in their entirety). Also in accordance with this aspect, the humanized variant of the second monoclonal antibody is preferably IgG1, IgG2, IgG3, or IgG4 class.

In another embodiment, the binding portion of the second monoclonal antibody comprises a Fab fragment, Fv fragment, single-chain antibody, a $V_H$ domain, or a $V_L$ domain.

The pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid or protein, typically in purified form, together with a suitable amount of carrier so as to provide the form for proper administration to the patient. The formulations correspond to the mode of administration.

Effective doses of the compositions for the treatment of the above-described bacterial infections may vary depending upon many different factors, including mode of administration, target site, physiological state of the patient, other medications administered, and whether treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime. For prophylactic treatment against *Staphylococcus* bacterial infection, it is intended that the pharmaceutical composition(s) disclosed herein can be administered prior to exposure of an individual to the bacteria and that the resulting immune response can inhibit or reduce the severity of the bacterial infection such that the bacteria can be eliminated from the individual. For example, the monoclonal antibody or the pharmaceutical composition can be administered prior to, during, and/or immediately following a surgical procedure, such as joint replacement or any surgery involving a prosthetic implant.

For passive immunization with an antibody or binding fragment disclosed herein, the dosage ranges from about 0.0001 to about 100 mg/kg, and more usually about 0.01 to about 10 mg/kg, of the host body weight. For example, dosages can be about 1 mg/kg body weight or about 10 mg/kg body weight, or within the range of about 1 to about 10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be daily, weekly, monthly, or yearly. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies.

A further aspect relates to a method of introducing an orthopedic implant, tissue graft or medical device into a patient that includes administering to a patient in need of such an implant an effective amount of a monoclonal antibody, binding portion, or pharmaceutical composition disclosed herein, and introducing the orthopedic implant or medical device into the patient.

As used herein, "introducing" a medical device is defined as introducing or installing the device or graft for the first time, as well as resurfacing or otherwise modifying a previously installed device or graft, replacing—in whole or in part—a previously installed device or graft, or otherwise surgically modifying a previously installed device or graft.

In one embodiment, the method of introducing an orthopedic implant, medical device or graft includes administering to the patient in need of the orthopedic implant, medical device or graft an effective amount of a monoclonal antibody or binding fragment or a pharmaceutical composition containing the same, systemically or directly to the site of implantation. Alternatively, or in addition, the orthopedic implant, medical device or graft can be coated or treated with the monoclonal antibody or binding fragment or a pharmaceutical composition containing the same before, during, or immediately after implantation thereof at the implant site.

The orthopedic implant can be any type of implant that is susceptible to *Staphylococcus* infection, such as a joint prosthesis, graft or synthetic implant. Exemplary joint prostheses includes, without limitation, a knee prosthesis, hip prosthesis, finger prosthesis, elbow prosthesis, shoulder prosthesis, temperomandibular prosthesis, and ankle prosthesis. Other prosthetics can also be used. Exemplary grafts or synthetic implants include, without limitation, a vascular graft, a heart valve implant, an artificial intervertebral disk, meniscal implant, or a synthetic or allograft anterior cruciate ligament, medial collateral ligament, lateral collateral ligament, posterior cruciate ligament, Achilles tendon, and rotator cuff. Other grafts or implants can also be used.

The medical device can be any medical device that is susceptible to *Staphylococcus* infection. Exemplary medical devices include, without limitation, a cardiac pacemaker, cerebrospinal fluid shunt, dialysis catheter, or prosthetic heart valve.

In accordance with this aspect, a second therapeutic agent may also be administered to the patient. The second therapeutic agent may be an antibiotic agent or immunotherapeutic agent. Exemplary antibiotic agents and immunotherapeutic agents are described above.

In one embodiment, the method of introducing an orthopedic implant or medical device is intended to encompass the process of installing a revision total joint replacement. Where infection, particularly *Staphylococcus* sp. infection of an original joint replacement occurs, the only viable treatment is a revision total joint replacement. In this embodiment, the infected joint prosthesis is first removed and then the patient is treated for the underlying infection. Treatment of the infection occurs over an extended period of time (i.e. 6 months), during which time the patient is immobile (or has only limited mobility) and receives high doses of antibiotics to treat the underlying infection and optionally one or more monoclonal antibodies or binding portions, or pharmaceutical compositions disclosed herein. Upon treatment of the underlying infection, the new joint prosthesis is installed. Immediately prior (i.e., within the two weeks preceding new joint prosthesis installation) and optionally subsequent to installation of the new joint prosthesis, the patient is administered one or more monoclonal antibodies or binding portions, or pharmaceutical compositions disclosed herein. This treatment can be repeated one or more times during the post-installation period. Antibiotic treatment may be administered in combination with or concurrently with the one or more monoclonal antibodies or binding portions, or pharmaceutical compositions disclosed herein. These treatments are effective to prevent infection or reinfection during the revision total joint replacement.

Another aspect relates to a method of treating or preventing a Staphylococcus infection that involves administering to a patient susceptible to or having a Staphylococcus infection an effective amount of a monoclonal antibody, a monoclonal antibody binding portion, or pharmaceutical composition disclosed herein, or a combination thereof.

In one embodiment of treating Staphylococcus infection, the administration of the monoclonal antibody, monoclonal antibody binding portion, pharmaceutical composition, or combination thereof, is repeated. The initial and repeated administrations can be concurrent with or in sequence relative to other therapies and carried out systemically or carried out directly to a site of the Staphylococcus infection, or both.

The method of treating Staphylococcus infection can be used to treat Staphylococcus infection at sites which include, without limitation, infection of the skin, muscle, cardiac, respiratory tract, gastrointestinal tract, eye, kidney and urinary tract, and bone or joint infections.

In one embodiment, this method is carried out to treat osteomyelitis by administering an effective amount of the monoclonal antibody or binding fragment thereof or the pharmaceutical composition to a patient having a Staphylococcus bone or joint infection. Administration of these agents or compositions can be carried out using any of the routes described supra; in certain embodiments, administration directly to the site of the bone or joint infection can be performed.

In each of the preceding embodiments, a second therapeutic agent may also be administered to the patient. The second therapeutic agent may be an antibiotic agent or immunotherapeutic agent. Exemplary antibiotic agents and immunotherapeutic agents are described above.

The methods of treatment as disclosed herein can be used to treat any patient in need, including humans and non-human mammals, however, the methods are particularly useful for immuno-compromised patients of any age, as well as patients that are older than 50 years of age.

In the preceding embodiments, the preventative or therapeutic methods of treatment can reduce the rate of infection, the severity of infection, the duration of infection, or any combination thereof. In certain embodiments, the preventative or therapeutic methods of treatment can reduce or altogether eliminate the total number of SRCs or abscesses, and/or increase the number of sterile SRCs or abscesses (assuming SRCs or abscesses are present). In certain embodiments, partial or complete healing of an osteolytic lesion is contemplated, as indicated by a reduction in lesion size or volume.

Another aspect relates to a method of determining presence of Staphylococcus in a sample that involves exposing a sample to a monoclonal antibody or binding portion disclosed herein and detecting whether an immune complex forms between the monoclonal antibody or binding portion and Staphylococcus or a Staphylococcus amidase present in the sample, whereby presence of the immune complex after said exposing indicates the presence of Staphylococcus in the sample.

The sample can be a blood sample, a serum sample, a plasma sample, a mucosa-associated lymphoid tissue (MALT) sample, a cerebrospinal fluid sample, an articular liquid sample, a pleural liquid sample, a saliva sample, a urine sample, or a tissue biopsy sample.

Detecting formation of an immune complex can be performed by well known methods in the art. In one embodiment, the detecting is carried out using an immunoassay. The immunoassay method used may be a known immunoassay method, and for example, common immunoassay methods such as latex agglutination methods, turbidimetric methods, radioimmunoassay methods (for example, RIA and RIMA), enzyme immunoassay methods (for example, ELISA and EIA), gel diffusion precipitation reaction, flow cytometry, immunoelectrophoresis (for example Western blotting), dot blot methods, immunodiffusion assay, protein A immunoassay, fluorescent immunoassay (for example, FIA and IFMA), immunochromatography methods and antibody array methods may be mentioned, with no limitation to these. These immunoassay methods are themselves known in the field, and can be easily carried out by a person skilled in the art.

The monoclonal antibody or binding portion can be directly labeled by various methods known in the art. The label serves as reagent means for determining the extent to which the monoclonal antibody or binding portion is bound by analyte in the immunoassay. The label can be, without limitation, a radioisotope, enzyme, chromophore, fluorophore, light-absorbing or refracting particle. Preferably, the label is a radiolabel, fluorophore, or chemiluminescent label. It is preferable to label the antibody or binding portion as extensively as possible without destroying its immunoreactivity.

EXAMPLES

The examples below are intended to exemplify the practicing the claimed subject matter, but are by no means intended to limit the scope thereof.

Example 1—Preparation of Antigen

A recombinant form of the entire amidase domain of S. aureus autolysin that includes a hexa-histidine sequence near its N-terminus (His-Amd) was prepared. The open reading frame for His-Amd was designed by collecting known sequences of S. aureus autolysin, determining the consensus protein sequence using Geneious™ software, and then optimizing codon usage for expression in E. coli. The encoded consensus protein and encoding open reading frame sequences for His-Amd are identified as SEQ ID NOS: 1 and 2 below.

```
SEQ ID NO: 1 (Hex-histidine leader sequence plus
Autolysin aa 198-775)
MHHHHHHSASAQPRSVAATPKTSLPKYKPQVNSSINDYIRKNNLKAPKIE EDYTSYFPKYAyRNGVGRPEGIVVHDTANDRSTINGEISYMKNNYQNAFV

HAFVDGDRIIETAPTDYLSWGVGAVGNPRFINVEIVHTHDYASFARSMNN

YADYAATQLQYYGLKPDSAEYDGNGTVWTHYAVSKYLGGTDHADPHGYLR

SHNYSYDQLYDLINEKYLIKMGKVAPWGTQSTTTPTTPSKPTTPSKPSTG

KLTVAANNGVAQIKPTNSGLYTTVYDKTGKATNEVQKTFAVSKTATLGNQ

KFYLVQDYNSGNKFGWVKEGDWYNTAKSPVNVNQSYSIKPGTKLYTVPWG

TSKQVAGSVSGSGNQTFKASKQQQIDKSIYLYGSVNGKSGWVSKAYLVDT

AKPTPTPTPKPSTPTTNNKLTVSSLNGVAQINAKNNGLFTTVYDKTGKPT
```

-continued
KEVQKTFAVTKEASLGGNKFYLVKDYNSPTLIGWVKQGDVIYNNAKSPVN

VMQTYTVKPGTKLYSVPWGTYKQEAGAVSGTGNQTFKATKQQQIDKSIYL

FGTVNGKSGWVSKAYLAVPAAPKKAVAQPKTAVK

SEQ ID NO: 2
ATGCACCATCACCACCACCACAGCGCAAGCGCACAGCCTCGTTCCGTCGC

CGCCACCCCGAAAACCAGCTTGCCGAAGTACAAACCGCAAGTTAATAGCA

GCATCAACGACTACATCCGCAAAAACAACCTGAAGGCCCCGAAAATTGAA

GAGGACTATACCAGCTATTTCCCGAAATATGCTTACCGTAATGGTGTCGG

TCGTCCGGAGGGTATTGTGGTCCACGACACCGCGAATGACCGTAGCACCA

TCAACGGTGAGATTAGCTACATGAAAAACAATTACCAAAACGCGTTCGTG

CACGCCTTCGTCGATGGCGATCGCATCATCGAAACCGCGCCAACCGACTA

TCTGTCCTGGGGTGTGGGTGCCGTTGGCAACCCGCGTTTCATCAATGTGG

AGATTGTTCATACCCACGACTACGCGAGCTTTGCACGTAGCATGAACAAC

TACGCCGATTATGCTGCAACGCAGCTGCAGTACTACGGCCTGAAACCGGA

TAGCGCGGAGTATGACGGTAACGGTACGGTGTGGACGCATTATGCGGTGA

GCAAATACCTGGGTGGTACCGATCATGCTGATCCGCATGGCTACCTGCGC

TCTCACAACTATAGCTACGACCAGTTGTACGACCTGATCAATGAGAAATA

TCTGATTAAGATGGGTAAGGTTGCACCGTGGGGTACGCAGAGCACCACGA

CGCCGACCACGCCGAGCAAACCGACGACCCCGTCCAAACCGTCTACCGGC

AAACTGACGGTCGCGGCTAATAACGGTGTCGCGCAGATTAAACCGACCAA

CAGCGGTCTGTACACCACCGTCTATGATAAAACGGGCAAAGCCACCAATG

AGGTTCAAAAGACGTTCGCAGTTAGCAAAACGGCGACCCTGGGTAACCAA

AAGTTCTACCTGGTTCAGGATTACAATAGCGGCAACAAATTTGGTTGGGT

GAAAGAAGGCGACGTTGTGTACAATACCGCGAAGTCCCCGGTGAACGTTA

ATCAGAGCTATAGCATCAAGCCGGGTACCAAATTGTATACGGTGCCGTGG

GGTACCAGCAAGCAAGTTGCGGGTAGCGTCAGCGGCTCTGGTAACCAGAC

CTTCAAGGCGTCTAAGCAACAACAAATTGACAAAAGCATTTACCTGTATG

GTAGCGTTAATGGTAAAAGCGGCTGGGTGTCTAAAGCGTATCTGGTCGAC

ACCGCAAAGCCGACGCCAACGCCGACCCCGAAGCCGAGCACCCCAACCAC

CAACAACAAGCTGACGGTCAGCTCCCTGAATGGTGTTGCGCAAATCAATG

CGAAGAATAATGGCCTGTTTACCACCGTTTACGATAAGACGGGCAAGCCA

ACGAAAGAAGTCCAGAAAACCTTTGCTGTCACCAAAGAAGCCAGCCTGGG

CGGTAACAAGTTCTATCTGGTTAAGGACTACAACTCCCCGACGCTGATCG

GTTGGGTCAAACAAGGCGATGTCATTTACAATAACGCGAAAAGCCCGGTT

AATGTGATGCAAACCTATACCGTCAAACCGGGTACGAAGCTGTATTCCGT

TCCGTGGGGCACGTACAAACAAGAAGCAGGCGCGGTGAGCGGTACCGGCA

ATCAGACCTTTAAGGCCACCAAGCAGCAGCAGATCGATAAATCTATTTAC

TTGTTTGGCACCGTGAATGGCAAGAGCGGTTGGGTTTCTAAGGCATACCT

GGCGGTGCCGGCAGCACCGAAGAAGGCGGTGGCGCAGCCAAAGACCGCAG

TGAAG

The DNA molecule encoding His-Amd was synthesized de novo by DNA2.0 (Menlo Park, Calif.), and then inserted into the pJexpress *E. coli* expression vector.

His-Amd protein expressed in *E. coli* was primarily in the form of insoluble inclusion bodies which were harvested and solubilized in PBS with 8M urea. After further purification by metal chelation chromatography on TALON resin, the His-Amd was renatured by an extensive process of dialysis against phosphate buffered saline (PBS) containing 1 mM $Zn^{2+}$ and stepwise reductions in the level of urea.

The Amd catalytic domain (His-Amd-cat) was prepared in an identical manner except that the portion of the open reading frame encoding the R1 and R2 domains was omitted (see FIG. 1). The encoded consensus protein and encoding open reading frame sequences for His-Amd-cat are identified as SEQ ID NOS: 3 and 4 below.

SEQ ID NO: 3 (Hex-histidine leader sequence plus Autolysin aa 198-441)
MHHHHHHSASAQPRSVAATPKTSLPKYKPQVNSSINDYIRKNNLKAPKIE

EDYTSYFPKYAYRNGVGRPEGIVVHDTANDRSTINGEISYMKNNYQNAFV

HAFVDGDRIIETAPTDYLSWGVGAVGNPRFINVEIVHTHDYASFARSMNN

YADYAATQLQYYGLKPDSAEYDGNGTVWTHYAVSKYLGGTDHADPHGYLR

SHNYSYDQLYDLINEKYLIKMGKVAPWGTQSTTTPTTPSKPTTPSKPSTG

K

SEQ ID NO: 4
ATGCACCATCACCACCACCACAGCGCAAGCGCACAGCCTCGTTCCGTCGC

CGCCACCCCGAAAACCAGCTTGCCGAAGTACAAACCGCAAGTTAATAGCA

GCATCAACGACTACATCCGCAAAAACAACCTGAAGGCCCCGAAAATTGAA

GAGGACTATACCAGCTATTTCCCGAAATATGCTTACCGTAATGGTGTCGG

TCGTCCGGAGGGTATTGTGGTCCACGACACCGCGAATGACCGTAGCACCA

TCAACGGTGAGATTAGCTACATGAAAAACAATTACCAAAACGCGTTCGTG

CACGCCTTCGTCGATGGCGATCGCATCATCGAAACCGCGCCAACCGACTA

TCTGTCCTGGGGTGTGGGTGCCGTTGGCAACCCGCGTTTCATCAATGTGG

AGATTGTTCATACCCACGACTACGCGAGCTTTGCACGTAGCATGAACAAC

TACGCCGATTATGCTGCAACGCAGCTGCAGTACTACGGCCTGAAACCGGA

TAGCGCGGAGTATGACGGTAACGGTACGGTGTGGACGCATTATGCGGTGA

GCAAATACCTGGGTGGTACCGATCATGCTGATCCGCATGGCTACCTGCGC

TCTCACAACTATAGCTACGACCAGTTGTACGACCTGATCAATGAGAAATA

TCTGATTAAGATGGGTAAGGTTGCACCGTGGGGTACGCAGAGCACCACGA

CGCCGACCACGCCGAGCAAACCGACGACCCCGTCCAAACCGTCTACCGGC

AAA

Example 2—Inoculation of Mice and Preparation of Hybridomas

For the initial hybridoma fusion (Fusion #1), six female Balb/c mice were immunized two times with 75 µg of His-AmdR1R2, in the Sigma Adjuvant System (Sigma, Cat. No. S6322) by intraperitoneal injection at seven-week intervals. Two of the mice with the highest titers in ELISA on immobilized His-AmdR1R2 were selected for hybridoma fusion. Each mouse received a final immunization of 350 µg of His-AmdR1R2, i.p., four days prior to sacrifice and hybridoma fusion.

For the second hybridoma fusion (Fusion #2), Balb/c mice were immunized two times: first dose with 120 µg of His-AmdR1R2-B from GenScript (Lot Number 222933505/ P20011303) in Sigma Adjuvant System (Sigma, Cat. No. S6322), and a second immunization with 100 µg of His-AmdR1R2-B conjugated with Keyhole limpet hemocyanin (KLH) (Imject EDC mcKLH Spin Kit; Thermo Scientific; Cat #77671) at twelve-week intervals. Two of the mice with the highest titers in ELISA on immobilized His-AmdR1R2 were selected for hybridoma fusion. Each mouse received a final immunization of 100 µg of His-AmdR1R2, i.p., four days prior to sacrifice and hybridoma fusion.

Hybridomas were prepared from splenocytes by conventional methods.

Example 3—Characterization of Monoclonal Antibodies

New monoclonal antibodies were screened on multiple related proteins to determine that they recognized native Amd (and not just the recombinant form) and whether their epitope was present on the catalytic (C) or cell wall binding domain (R1, R2 or R3). The proteins used for screening the monoclonal antibodies are identified in Table 1 below.

TABLE 1

Proteins Used for Screening the Monoclonal Antibodies

| Protein/ Antigen Name | SEQ ID NO: | Region of Autolysin/Sequence Description |
|---|---|---|
| His-AmdR1R2 | 1 | MGHHHHHH - Autolysin aa 198 to 775 |
| His-Amdcat | 3 | MGHHHHHH - Autolysin aa 198 to 441 |
| Native Amd | 75, 76, 77 | Mixture of S. aureus UAMS-1 Δspa proteins including full length autolysin, Amd, and Gmd |
| His-AmdR1R2-B | 78 | MGHHHHHH - Autolysin aa 198 to 775 - BirA biotinylation site |
| His-R3Gmd-B | 79 | MGHHHHHH - Autolysin aa 776 to 1276 - BirA biotinylation site |

Screening assays were carried out by ELISA using the proteins identified in Table 1 as capture antigen. ELISA tests were performed using widely practiced conventions. Specifically, antigens were adsorbed onto the wells of NUNC MAXISORP® microtiter plates. Each antigen was prepared as a solution in phosphate-buffered saline (PBS) at 2 µg/mL and 100 µL was added to assigned microtiter wells and antigens were allowed to adsorb for either 1 hour at RT or overnight at 4° C. Wells were blocked by the addition of 200 µL of 3% bovine serum albumin (BSA), without removal of the coating antigen, and incubated for either 1 hour at RT or overnight at 4° C. Coated and blocked plates were then washed 3× with PBS supplemented with 0.05% TWEEN® 20 (PBS-T) and either used immediately or stored at 4° C.

Cell-free hybridoma culture supernatants were added to assigned wells and incubated for 1 hour at RT and then washed six times with PBS-T. The secondary antibody, horseradish peroxidase-conjugated goat anti-mouse IgG (Southern Biotechnology) was then added, 100 µL per well at 0.1-0.5 µg/mL in PBS-T, and incubated 1 hour at RT. Microtiter plates were again washed six times with PBS-T and then developed by the addition of 100 µL of either 3,3',5,5'-Tetramethylbenzidine (TMB) or 2,2'-azino-bis(3-ethylbenzothiazoline-6-sulphonic acid) (ABTS). The results of these ELISA are shown in Table 2 below.

TABLE 2

Summary of Successfully Cloned and Characterized anti-Amd mAbs

| Anti-Amd mAb | Heavy Chain Class | Amidase Domain C or R1R2 | IP with native Amidase | Precipitation of S. aureus | $K_D$ | Amidase Enzyme Inhibition |
|---|---|---|---|---|---|---|
| 1.1 | IgG1 | R1R2 | Yes | Yes | 2.5 nM | No |
| 1.2 | IgG1 | R1R2 | Yes | Yes | ND | No |
| 1.4 | IgG1 | R1R2 | Yes | Yes | ND | ND |
| 1.5 | IgG1 | R1R2 | Yes | Yes | ND | No |
| 1.6 | IgG1 | C | Yes | Yes | 2.1 nM | Yes |
| 1.7 | IgG1 | R1R2 | Yes | Yes | ND | No |
| 1.8 | IgG1 | R1R2 | Yes | Yes | 2.6 nM | No |
| 1.9 | IgG1 | R1R2 | Yes | Yes | 2.6 nM | No |
| 1.10 | IgG1 | C | No | ND | ND | ND |
| 1.11 | IgG1 | R1R2 | Yes | Yes | 3.4 nM | No |
| 1.12 | IgG1 | R1R2 | No | No | ND | ND |
| 1.13 | IgG1 | C | Yes | No | ND | ND |
| 1.14 | IgG1 | R1R2 | No | ND | ND | ND |
| 1.15 | IgG1 | R1R2 | Yes | Yes | ND | ND |
| 1.16 | IgG1 | C | Yes | Yes | 2.6 nM | No |
| 1.17 | IgG1 | C | Yes | No | ND | No |
| 2.1 | IgG1 | C | Yes | Yes | 4.9 nM | Yes |
| 2.2 | IgG1 | C | Yes | Yes | 1.4 nM | No |
| 2.4 | IgG1 | R1R2 | Yes | Yes | 1.9 nM | No |
| 2.5 | IgG1 | R1R2 | Yes | Yes | 6.3 nM | No |

ND = Not Determined.

Example 4—Inhibition of Amd Catalytic Activity In Vitro

Figure 2:
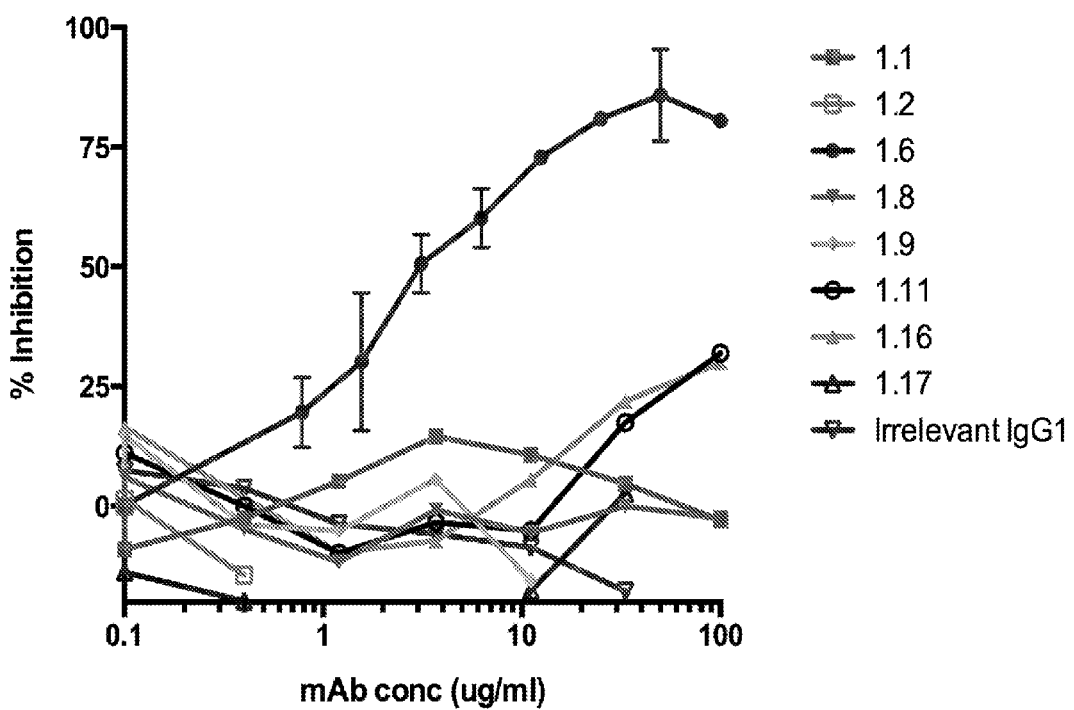
FIG. 2 is a graph showing inhibition of Amd enzymatic activity eight anti-Amd monoclonal antibodies and an isoytpe-matched antibody of irrelevant specificity. Recombinant Amd (rAmd) was prepared in E. coli (His-AmdR1R2-B in Table 1). rAmd (1.5 μg/mL) was mixed in PBS with a turbid suspension of peptidoglycan prepared from S. aureus cell walls and its lytic activity was measured by the reduction in turbidity (measured as $A_{490}$) following incubation for 60 minutes at 37° C. (Δ60). For the inhibition test, the concentration of rAmd was sufficient to reduce the $A_{490}$ by 70%. Purified anti-Amd mAbs were added to the rAmd at the indicated concentrations and then lysis of peptidoglycan by the Mab:rAmd mixture was measured. Percent inhibition was calculated as: $100 \times (1-(\Delta 60/A_{490}$ inhibitor/$\Delta 60 A_{490}$ no inhibitor control)).

An attribute that may contribute to the potency of a therapeutic monoclonal antibody is its direct inhibition of the activity of an enzyme essential for bacterial growth and survival such as amidase. Some of the anti-Amd mAbs were tested for inhibition of amidase activity by measuring the extent to which they inhibited the ability of amidase to clarify a turbid suspension of S. aureus peptidoglycan. Results for eight antibodies from Fusion #1 are presented in FIG. 2. MAb Amd1.6 was a potent inhibitor of amidase activity while the others were not, with the possible exception of Amd1.16, which appeared to be a low affinity inhibitor. Results for all of the antibodies are summarized in Table 2.

Example 5—The Majority of Anti-Amd mAbs Precipitate S. aureus

Figure 3:
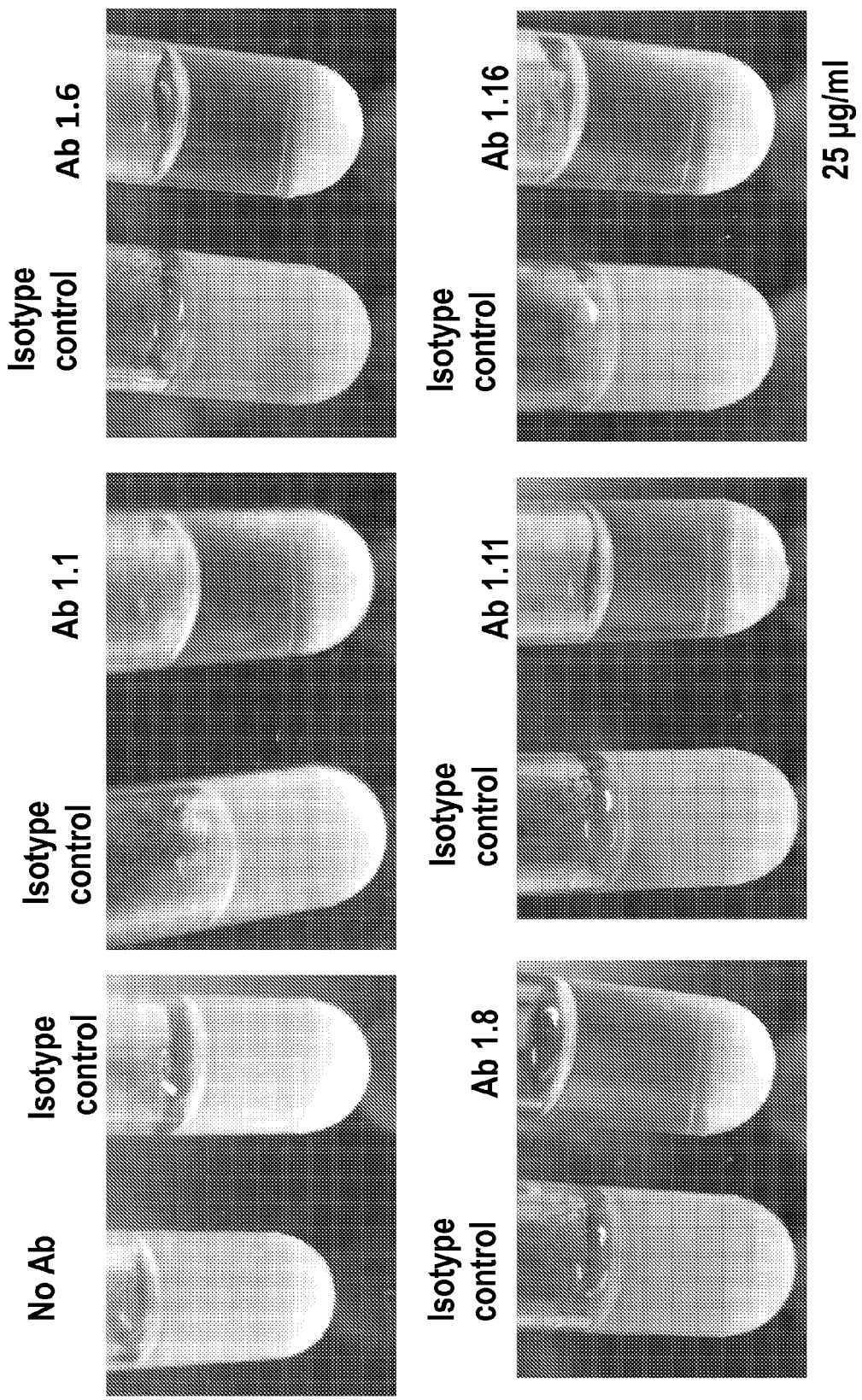
FIG. 3 is an image of S. aureus precipitation by representative anti-Amd antibodies. When S. aureus cells are cultured in the presence of most Staphylococcus-specific mAbs they form into large clusters that fall out of suspension yielding a relatively clear supernatant. USA300LAC S. aureus were cultured in TSB at 37° C. for eight hours in the presence of the indicated anti-Amd mAbs, each at 25 μg/mL. The sample containing no antibody (No Ab) and an irrelevant isotype-matched antibody (Isotype control) had turbid supernatants without evident cell pellets; mAbs Amd1.1, Amd1.6, Amd1.8, Amd1.11, and Amd1.16 had clear supernatants and cell pellets. Other mAbs producing clear supernatants and cell pellets are listed in Table 2, infra, as are mAbs that failed to precipitate S. aureus from suspension.

Another attribute likely to be important for the potency of therapeutic monoclonal antibodies is the recognition of antigenic structures (epitopes) accessible from the outside of the intact bacterial cell. A visible manifestation of this recognition is the antibody-mediated clustering of individual bacteria into large aggregates that precipitate from suspension yielding a cell-rich pellet and a less turbid supernatant. Many of the candidate mAbs formed conspicuous precipitates as depicted in FIG. 3. A summary of the precipitation activity of the candidate mAbs from fusions 1 and 2 is in Table 2.

Example 6—Uniqueness of Each mAb and Identification of Germ Line Assignments Based on Sequencing Gene assignments were identified by matching nucleotide sequences for anti-Amd heavy and light chains with the files of known murine V-region sequences in IgBLAST at the National Center for Biotechnology Information. The results of this analysis are presented in Table 3 below. Each of the antibodies from Fusion #1 was unique except possibly for Amd1.1 and 1.4 which were derived from the same germline $V_H$ gene segments. Two of the antibodies from Fusion#2 share heavy chain $V_H$ and $J_H$ gene segments with mAbs isolated in Fusion #1 (mAb Amd2.4 with mAb Amd1.11; mAb Amd 2.2 with mAb Amd1.7). In each case the light chains are distinct.

TABLE 3

Most Probable Germ Line $V_H$, $J_H$, $V_L$ and $J_L$ Gene Segments

| Hybridoma | Germ Line $V_H$ | Germ Line $J_H$ | Germ Line $V_L$ | Germ Line $J_L$ |
|---|---|---|---|---|
| Amd 1.1 | IGHV14-3 (7) | IGHJ4 (0) | IGKV4-50 (6) | IGKJ2 (0) |
| Amd 1.2 | IGHV1-14 (4) | IGHJ2 (0) | IGKV5-43 (0) | IGKJ2 (0) |
| Amd 1.4 | IGHV14-3 (6) | IGHJ4 (0) | NA | NA |
| Amd 1.5 | IGHV14-1 (11) | IGHJ4 (0) | NA | NA |
| Amd 1.6 | IGHV1-5 (8) | IGHJ3 (0) | IGKV6-32 (3) | IGKJ1 (0) |
| Amd 1.7 | IGHV1S29 (7) | IGHJ2 (0) | IGKV6-32 (3) | IGKJ1 (0) |
| Amd 1.8 | NA | NA | IGKV5-39 (2) | IGKJ2 (0) |
| Amd 1.9 | IGHV5S12 (5) | IGHJ2 (0) | IGKV12-46 (8) | IGKJ1 (0) |
| Amd 1.10 | NA | NA | IGKV4-68 (0) | IGKJ2 (0) |
| Amd 1.11 | IGHV9-3-1 (2) | IGHJ4 (0) | IGKV5-48 (0) | IGKJ5 (0) |
| Amd 1.12 | IGHV1-54 (3) | IGHJ4 (0) | IGKV12-44 (6) | IGKJ2 (0) |
| Amd 1.13 | IGHV1-82 (7) | IGHJ4 (0) | IGKV8-19 (1) | IGKJ4 (0) |
| Amd 1.15 | NA | NA | IGKV6-17 (7) | IGKJ4 (0) |
| Amd 1.16 | IGHV1-80 (6) | IGHJ4 (0) | NA | NA |
| Amd 1.17 | IGHV5-4 (2) | IGHJ2 (0) | IGKV1-117 (1) | IGKJ1 (0) |
| Amd 2.1 | IGHV5S12 (5) | IGHJ4 (0) | IGKV8-19 (4) | IGKJ5 (0) |
| Amd 2.2 | IGHV1S29 (5) | IGHJ2 (0) | IGKV4-86 (1) | IGKJ5 (0) |
| Amd 2.4 | IGHV9-3-1 (1) | IGHJ4 (0) | IGKV4-63 (7) | IGKJ2 (0) |
| Amd 2.5 | NA | NA | IGKV12-41 (9) | IGKJ2 (0) |

Numbers in parentheses are the number of non-synonymous base changes observed between the anti-Amd sequence and the putative germ line precursor.
NA = sequencing was unsuccessful.

Example 7—Measurement of the Affinity of Anti-Amd mAbs for *S. aureus* Amidase

Figure 4:
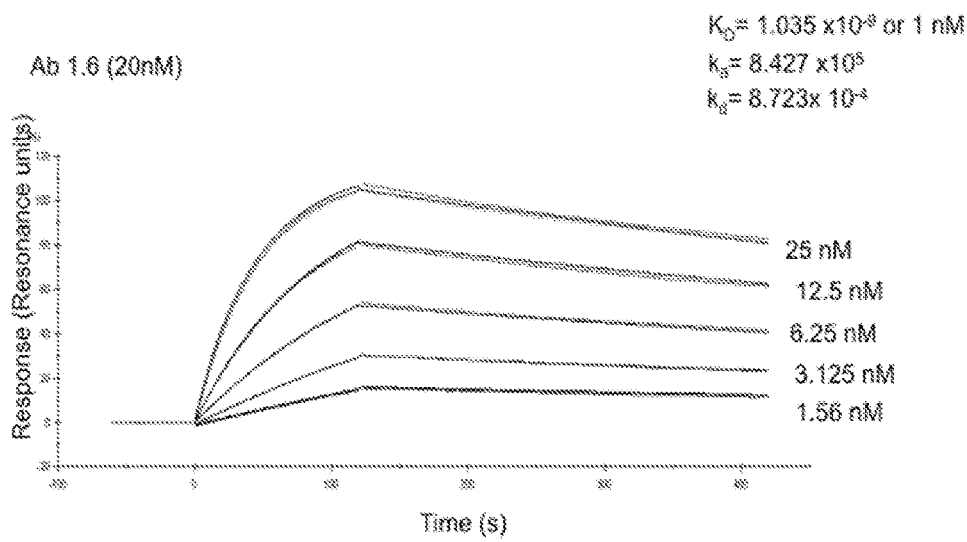
FIG. 4 illustrates the biomolecular interaction analysis of immobilized mAb Amd1.6 with soluble Amd. The affinity of the interaction between mAb Amd1.6 and soluble Amd was measured on a Biacore T-200. Rabbit anti-mouse Fc IgG was immobilized on the surface of a CM-5 biosensor chip and used to capture mAb Amd1.6 which then captured Amd from a flowing field. The mass of Amd bound by mAb Amd1.6 is measured in Resonance Units (y-axis) against time on the x-axis. The capture (association, t=0 to 120 sec) and release (dissociation, t=120 to 420 sec) phases are presented. The experiment was repeated with concentrations of Amd varying in two-fold increments from 1.56 to 25 nM. Measurements were made according the manufacturer's instructions and kinetic data were analyzed using biomolecular interaction analysis (BIA) evaluation software (version 3.1) from Biacore AB.

An essential attribute of an antibacterial antibody is high affinity for the bacterial antigen. The higher the affinity, the lower the dose required for prophylaxis or therapy. While some therapeutic antibodies have affinities, expressed as $K_D$, in the range of 10 nM ($K_A = 10^8$ M$^{-1}$) it is generally desirable to have antibodies with $K_D \sim 1$ nM ($K_A \sim 10^9$ M$^{-1}$). The affinity of immobilized anti-Amd mAbs for soluble His-AmdR1R2-B was measured using surface plasmon resonance technology on a Biacore T-200. Representative data for mAb Amd1.6 is presented in FIG. 4. While its average affinity for Amd is about 2.1 nM, FIG. 4 illustrates a measured affinity of about 1 nM. Measured affinities for the other candidate mAbs are listed in Table 2.

Example 8—Anti-Amd mAb Amd1.6 Inhibits In Vitro Biofilm Formation by *S. aureus* Strain UAMS-1

Figure 5:
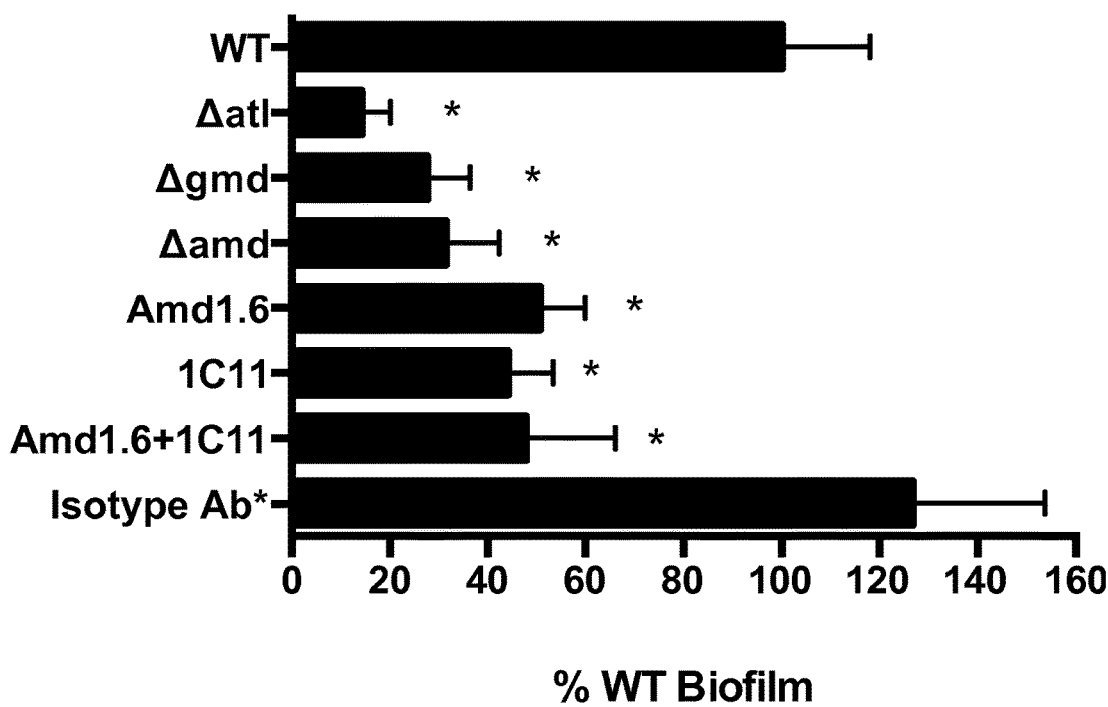
FIG. 5 is a graph illustrating the inhibitory effect of anti-Amd antibodies on in vitro biofilm formation as compared to the Amd, Gmd and autolysin deletion mutant strains. A biofilm assay utilizing Calgary plates was performed by coating the plate and lid pegs with human plasma for 16 hours at 4° C. *S. aureus* was then seeded at OD 600 nm of 0.05 in the presence or absence of 25 µg/mL anti-Amd (Amd1.6), anti-Gmd (1C11) and combination of anti-Amd+ anti-Gmd (Amd1.6+1C11) mAbs. Biofilm formation was allowed for 24 hours at 37° C. After washing, biofilms were stained with crystal violet and biofilm content was measured by spectrophotometry at 595 nm. As a positive control for biofilm inhibition, UAMS-1 deficient strain for amidase (Δamd), glucosaminidase (Δgmd) or autolysin (Δatl) were seeded at same OD. Results are reported as the amount of biofilm formation (i.e., crystal violet staining) as a percentage of the wild type (WT), untreated UAMS-1 culture (A); * $p<0.05$ compared to WT.

Amd has been reported to be involved in the formation of biofilms (Bose et al., "Contribution of the *Staphylococcus aureus* Atl AM and GL Murein Hydrolase Activities in Cell Division, Autolysis, and Biofilm Formation," *PLoS One* 7:e42244 (2012); Chen et al., "Secreted Proteases Control Autolysin-mediated Biofilm Growth of *Staphylococcus aureus*," *J Biol Chem*. 288:29440-29452 (2013); Houston et al., "Essential Role for the Major Autolysin in the Fibronectin-binding Protein-mediated *Staphylococcus aureus* Biofilm Phenotype," *Infect Immun*. 79:1153-1165 (2011), each of which is hereby incorporated by reference in its entirety). Biofilm formation is a process believed to be central to the persistence of *S. aureus* infections in vivo, especially those associated with orthopedic implants (Ehrlich and Arciola, "From Koch's Postulates to Biofilm Theory: The Lesson of Bill Costerton," *Internat'l J Artificial Organs* 35:695-699 (2012), which is hereby incorporated by reference in its entirety). To measure the ability of anti-Amd mAb1.6 to inhibit biofilm formation, *S. aureus* strain UAMS-1 was grown in Calgary plates (Ceri et al., "The Calgary Biofilm Device: New Technology for Rapid Determination of Antibiotic Susceptibilities of Bacterial Biofilms," *J Clin Microbiol*. 37:1771-1776 (1999), which is hereby incorporated by reference in its entirety), which are specifically designed for measuring biofilm formation. Deletion mutants in the autolysin gene (Δatl) and in its Amd (Δamd) and Gmd (Δgmd) subdomains each formed substantially less biofilm than the WT UAMS-1 (20-35% of WT). Amd1.6 alone or in combination with the anti-Gmd mAb 1C11 (see PCT Publication Nos. WO2011/140114 to Schwarz et al., which is hereby incorporated by reference in its entirety) reduced biofilm formation by more than 50% while an isotype-matched mAb of irrelevant specificity had no effect (FIG. 5) Inhibition of the extracellular Amd by exogenous anti-Amd mAb is nearly as effective as deletion of the autolysin gene.

Figure 6E:
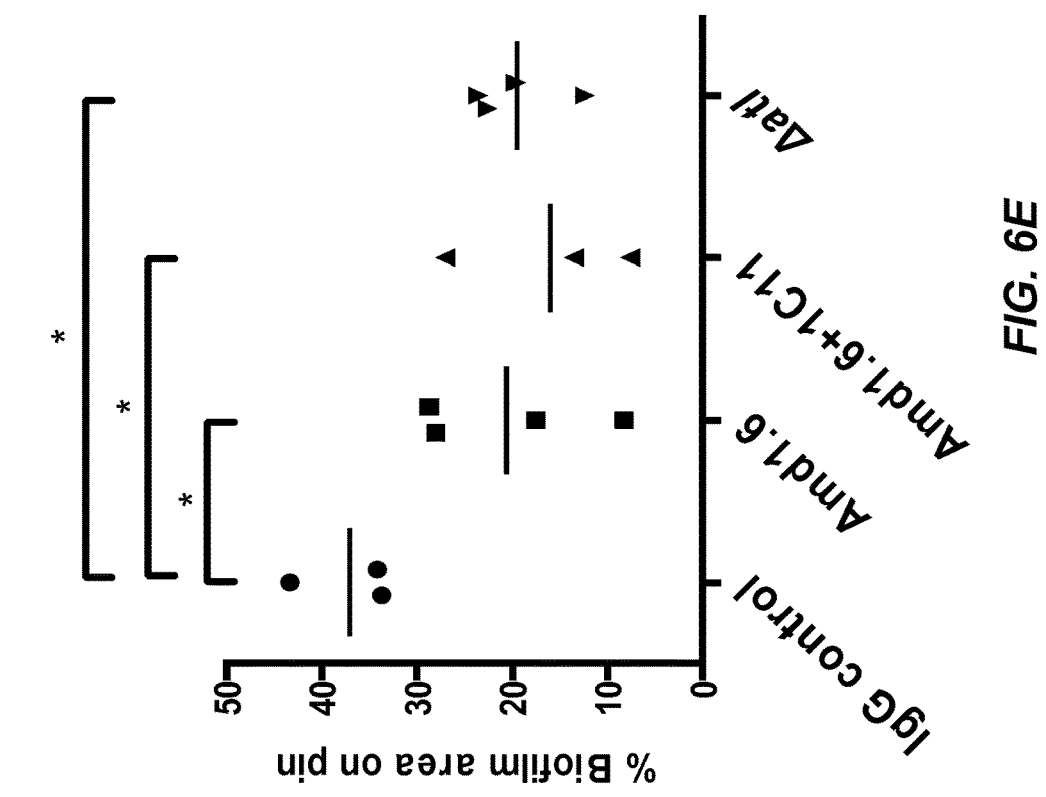
Figure 6E:
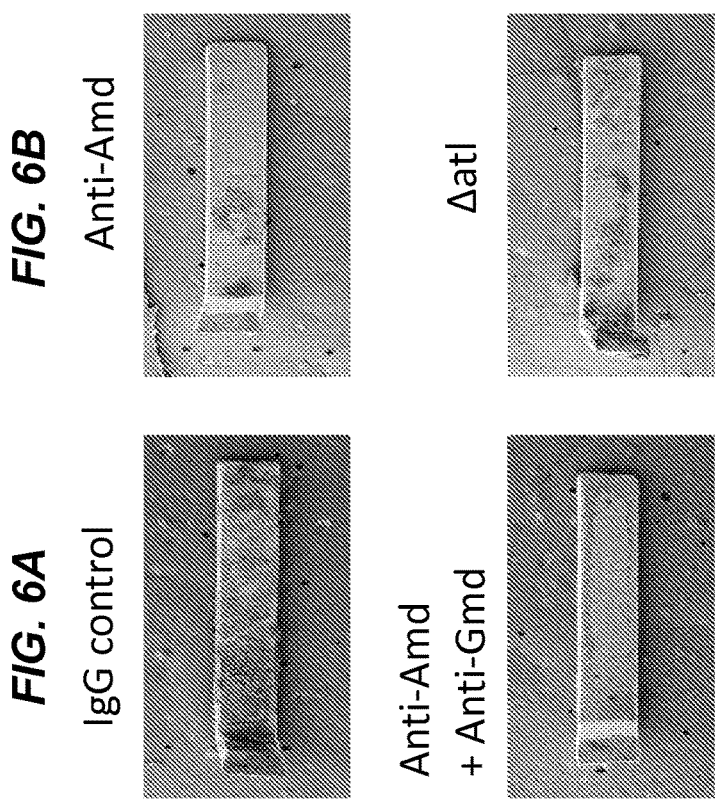

Example 9—Anti-Amd mAb Amd1.6 Reduces Biofilm Formation in an In Vivo Model of Implant-Associated Osteomyelitis Because implant-associated biofilms are thought to be a major source of persistence infection in orthopaedic indications, the ability to reduce the extent of biofilm formation on model implants can be interpreted as a measure of the potential clinical benefit of anti-Amd prophylaxis. Using a murine model of implant-associated osteomyelitis in which model implant with a defined region of interest, a 0.5×2.0 mm flat face on the implant, the area that was covered with biofilm during a 14-day infection with *S. aureus* was measured. The maximum extent of infection is around 40-50% as observed in FIG. 6A where the mice had been treated with an isotype-matched antibody of irrelevant specificity. MAb Amd1.6, alone or in combination with the anti-Gmd mAb 1C11, reduced the formation of biofilm by about 50% relative to control (FIGS. 6B, 6C, 6E). This degree of reduction in biofilm formation is comparable to that resulting from a genetic deficiency in the autolysin gene (Δatl) (FIGS. 6B, 6D, 6E), indicating that in terms of biofilm formation the internal genetic deletion and interference by the exogenous anti-Amd antibody are functionally equivalent.

Example 10—Passive Immunization with Anti-Amd mAb Amd1.6 Reduces the Volume of Bone Lysis Resulting from the *S. aureus* Infection One of the characteristic features of *S. aureus* infections in bone is the lysis of bone resulting from the inflammatory response elicited by the infecting bacteria. Consequently, reduction in the volume of bone that is lysed (the Osteolytic Volume) is taken as a measure of limitation of the infection. To learn if anti-Amd mAb Amd1.6 would limit bone damage, groups of five 6-10 week old, female Balb/c mice were immunized intraperitoneally with PBS (untreated control), anti-Gmd mAb 1C11, anti-Amd mAb Amd1.6, or a combination (1C11+Amd1.6) at a total dose of 40 mg/kg. Twenty-four hours later each mouse had inserted through its right tibia a pin contaminated with USA300 LAC::lux, a bioluminescent CA-MRSA strain.

Figure 7A:
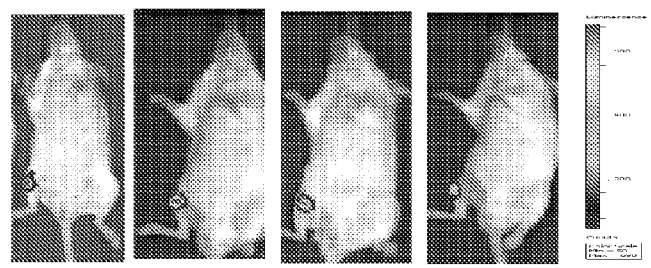
FIGS. 7A-C illustrate the effect of passive immunization with anti-Amd, anti-Gmd, and a combination of anti-Amd and anti-Gmd monoclonal antibodies on the reduction in the amount of bone damage. Female Balb/c mice (n=5) were passively immunized with PBS or anti-Gmd (1C11), anti-Amd (1.6) or a combination (1C11+1.6) at a 40 mg/kg dose i.p. as previously described (Varrone et al., "Passive Immunization With Anti-Glucosaminidase Monoclonal Antibodies Protects Mice From Implant-Associated Osteomyelitis by Mediating Opsonophagocytosis of *Staphylococcus aureus* Megaclusters," *J Orthop Res* 32(10):1389-96 (2014), which is hereby incorporated by reference in its entirety). Twenty-four hours later all mice received a trans-tibial pin contaminated with USA300 LAC::lux, and bioluminescent imaging was performed on Day 3 to confirm the infection (FIG. 7A). The mice were euthanized 14 days after infection, and the tibiae were harvested for micro-CT analysis. Representative 3D renderings of the infected tibiae are shown from the medial and lateral side (FIG. 7B) to illustrate the relative level of osteolysis in each group (B) of the tibias. The osteolytic volume in each tibia was quantified using the formula: Osteolytic volume (mm$^3$)=[medial osteolytic area+lateral osteolytic area (mm$^2$)]×cortical thickness (mm) (*$p<0.05$ vs. PBS). The results are illustrated graphically in FIG. 7C.

Bioluminescent imaging of all mice was performed on Days 0, 3, 5, 7, 10, and 14 using the Xenogen IVIS Spectrum imaging system (Caliper Life Sciences, Hopkinton, Mass.), and the peak BLI on Day 3 was quantified as previously described (Li et al., "Quantitative Mouse Model of Implant-associated Osteomyelitis and the Kinetics of Microbial Growth, Osteolysis, and Humoral Immunity," *J Orthop Res* 26:96-105 (2008), which is hereby incorporated by reference in its entirety). A representative BLI from each treatment group is illustrated in FIG. 7A, indicated that bacterial load was present in each treatment group.

Figure 7B:
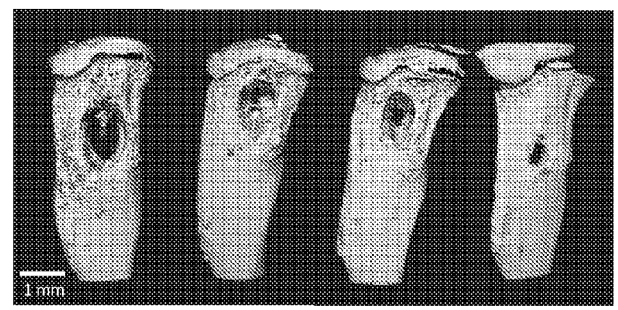
Figure 7C:
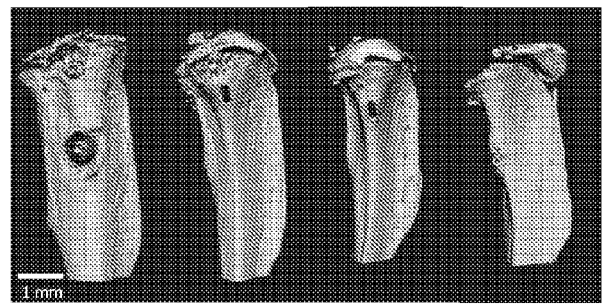
Figure 7C:
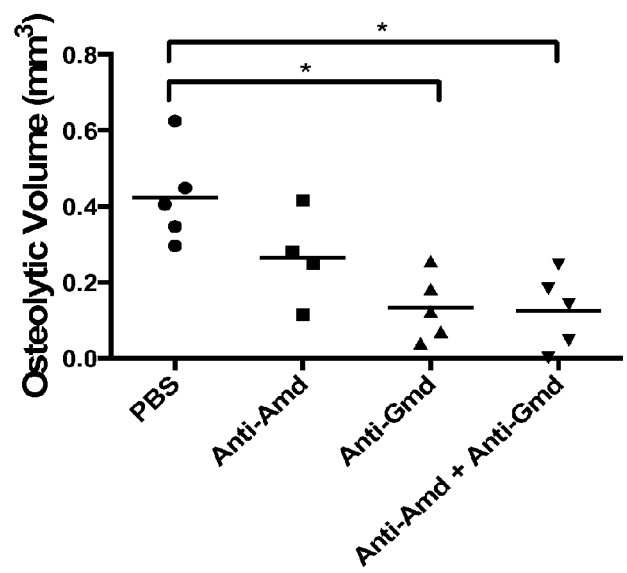

The resulting infection was allowed to progress for fourteen days when the animals were sacrificed and the infected tibiae were harvested for analysis by microCT as previously described (Li et al., "Effects of Antiresorptive Agents on Osteomyelitis: Novel Insights into the Pathogenesis of Osteonecrosis of the Jaw," *Ann N Y Acad Sci* 1192:84-94 (2010), which is hereby incorporated by reference in its entirety). In the untreated control, bone lysis on both the medial and lateral sides was extensive (FIG. 7B); Osteolytic Volume averaged over 0.4 mm$^3$. Reductions in Osteolytic Volume were measured in all three groups of antibody-treated mice (FIG. 7C). In one individual receiving the combination therapy, the Osteolytic Volume was calculated to be 0, indicating a complete healing of the infected implant site. The effect of the combined antibody therapy in this individual is equivalent to both a sterile pin and an infected pin that was cured with effective antibiotic therapy (i.e., gentamicin treatment in Li et al., "Quantitative Mouse Model of Implant-Associated Osteomyelitis and the Kinetics of Microbial Growth, Osteolysis, and Humoral Immunity," *J Orthop Res* 26:96-105 (2008), which is hereby incorporated by reference in its entirety). It is believed that this individual represents the first ever successful healing of an infected implant site in the absence of antibiotic therapy.

Example 11—Passive Immunization with Anti-Amd mAb Amd1.6 Significantly Reduces Bacterial Spread The formation of abscesses is another indication of the severity of infection. The number of abscesses formed was measured in the same mice examined in Example 10. Histological sections were stained with Orange G/alcian blue (ABG/OH) which reveals abscesses as circular fields of inflammatory host cells delimited by an unstained zone and, sometimes, a densely red staining nidus at its center. Typically, the nidus is the Staphylococcal abscess community (SAC); the inflammatory cells are neutrophils, mostly dead near the center and mostly alive near the perimeter and the unstained zone is a capsule formed from fibrin. In the untreated mice multiple abscesses formed (FIG. 8A) with an average of nearly 4.5 per tibia (FIG. 8C). In contrast mAb Amd1.6-treated mice averaged only two abscesses as did those treated with the anti-Gmd mAb 1C11 or with the combination (FIGS. 8B, 8C).

Example 12—Passive Immunization with Anti-Amd mAb Amd1.6 Alone or in Combination with Anti-Gmd 1C11 Promotes the Formation of Sterile Abscesses and Accelerates Bone Healing Detailed examination of the same histological sections presented in FIG. 8B revealed unexpected findings. Consistently, intramedullary gram-stained abscesses were only found in tibiae of the PBS-treated mice (FIGS. 9A-B), while the lesions in the tibiae of the anti-Atl treated mice were characteristic of sterile abscesses that did not contain gram-positive bacteria (FIGS. 9C-H). Moreover, while the lesions in the tibiae of the placebo treated mice had clear histologic features of Staphylococci abscess communities (SACs) (Cheng et al., "Genetic Requirements for *Staphylococcus aureus* Abscess Formation and Persistence in Host Tissues," *FASEB J* 23(10):3393-3404 (2009); Cheng et al., "Contribution of Coagulases Towards *Staphylococcus aureus* Disease and Protective Immunity," *PLoS Pathog* 6(8):e1001036 (2010), each of which is hereby incorporated by reference in its entirety), no SACs were observed in the tibiae of anti-Atl treated mice (compare FIGS. 10A-B with FIGS. 10C-H). Finally, and most surprisingly, it was discovered that combined anti-Amd and anti-Gmd passive immunization not only clears the MRSA infection (confirmed to be metabolically active on day 3; FIG. 7A) by day 14, but also allows for bone healing that has never been documented to occur in this murine model of implant-associated osteomyelitis (compare FIGS. 11A-C). Specifically, osseus integration of the *S. aureus* contaminated implant is documented in FIG. 11B, which displays a similar level of new bone formation around the pin and cortex as that observed in a sterile pin control (FIG. 11C). Using arginase-1-positive staining, the presence or absence of tissue healing M2 macrophages was also analyzed. M2 macrophages, which are unable to enter the SAC in the tibia of PBS treated mice (FIG. 11D), extensively invade the sterile abscesses in the tibia of combined anti-Amd and anti-Gmd treated mice to facilitate classical tissue healing (FIG. 11E) (Murray and Wynn, "Protective and Pathogenic Functions of Macrophage Subsets," *Nat Rev Immunol* 11(11):723-737 (2011), which is hereby incorporated by reference in its entirety).

Example 13—Generation of Humanized Anti-Amd mAb Amd1.6

The variable regions of the light and heavy chains of the Amd1.6 antibody will be PCR amplified using primers to permit cloning into the human antibody expression vectors described by Tiller et al. ("Efficient Generation of Monoclonal Antibodies from Single Human B Cells by Single Cell RT-PCR and Expression Vector Cloning," *J. Immunol. Methods* 329(1-2):112-24 (2008), which is hereby incorporated by reference in its entirety). Plasmids containing the Amd1.6 light and heavy chain variable regions and human kappa and IgG1 constant regions will be prepared and co-transfected into HEK293 cells. After 3 days, the medium will be removed from the cells and assayed for the presence of human IgG and for binding to immobilized Amd protein by ELISA. Bound antibody will be detected using a goat anti-Human IgG antibody coupled to horseradish peroxidase and 3,3',5,5' tetramethylbenzidene substrate.

To establish that the human:mouse chimeric Amd1.6 reacted with Amd as well as the parental mouse Amd1.6, each will be tested for its ability to inhibit the enzymatic activity of His-Amd.

The humanized Amd1.6 antibody can be utilized in a phase I clinical trial in elderly patients (>65 yrs) undergoing primary total joint replacement. The humanized Amd1.6 antibody will be used alone and in combination with a humanized 1C11 anti-Gmd antibody as described in U.S.

Patent Application Publ. No. 20130110249, which is hereby incorporated by reference in its entirety.

Example 14—Generation of Humanized Anti-Amd mAb Amd2.1

The variable regions of the light and heavy chains of the Amd2.1 antibody will be PCR amplified using primers to permit cloning into the human antibody expression vectors described by Tiller et al. ("Efficient Generation of Monoclonal Antibodies from Single Human B Cells by Single Cell RT-PCR and Expression Vector Cloning," *J. Immunol. Methods* 329(1-2):112-24 (2008), which is hereby incorporated by reference in its entirety). Plasmids containing the Amd2.1 light and heavy chain variable regions and human kappa and IgG1 constant regions will be prepared and co-transfected into HEK293 cells. After 3 days, the medium will be removed from the cells and assayed for the presence of human IgG and for binding to immobilized Amd protein by ELISA. Bound antibody will be detected using a goat anti-Human IgG antibody coupled to horseradish peroxidase and 3,3',5,5' tetramethylbenzidene substrate.

To establish that the human:mouse chimeric Amd2.1 reacted with Amd as well as the parental mouse Amd2.1, each will be tested for its ability to inhibit the enzymatic activity of His-Amd.

The humanized Amd2.1 antibody can be utilized in a phase I clinical trial in elderly patients (>65 yrs) undergoing primary total joint replacement. The humanized Amd2.1 antibody will be used alone and in combination with a humanized 1C11 anti-Gmd antibody as described in U.S. Patent Application Publ. No. 20130110249, which is hereby incorporated by reference in its entirety.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated humanized monoclonal antibody, or antigen binding portion thereof, that binds specifically to a *Staphylococcus aureus* autolysin N-acetylmuramoyl-L-alanine amidase (Amd) and comprises the complementarity determining region sequences of the $V_H$ domain of SEQ ID NO: 11 and the $V_L$ domain of SEQ ID NO: 37.

2. The monoclonal antibody or antigen binding portion according to claim 1, which binds Amd comprising the amino acid sequence of SEQ ID NO: 1.

3. The monoclonal antibody or antigen binding portion according to claim 1, wherein the antibody or antigen binding portion inhibits in vivo growth of *S. aureus*.

4. The monoclonal antibody or antigen binding portion according to claim 1 that binds to Amd and inhibits Amd catalytic activity.

5. The antigen binding portion according to claim 1.

6. The antigen binding portion according to claim 1, wherein the antigen binding portion comprises a Fab fragment, Fv fragment, or single-chain antibody.

7. The monoclonal antibody or antigen binding portion according to claim 1, which comprises the sequences of SEQ ID NOS:65-67 and the sequences of SEQ ID NOS:68 and 69.

8. A cell line that expresses a monoclonal antibody or an antigen binding portion according to claim 1.

9. A pharmaceutical composition comprising a carrier and one or more monoclonal antibodies or one or more antigen binding portions according to claim 1.

10. The pharmaceutical composition according to claim 9 further comprising an antibiotic agent or immunotherapeutic agent.

11. The pharmaceutical composition according to claim 10, wherein the immunotherapeutic agent is a second monoclonal antibody or binding portion thereof that binds specifically to a *Staphylococcus* glucosaminidase (Gmd) and inhibits in vivo growth of a *Staphylococcus* strain.

12. A method of introducing an orthopedic implant, graft or medical device into a patient comprising:
   administering to a patient in need of an orthopedic implant, graft or medical device an effective amount of a monoclonal antibody or an antigen binding portion according to claim 1;
   introducing the orthopedic implant, graft or medical device into the patient.

13. The method according to claim 12, further comprising repeating said administering prior to said introducing or after said introducing, or administering a second therapeutic agent to the patient, wherein the second therapeutic agent is an antibiotic agent or immunotherapeutic agent.

14. The method according to claim 12, wherein said administering is carried out systemically or directly to a site of implantation.

15. The method according to claim 12, wherein the orthopedic implant is introduced, and the orthopedic implant is a joint prosthesis, graft or synthetic implant.

16. The method according to claim 12, wherein the graft or medical device is introduced, and the medical device is a cardiac pacemaker, cerebrospinal fluid shunt, dialysis catheter, or prosthetic heart valve.

17. The method according to claim 13, wherein the immunotherapeutic agent is a second monoclonal antibody or binding portion thereof that binds specifically to a *Staphylococcus* glucosaminidase (Gmd) and inhibits in vivo growth of a *Staphylococcus* strain.

18. The method according to claim 12, wherein the patient is a human or a non-human mammal.

19. A method of treating or preventing a *Staphylococcus* infection comprising:
   administering to a patient susceptible to or having a *Staphylococcus* infection an effective amount of the monoclonal antibody or antigen binding portion according to claim 1.

20. The method according to claim 19, further comprising repeating said administering or administering a second therapeutic agent to the patient, wherein the second therapeutic agent is an antibiotic agent or immunotherapeutic agent.

21. The method according to claim 19, wherein said administering is carried out systemically or directly to a site of *Staphylococcus* infection.

22. The method according to claim 21, wherein the site of *Staphylococcus* infection includes the nervous system, skin, muscle, cardiac, respiratory tract, gastrointestinal, eye, kidney and urinary tract, or bone and joint infections.

23. The method according to claim 20, wherein the immunotherapeutic agent is a second monoclonal antibody or binding portion thereof that binds specifically to a *Staphylococcus* glucosaminidase (Gmd) and/or inhibits in vivo growth of a *Staphylococcus* strain.

24. The method according to claim 19, wherein the patient is a human or a non-human mammal.

25. The method according to claim 19, wherein the *Staphylococcus* strain is *S. aureus*.

26. The method according to claim 19, wherein said administering is effective to reduce the rate of infection, the severity of infection, the duration of infection, or any combination thereof; reduce or altogether eliminate the total number of abscesses, and/or increase the number of sterile abscesses.

27. A method of treating osteomyelitis comprising:
   administering to a patient having a *Staphylococcus aureus* bone or joint infection an effective amount of a monoclonal antibody according to claim 1, or an antigen Amd binding portion thereof.

28. The method according to claim 27, further comprising repeating said administering or administering a second therapeutic agent to the patient, wherein the second therapeutic agent is an antibiotic agent or immunotherapeutic agent.

29. The method according to claim 27, wherein said administering is carried out systemically or directly to a site of the *S. aureus* bone or joint infection.

30. The method according to claim 28, wherein the immunotherapeutic agent is a second monoclonal antibody or binding portion thereof that binds specifically to a *Staphy-* lococcus glucosaminidase (Gmd) and inhibits in vivo growth of *Staphylococcus aureus*.

31. The method according to claim 27, wherein the patient is a human or a non-human mammal.

32. The method according to claim 27, wherein said administering is effective to partially or completely heal an osteolytic lesion.

33. The method according to claim 12, wherein the administered antibody or antigen binding portion comprises the sequences of SEQ ID NOS:65-67 and the sequences of SEQ ID NOS:68 and 69.

34. The method according to claim 12, wherein the patient is older than 50 years of age or immunocompromised.

35. The method according to claim 12, wherein the orthopedic implant is a joint prosthesis for revision total joint replacement, said method further comprising: removing an infected joint prosthesis from the patient and treating the patient for the infection prior to said introducing the orthopedic implant into the patient.

36. The method according to claim 13, wherein the antibiotic agent is selected from the group consisting of vancomycin, tobramycin, cefazolin, erythromycin, clindamycin, rifampin, gentamycin, fusidic acid, minocycline, co-trimoxazole, linezolid, quinupristin-dalfopristin, daptomycin, tigecycline, dalbavancin, telavancin, oritavancin, ceftobiprole, ceftaroline, iclaprim, and the carbapenem CS-023/RO-4908463.

37. The method according to claim 19, wherein the administered antibody or antigen binding portion comprises the sequences of SEQ ID NOS:65-67 and the sequences of SEQ ID NOS:68 and 69.

38. The method according to claim 19, wherein the patient is older than 50 years of age or immunocompromised.

39. The method according to claim 20, wherein the antibiotic agent is selected from the group consisting of vancomycin, tobramycin, cefazolin, erythromycin, clindamycin, rifampin, gentamycin, fusidic acid, minocycline, co-trimoxazole, linezolid, quinupristin-dalfopristin, daptomycin, tigecycline, dalbavancin, telavancin, oritavancin, ceftobiprole, ceftaroline, iclaprim, and the carbapenem CS-023/RO-4908463.

40. The method according to claim 27, wherein the administered antibody or antigen binding portion comprises the sequences of SEQ ID NOS:65-67 and the sequences of SEQ ID NOS:68 and 69.

41. The method according to claim 28, wherein the antibiotic agent is selected from the group consisting of vancomycin, tobramycin, cefazolin, erythromycin, clindamycin, rifampin, gentamycin, fusidic acid, minocycline, co-trimoxazole, linezolid, quinupristin-dalfopristin, daptomycin, tigecycline, dalbavancin, telavancin, oritavancin, ceftobiprole, ceftaroline, iclaprim, and the carbapenem CS-023/RO-4908463.

* * * * *

UNITED STATES PATENT AND TRADEMARK OFFICE
CERTIFICATE OF CORRECTION

PATENT NO. : 10,100,127 B2
APPLICATION NO. : 15/104104
DATED : October 16, 2018
INVENTOR(S) : Daiss et al.

Page 1 of 1

It is certified that error appears in the above-identified patent and that said Letters Patent is hereby corrected as shown below:

In the Claims

Claim 27, Column 122, Line 56, delete "Amd".

Signed and Sealed this
Fourth Day of December, 2018

Andrei Iancu
*Director of the United States Patent and Trademark Office*

SEQUENCE LISTING

<160> NUMBER OF SEQ ID NOS: 79

<210> SEQ ID NO 1
<211> LENGTH: 585
<212> TYPE: PRT
<213> ORGANISM: Artificial
<220> FEATURE:
<223> OTHER INFORMATION: His-labeled, N-acetylmuramoyl-L-alanine amidase
      from Staphylococcus aureus

<400> SEQUENCE: 1

Met His His His His His His Ser Ala Ser Ala Gln Pro Arg Ser Val
1               5                   10                  15

Ala Ala Thr Pro Lys Thr Ser Leu Pro Lys Tyr Lys Pro Gln Val Asn
            20                  25                  30

Ser Ser Ile Asn Asp Tyr Ile Arg Lys Asn Asn Leu Lys Ala Pro Lys
        35                  40                  45

Ile Glu Glu Asp Tyr Thr Ser Tyr Phe Pro Lys Tyr Ala Tyr Arg Asn
    50                  55                  60

Gly Val Gly Arg Pro Glu Gly Ile Val Val His Asp Thr Ala Asn Asp
65                  70                  75                  80

Arg Ser Thr Ile Asn Gly Glu Ile Ser Tyr Met Lys Asn Asn Tyr Gln
                85                  90                  95

Asn Ala Phe Val His Ala Phe Val Asp Gly Asp Arg Ile Ile Glu Thr
            100                 105                 110

Ala Pro Thr Asp Tyr Leu Ser Trp Gly Val Gly Ala Val Gly Asn Pro
        115                 120                 125

Arg Phe Ile Asn Val Glu Ile Val His Thr His Asp Tyr Ala Ser Phe
    130                 135                 140

Ala Arg Ser Met Asn Asn Tyr Ala Asp Tyr Ala Ala Thr Gln Leu Gln
145                 150                 155                 160

Tyr Tyr Gly Leu Lys Pro Asp Ser Ala Glu Tyr Asp Gly Asn Gly Thr
                165                 170                 175

Val Trp Thr His Tyr Ala Val Ser Lys Tyr Leu Gly Gly Thr Asp His
            180                 185                 190

Ala Asp Pro His Gly Tyr Leu Arg Ser His Asn Tyr Ser Tyr Asp Gln
        195                 200                 205

Leu Tyr Asp Leu Ile Asn Glu Lys Tyr Leu Ile Lys Met Gly Lys Val

Ala Pro Trp Gly Thr Gln Ser Thr Thr Thr Pro Thr Thr Pro Ser Lys
225                 230                 235                 240

Pro Thr Thr Pro Ser Lys Pro Ser Thr Gly Lys Leu Thr Val Ala Ala
            245                 250                 255

Asn Asn Gly Val Ala Gln Ile Lys Pro Thr Asn Ser Gly Leu Tyr Thr
        260                 265                 270

Thr Val Tyr Asp Lys Thr Gly Lys Ala Thr Asn Glu Val Gln Lys Thr
    275                 280                 285

Phe Ala Val Ser Lys Thr Ala Thr Leu Gly Asn Gln Lys Phe Tyr Leu
290                 295                 300

Val Gln Asp Tyr Asn Ser Gly Asn Lys Phe Gly Trp Val Lys Glu Gly
305                 310                 315                 320

Asp Val Val Tyr Asn Thr Ala Lys Ser Pro Val Asn Val Asn Gln Ser
                325                 330                 335

Tyr Ser Ile Lys Pro Gly Thr Lys Leu Tyr Thr Val Pro Trp Gly Thr
            340                 345                 350

Ser Lys Gln Val Ala Gly Ser Val Ser Gly Ser Gly Asn Gln Thr Phe
        355                 360                 365

Lys Ala Ser Lys Gln Gln Gln Ile Asp Lys Ser Ile Tyr Leu Tyr Gly
    370                 375                 380

Ser Val Asn Gly Lys Ser Gly Trp Val Ser Lys Ala Tyr Leu Val Asp
385                 390                 395                 400

Thr Ala Lys Pro Thr Pro Thr Pro Thr Pro Lys Pro Ser Thr Pro Thr
                405                 410                 415

Thr Asn Asn Lys Leu Thr Val Ser Ser Leu Asn Gly Val Ala Gln Ile
            420                 425                 430

Asn Ala Lys Asn Asn Gly Leu Phe Thr Thr Val Tyr Asp Lys Thr Gly
        435                 440                 445

Lys Pro Thr Lys Glu Val Gln Lys Thr Phe Ala Val Thr Lys Glu Ala
    450                 455                 460

Ser Leu Gly Gly Asn Lys Phe Tyr Leu Val Lys Asp Tyr Asn Ser Pro
465                 470                 475                 480

Thr Leu Ile Gly Trp Val Lys Gln Gly Asp Val Ile Tyr Asn Asn Ala
                485                 490                 495

Lys Ser Pro Val Asn Val Met Gln Thr Tyr Thr Val Lys Pro Gly Thr
            500                 505                 510

Lys Leu Tyr Ser Val Pro Trp Gly Thr Tyr Lys Gln Glu Ala Gly Ala
    515                 520                 525

Val Ser Gly Thr Gly Asn Gln Thr Phe Lys Ala Thr Lys Gln Gln Gln
530                 535                 540

Ile Asp Lys Ser Ile Tyr Leu Phe Gly Thr Val Asn Gly Lys Ser Gly
545                 550                 555                 560

Trp Val Ser Lys Ala Tyr Leu Ala Val Pro Ala Ala Pro Lys Lys Ala
                565                 570                 575

Val Ala Gln Pro Lys Thr Ala Val Lys
            580                 585

<210> SEQ ID NO 2
<211> LENGTH: 1755
<212> TYPE: DNA
<213> ORGANISM: Artificial
<220> FEATURE:
<223> OTHER INFORMATION: Nucleic acid encoding His-labeled,
      N-acetylmuramoyl-L-alanine amidase from Staphylococcus aureus

<400> SEQUENCE: 2

```
atgcaccatc accaccacca cagcgcaagc gcacagcctc gttccgtcgc cgccaccccg      60
aaaaccagct tgccgaagta caaaccgcaa gttaatagca gcatcaacga ctacatccgc     120
aaaaacaacc tgaaggcccc gaaaattgaa gaggactata ccagctattt cccgaaatat     180
gcttaccgta atggtgtcgg tcgtccggag ggtattgtgg tccacgacac cgcgaatgac     240
cgtagcacca tcaacggtga gattagctac atgaaaaaca attaccaaaa cgcgttcgtg     300
cacgccttcg tcgatggcga tcgcatcatc gaaaccgcgc aaccgactac tctgtcctgg     360
ggtgtgggtg ccgttggcaa cccgcgtttc atcaatgtgg agattgttca tacccacgac     420
tacgcgagct ttgcacgtag catgaacaac tacgccgatt atgctgcaac gcagctgcag     480
tactacggcc tgaaaccgga tagcgcggag tatgacggta acggtacggt gtggacgcat     540
tatgcggtga gcaaatacct gggtggtacc gatcatgctg atccgcatgg ctacctgcgc     600
tctcacaact atagctacga ccagttgtac gacctgatca tgagaaaata tctgattaag     660
atgggtaagg ttgcaccgtg gggtacgcag agcaccacga cgccgaccac gccgagcaaa     720
ccgacgaccc cgtccaaacc gtctaccggc aaactgacgg tcgcggctaa taacggtgtc     780
gcgcagatta aaccgaccaa cagcggtctg tacaccaccg tctatgataa acgggcaaa      840
gccaccaatg aggttcaaaa gacgttcgca gttagcaaaa cggcgaccct gggtaaccaa     900
aagttctacc tggttcagga ttacaatagc ggcaacaaat ttggttgggt gaaagaaggc     960
gacgttgtgt acaataccgc gaagtccccg gtgaacgtta atcagagcta tagcatcaag    1020
ccgggtacca aattgtatac ggtgccgtgg ggtaccagca agcaagttgc gggtagcgtc    1080
agcggctctg gtaaccagac cttcaaggcg ctctaagcaac aacaaattga caaaagcatt    1140
tacctgtatg gtagcgttaa tggtaaaagc ggctgggtgt ctaaagcgta tctggtcgac    1200
accgcaaagc cgacgccaac gccgaccccg aagccgagca ccccaaccac caacaacaag    1260
ctgacggtca gctccctgaa tggtgttgcg caaatcaatg cgaagaataa tggcctgttt    1320
accaccgttt acgataagac gggcaagcca acgaaagaag tccagaaaac ctttgctgtc    1380
accaaagaag ccagcctggg cggtaacaag ttctatctgg ttaaggacta caactccccg    1440
acgctgatcg gttgggtcaa acaaggcgat gtcatttaca ataacgcgaa aagcccggtt    1500
aatgtgatgc aaacctatac cgtcaaaccg ggtacgaagc tgtattccgt tccgtggggc    1560
acgtacaaac aagaagcagg cgcggtgagc ggtaccggca atcagacctt aaggccacc    1620
aagcagcagc agatcgataa atctatttac ttgtttggca ccgtgaatgg caagagcggt    1680
tgggtttcta aggcatacct ggcggtgccg gcagcaccga gaaggcggt ggcgcagcca    1740
aagaccgcag tgaag                                                    1755
```

<210> SEQ ID NO 3
<211> LENGTH: 251
<212> TYPE: PRT
<213> ORGANISM: Artificial
<220> FEATURE:
<223> OTHER INFORMATION: His-labeled, N-acetylmuramoyl-L-alanine amidase catalytic domain from Staphylococcus aureus

<400> SEQUENCE: 3

```
Met His His His His His His Ser Ala Ser Ala Gln Pro Arg Ser Val
1               5                   10                  15

Ala Ala Thr Pro Lys Thr Ser Leu Pro Lys Tyr Lys Pro Gln Val Asn
            20                  25                  30
```

```
Ser Ser Ile Asn Asp Tyr Ile Arg Lys Asn Asn Leu Lys Ala Pro Lys
        35                  40                  45

Ile Glu Glu Asp Tyr Thr Ser Tyr Phe Pro Lys Tyr Ala Tyr Arg Asn
 50                  55                  60

Gly Val Gly Arg Pro Glu Gly Ile Val Val His Asp Thr Ala Asn Asp
 65                  70                  75                  80

Arg Ser Thr Ile Asn Gly Glu Ile Ser Tyr Met Lys Asn Asn Tyr Gln
                 85                  90                  95

Asn Ala Phe Val His Ala Phe Val Asp Gly Asp Arg Ile Ile Glu Thr
            100                 105                 110

Ala Pro Thr Asp Tyr Leu Ser Trp Gly Val Gly Ala Val Gly Asn Pro
        115                 120                 125

Arg Phe Ile Asn Val Glu Ile Val His Thr His Asp Tyr Ala Ser Phe
    130                 135                 140

Ala Arg Ser Met Asn Asn Tyr Ala Asp Tyr Ala Ala Thr Gln Leu Gln
145                 150                 155                 160

Tyr Tyr Gly Leu Lys Pro Asp Ser Ala Glu Tyr Asp Gly Asn Gly Thr
                165                 170                 175

Val Trp Thr His Tyr Ala Val Ser Lys Tyr Leu Gly Gly Thr Asp His
            180                 185                 190

Ala Asp Pro His Gly Tyr Leu Arg Ser His Asn Tyr Ser Tyr Asp Gln
        195                 200                 205

Leu Tyr Asp Leu Ile Asn Glu Lys Tyr Leu Ile Lys Met Gly Lys Val
    210                 215                 220

Ala Pro Trp Gly Thr Gln Ser Thr Thr Thr Pro Thr Thr Pro Ser Lys
225                 230                 235                 240

Pro Thr Thr Pro Ser Lys Pro Ser Thr Gly Lys
                245                 250
```

<210> SEQ ID NO 4
<211> LENGTH: 753
<212> TYPE: DNA
<213> ORGANISM: Artificial
<220> FEATURE:
<223> OTHER INFORMATION: Nucleic acid encoding His-labeled,
    N-acetylmuramoyl-L-alanine amidase catalytic domain from
    Staphylococcus aureus

<400> SEQUENCE: 4

```
atgcaccatc accaccacca cagcgcaagc gcacagcctc gttccgtcgc cgccaccccg      60
aaaccagct tgccgaagta caaaccgcaa gttaatagca gcatcaacga ctacatccgc     120
aaaaacaacc tgaaggcccc gaaaattgaa aggactata ccagctattt cccgaaatat     180
gcttaccgta tggtgtcgg tcgtccggag ggtattgtgg tccacgacac cgcgaatgac     240
cgtagcacca tcaacggtga gattagctac atgaaaaaca attaccaaaa cgcgttcgtg     300
cacgccttcg tcgatggcga tcgcatcatc gaaaccgcgc caaccgacta tctgtcctgg     360
ggtgtgggtg ccgttggcaa cccgcgtttc atcaatgtgg agattgttca tacccacgac     420
tacgcgagct ttgcacgtag catgaacaac tacgccgatt atgctgcaac gcagctgcag     480
tactacggcc tgaaaccgga tagcgcggag tatgacggta acggtacggt gtggacgcat     540
tatgcggtga gcaaatacct gggtggtacc gatcatgctg atccgcatgg ctacctgcgc     600
tctcacaact atagctacga ccagttgtac gacctgatca tgagaaata tctgattaag     660
atgggtaagg ttgcaccgtg gggtacgcag agcaccacga cgccgaccac gccgagcaaa     720
```
ccgacgaccc cgtccaaacc gtctaccggc aaa                                753

<210> SEQ ID NO 5
<211> LENGTH: 111
<212> TYPE: PRT
<213> ORGANISM: Mus musculus
<220> FEATURE:
<221> NAME/KEY: misc_feature
<222> LOCATION: (83)..(83)
<223> OTHER INFORMATION: Xaa can be any naturally occurring amino acid

<400> SEQUENCE: 5

Pro Glu Leu Val Lys Pro Gly Ala Ser Val Lys Met Ser Cys Lys Ala
1               5                   10                  15

Ser Gly Tyr Thr Phe Thr Ser Tyr Ile Met His Trp Val Lys Gln Lys
            20                  25                  30

Pro Gly Gln Gly Leu Glu Trp Ile Gly Tyr Ile Asn Pro Tyr Asn Asp
        35                  40                  45

Gly Thr Lys Tyr Asn Glu Lys Phe Lys Gly Lys Ala Thr Leu Thr Ser
    50                  55                  60

Asp Lys Ser Ser Thr Thr Ala Tyr Met Glu Leu Ser Ser Leu Thr Ser
65                  70                  75                  80

Glu Asp Xaa Ala Val Tyr Tyr Cys Ala Arg Leu Asp Gly Tyr Tyr Asp
                85                  90                  95

Cys Phe Asp Tyr Trp Gly Gln Gly Thr Thr Leu Thr Val Ser Ser
            100                 105                 110

<210> SEQ ID NO 6
<211> LENGTH: 425
<212> TYPE: DNA
<213> ORGANISM: Mus musculus
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t

<400> SEQUENCE: 6
cctgagctgg taaagcctgg ggcttcagtg aagatgtcct gcaaggcttc tggatacaca     60
ttcactagct atattatgca ctgggtgaag cagaagcctg gcagggcct tgagtggatt    120 ggatatatta atccttacaa tgatggtact aagtacaatg agaagttcaa aggcaaggcc   180
acactgactt cagacaaatc ctccaccaca gcctacatgg agctcagcag cctgacctct   240
gaggactntg cggtctatta ctgtgcaaga cttgatggtt actacgactg ctttgactac   300
tggggccaag gcaccactct cacagtctcn tcagccaaaa cgacaccccc atctgtctat   360
ccactggccc ctggatctgc tgcccaaact aactccatgg tgaccctggg atgccnggtc   420
aaggg                                                              425

<210> SEQ ID NO 7
<211> LENGTH: 116
<212> TYPE: PRT
<213> ORGANISM: Mus musculus

<400> SEQUENCE: 7

```
Gln Gln Ser Gly Ala Glu Leu Val Lys Pro Gly Ala Ser Val Lys Leu
1               5                   10                  15

Ser Cys Thr Ala Ser Gly Phe Asn Ile Lys Asp Thr Tyr Ile His Trp
            20                  25                  30

Val Lys Gln Arg Pro Glu Gln Gly Leu Glu Trp Ile Gly Arg Ile Asp
        35                  40                  45

Pro Ala Asn Gly Ile Thr Asn Tyr Asp Pro Lys Phe Gln Gly Arg Ala
    50                  55                  60

Thr Ile Thr Ala Asp Thr Ser Ser Asn Ile Ala Tyr Leu Gln Leu Thr
65                  70                  75                  80

Ser Leu Thr Ser Glu Gly Thr Ala Val Tyr Tyr Cys Ala Arg Gly Gly
                85                  90                  95

Tyr Leu Ser Pro Tyr Ala Met Asp Tyr Trp Gly Gln Gly Thr Ser Val
            100                 105                 110

Thr Val Ser Ser
        115
```

<210> SEQ ID NO 8
<211> LENGTH: 460
<212> TYPE: DNA
<213> ORGANISM: Mus musculus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t

<400> SEQUENCE: 8

```
ntgcagcagt ctggggcaga gcttgtgaag ccaggggcct cagtcaagtt gtcctgcaca      60
gcttctggct tcaacattaa agacacctat atacattggg tgaagcagag gcctgaacag     120
ggcctggagt ggattggaag gattgatcct gcgaatggta ttactaatta tgacccgaag     180
ttccagggca gggccactat aacagcagac acatcctcca atatagccta cctgcagctc     240
accagcctga catctgaggg cactgccgtc tactactgtg ctagaggggg ttacctatcc     300
ccttatgcta tggactactg gggtcaagga acctcagtca ccgtctcctc agccaaaacg     360
acacccccat ctgtctatcc actggcccct ggatctgctg cccaaactaa ctccatggtg     420
accctgggat gcctggtcaa gggctattnc cctgagccag                           460
```

<210> SEQ ID NO 9
<211> LENGTH: 118
<212> TYPE: PRT
<213> ORGANISM: Mus musculus

<400> SEQUENCE: 9

```
Gln Gln Ser Gly Ala Glu Leu Val Arg Pro Gly Ala Leu Val Lys Leu
1               5                   10                  15

Ser Cys Lys Ala Ser Gly Phe Asn Ile Gln Asp Tyr Tyr Leu His Trp
            20                  25                  30

Met Lys Gln Arg Pro Glu Gln Gly Leu Glu Trp Ile Gly Trp Ile Asp
        35                  40                  45

Pro Glu Asn Asp Asn Thr Val Tyr Asp Pro Lys Phe Arg Asp Arg Ala
    50                  55                  60

Ser Leu Thr Ala Asp Thr Phe Ser Asn Thr Ala Tyr Leu Gln Leu Ser
65                  70                  75                  80
```

```
Gly Leu Thr Ser Glu Asp Thr Ala Val Tyr Tyr Cys Ala Arg Arg Asp
                85                  90                  95

Gly Ile Thr Thr Ala Thr Arg Ala Met Asp Tyr Trp Gly Gln Gly Thr
            100                 105                 110

Ser Val Thr Val Ser Ser
        115

<210> SEQ ID NO 10
<211> LENGTH: 464
<212> TYPE: DNA
<213> ORGANISM: Mus musculus
<220> FEATURE:
<221> NAME/KEY: misc_feature
<222> LOCATION: (450)..(454)
<223> OTHER INFORMATION: n is a, c, g, or t

<400> SEQUENCE: 10
tgcagcagtc tggggctgag cttgtgaggc caggggcctt agtcaaattg tcctgcaaag      60
cttctggctt caacattcaa gactactatc tacactggat gaaacagagg cctgagcagg     120
gcctggagtg gattggatgg attgatcctg agaatgataa tactgtatat gacccgaagt     180
tccgggacag ggccagttta acagcagaca cattttccaa cacagcctac ctacagctca     240
gcggcctgac atctgaagac actgccgtct attactgtgc tagaagagac ggcattacta     300
cggctacgcg ggctatggac tactggggtc aaggaacctc agtcaccgtc tcctcagcca     360
aaacgacacc cccatctgtc tatccactgg cccctggatc tgctgcccaa actaactcca     420
tggtgaccct gggatgcctg gtcaagggcn nnncctgag ccag                       464

<210> SEQ ID NO 11
<211> LENGTH: 112
<212> TYPE: PRT
<213> ORGANISM: Mus musculus

<400> SEQUENCE: 11

Gln Ser Gly Thr Val Leu Ala Arg Pro Gly Thr Ser Val Lys Met Ser
1               5                   10                  15

Cys Lys Ala Ser Gly Tyr Ser Phe Thr Asn Tyr Trp Met His Trp Val
            20                  25                  30

Arg Gln Arg Pro Gly Gln Gly Leu Glu Trp Ile Gly Ser Ile Tyr Pro
        35                  40                  45

Gly Asn Ser Asp Thr Thr Tyr Asn Gln Lys Phe Lys Asp Lys Ala Lys
    50                  55                  60

Leu Thr Ala Val Thr Ser Ala Ser Thr Ala Tyr Met Glu Leu Ser Ser
65                  70                  75                  80

Leu Thr Asn Glu Asp Ser Ala Val Tyr Tyr Cys Thr Gly Asp Asp Tyr
                85                  90                  95

Ser Arg Phe Ser Tyr Trp Gly Gln Gly Thr Leu Val Thr Val Ser Ala
            100                 105                 110

<210> SEQ ID NO 12
<211> LENGTH: 444
<212> TYPE: DNA
<213> ORGANISM: Mus musculus
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
```

```
<220> FEATURE:
<221> NAME/KEY: misc_feature
<222> LOCATION: (438)..(438)
<223> OTHER INFORMATION: n is a, c, g, or t

<400> SEQUENCE: 12
cagtctggga ctgtactggc aaggcctggg acttccgtga agatgtcctg caaggcttct    60
ggctacagct ttaccaacta ctggatgcac tgggtaagac agaggcctgg acagggtcta   120
gaatggattg gttctattta tcctggaaat agtgatacta cctacaacca gaagttcaag   180
gacaaggcca aactgactgc agtcacatcc gccagcactg cctacatgga gctcagcagc   240
ctgacaaatg aggactctgc ggtctattac tgtacggggg atgattactc tcggttttct   300
tactggggcc aagggactct ggtcactgtc tctgcagcca aaacgacacc cccatctgtc   360
tatccactgg cccctggatc tgctgcccaa actaactcca tggtgaccct gggatgcctn   420
gtcaagggct nttttcccnga gcca                                         444

<210> SEQ ID NO 13
<211> LENGTH: 112
<212> TYPE: PRT
<213> ORGANISM: Mus musculus

<400> SEQUENCE: 13

Gln Gln Ser Gly Pro Glu Leu Val Lys Pro Gly Ala Ser Val Lys Ile
1               5                   10                  15

Ser Cys Lys Ala Ser Gly Tyr Thr Phe Thr Asp Tyr Asn Met His Trp
            20                  25                  30

Val Lys Gln Ser His Gly Lys Ser Leu Glu Trp Ile Gly Tyr Ile Phe
        35                  40                  45

Pro Tyr Asn Gly Asp Thr Asp Tyr Asn Gln Lys Phe Lys Asn Lys Ala
    50                  55                  60

Thr Leu Thr Val Asp Asn Ser Ser Ser Thr Ala Tyr Met Asp Leu Arg
65                  70                  75                  80

Ser Leu Thr Ser Glu Asp Ser Ala Val Tyr Tyr Cys Ser Arg Trp Gly
                85                  90                  95

Ser Tyr Phe Asp Tyr Trp Gly Gln Gly Thr Thr Leu Thr Val Ser Ser
            100                 105                 110

<210> SEQ ID NO 14
<211> LENGTH: 433
<212> TYPE: DNA
<213> ORGANISM: Mus musculus
<220> FEATURE:
<221> NAME/KEY: misc_feature
<222> LOCATION: (423)..(423)
<223> OTHER INFORMATION: n is a, c, g, or t

<400> SEQUENCE: 14
tgcagcagtc aggacctgag ctggtgaaac ctggggcctc agtgaagata tcctgcaagg    60
cttctggata cacattcact gactacaaca tgcactgggt gaagcagagc catggaagag   120
gccttgagtg gattggatat attttttcctt acaatggtga tactgactac aaccagaaat   180
tcaagaacaa ggccacattg actgtagaca attcctccag cacagcctac atggacctcc   240
gcagcctgac atctgaggac tctgcagtct attactgttc aagatggggg tcttactttg   300
actactgggg ccaaggcacc actctcacag tctcctcagc caaaacgaca ccccatctg    360 tctatccact ggcccctgga tctgctgccc aaactaactc catggtgacc ctgggatgcc   420
tgngtcaagg gct                                                     433
```

<210> SEQ ID NO 15
<211> LENGTH: 111
<212> TYPE: PRT
<213> ORGANISM: Mus musculus

<400> SEQUENCE: 15

Val Glu Ser Gly Gly Gly Leu Val Lys Pro Gly Gly Ser Leu Lys Leu
1               5                   10                  15

Ser Cys Ala Ala Ser Gly Phe Thr Phe Ser Ser Tyr Ala Met Ser Trp
                20                  25                  30

Val Arg Gln Thr Pro Lys Lys Ser Leu Glu Trp Val Ala Ser Ile Thr
            35                  40                  45

Ser Gly Gly Ser Ala Tyr Tyr Pro Asp Ser Val Lys Gly Arg Phe Thr
        50                  55                  60

Ile Ser Arg Asp Asn Ala Arg Asn Ile Leu Asn Leu Gln Met Ser Ser
65                  70                  75                  80

Leu Arg Ser Glu Asp Thr Ala Met Tyr Tyr Cys Ala Arg Asp Asp Gly
                85                  90                  95

Tyr Phe Asp Tyr Trp Gly Gln Gly Thr Thr Leu Thr Val Ser Ser
            100                 105                 110

<210> SEQ ID NO 16
<211> LENGTH: 422
<212> TYPE: DNA
<213> ORGANISM: Mus musculus

<400> SEQUENCE: 16
gtggagtctg ggggaggctt agtgaagcct ggagggtccc tgaaactctc ctgtgcagcc      60
tctggattca ctttcagtag ctatgccatg tcttgggttc gccagactcc aaaaaagagt     120
ctggagtggg tcgcatccat tactagtggt ggtagcgcct actatccaga cagtgtgaag     180
ggccgattca ccatctccag agataatgcc aggaacatcc tgaacctgca gatgagcagt     240
ctgaggtctg aggacacggc catgtattac tgtgcaagag acgacgggta ctttgactac     300
tggggccaag gcaccactct cacagtctcc tcagccaaaa cgacaccccc atctgtctat     360
ccactggccc ctggatctgc tgcccaaact aactccatgg tgaccctggg atgcctggtc     420
aa                                                                   422

<210> SEQ ID NO 17
<211> LENGTH: 119
<212> TYPE: PRT
<213> ORGANISM: Mus musculus

<400> SEQUENCE: 17

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Glu Trp Met
            35                  40                  45

Gly Trp Ile Asn Thr Tyr Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Leu Ile Asn Asn Leu Lys Asn Glu Asp Thr Ala Thr Tyr Phe Cys
                85                  90                  95

Ala Arg Arg Asp Gly Tyr Phe Asp Ala Met Asp Tyr Trp Gly Gln Gly
            100                 105                 110

Thr Ser Val Thr Val Ser Ser
        115

<210> SEQ ID NO 18
<211> LENGTH: 482
<212> TYPE: DNA
<213> ORGANISM: Mus musculus
<220> FEATURE:
<221> NAME/KEY: misc_feature
<222> LOCATION: (1)..(2)
<223> OTHER INFORMATION: n is a, c, g, or t

<400> SEQUENCE: 18
nncctgatgg cagctgccca aagtgcccaa gcacagatcc agttggtgca gtctggacct      60
gagctgaaga agcctggaga cagtcaag atctcctgca aggcttctgg gtataccttc      120
acaaactatg gaatgaactg ggtgaagcag gctccaggaa agggtttaga gtggatgggc    180
tggataaaca cctacactgg agagccaact tatgctgatg acttcaaggg acgctttgcc    240
ttctctttgg aaacctctgc cagcactgcc tatttgctga tcaacaacct caaaaatgag    300
gacacggcta catatttctg tgcaagaagg gatggttact tcgatgctat ggactactgg    360
ggtcaaggaa cctcagtcac cgtctcctca gccaaaacga cacccccatc tgtctatcca    420
ctggcccctg gatctgctgc ccaaactaac tccatggtga ccctgggatg cctggtcaag    480
gg                                                                    482

<210> SEQ ID NO 19
<211> LENGTH: 119
<212> TYPE: PRT
<213> ORGANISM: Mus musculus

<400> SEQUENCE: 19

Gln Gln Ser Gly Ala Glu Leu Val Arg Pro Gly Thr Ser Val Lys Val
1               5                   10                  15

Ser Cys Lys Thr Ser Gly Tyr Ala Phe Thr Asn Tyr Leu Ile Glu Trp
            20                  25                  30

Val Asn Gln Arg Pro Gly Gln Gly Leu Glu Trp Ile Gly Val Ile Asn
        35                  40                  45

Pro Gly Ser Gly Gly Thr Asn Tyr Asn Glu Lys Phe Lys Ala Lys Ala
    50                  55                  60

Thr Leu Thr Ala Asp Lys Ser Ser Thr Ala Tyr Met Gln Leu Ser
65                  70                  75                  80

Ser Leu Thr Ser Asp Asp Ser Ala Val Tyr Phe Cys Ala Arg Ser Glu
                85                  90                  95

Arg Gly Tyr Tyr Gly Asn Tyr Gly Ala Met Asp Tyr Trp Gly Gln Gly
            100                 105                 110

Thr Ser Val Thr Val Ser Ser
        115

<210> SEQ ID NO 20
<211> LENGTH: 469
<212> TYPE: DNA
<213> ORGANISM: Mus musculus
<220> FEATURE:
<221> NAME/KEY: misc_feature
<222> LOCATION: (1)..(2)
<223> OTHER INFORMATION: n is a, c, g, or t
<220> FEATURE:

```
<221> NAME/KEY: misc_feature
<222> LOCATION: (457)..(457)
<223> OTHER INFORMATION: n is a, c, g, or t

<400> SEQUENCE: 20
nngcagcagt ctggagctga gctggtaagg cctgggactt cagtgaaggt gtcctgcaag      60
acttctggat acgccttcac taattacttg atagagtggg taaatcagag gcctggacag     120
ggccttgagt ggattggggt gattaatcct ggaagtggtg gtactaacta caatgagaag     180
ttcaaggcca aggcaacact gactgcagac aaatcctcca gcactgccta catgcagctc     240
agcagcctga catctgatga ctctgcggtc tatttctgtg caagatcaga gcgaggctac     300
tatggtaact acggagctat ggactactgg ggtcaaggaa cctcagtcac cgtctcctca     360
gccaaaacga cacccccatc tgtctatcca ctggcccctg gatctgctgc ccaaactaac     420
tccatggtga ccctgggatg cctggtcaag ggctatntcc ctgagccag               469

<210> SEQ ID NO 21
<211> LENGTH: 113
<212> TYPE: PRT
<213> ORGANISM: Mus musculus

<400> SEQUENCE: 21

Gln Gln Pro Gly Pro Glu Leu Val Lys Pro Gly Ala Ser Leu Lys Ile
1               5                   10                  15
Ser Cys Lys Ala Ser Gly Tyr Ser Phe Ser Ser Ser Trp Met Asn Trp
                20                  25                  30
Val Lys Gln Arg Pro Gly Gln Gly Leu Glu Trp Ile Gly Arg Ile Tyr
            35                  40                  45
Pro Val Asp Gly Asp Thr Asn Tyr Asn Gly Lys Phe Lys Gly Lys Ala
        50                  55                  60
Thr Leu Thr Thr Asp Lys Ser Ser Ser Thr Ala Tyr Met Gln Leu Ser
65                  70                  75                  80
Ser Leu Thr Ser Val Asp Ser Ala Val Tyr Phe Cys Ala Arg Thr Gly
                85                  90                  95
Pro Tyr Ala Met Asp Tyr Trp Gly Arg Gly Thr Ser Val Thr Val Ser
            100                 105                 110
Ser

<210> SEQ ID NO 22
<211> LENGTH: 434
<212> TYPE: DNA
<213> ORGANISM: Mus musculus
<220> FEATURE:
<221> NAME/KEY: misc_feature
<222> LOCATION: (1)..(2)
<223> OTHER INFORMATION: n is a, c, g, or t

<400> SEQUENCE: 22
nngcagcagc ctggacctga gctggtgaag cctggggcct cactgaagat ttcctgcaaa      60
gcttctggct actcattcag ttcctcttgg atgaactggg tgaagcagag gcctggacag     120
ggtcttgagt ggattggacg gatttatcct gtagatggag atactaacta caatgggaag     180
ttcaagggca aggccacact gactacagac aaatcctcca gcacagccta catgcagctc     240
agcagcctga cctctgtgga ctctgcggtc tatttctgtg caagaactgg ccctatgct      300
atggactact ggggtcgagg aacctcagtc accgtctcct cagccaaaac gacaccccca     360
tctgtctatc cactggcccc tggatctgct gcccaaacta actccatggt gaccctggga     420
```
tgcctggtca aggg    434

<210> SEQ ID NO 23
<211> LENGTH: 114
<212> TYPE: PRT
<213> ORGANISM: Mus musculus

<400> SEQUENCE: 23

Gly Ala Glu Leu Val Arg Pro Gly Ser Ser Val Lys Ile Ser Cys Lys
1               5                   10                  15

Ala Ser Gly Tyr Thr Phe Ser Thr Tyr Trp Met Asn Trp Val Lys Gln
            20                  25                  30

Arg Pro Gly Gln Gly Leu Glu Trp Ile Gly Gln Ile Tyr Pro Gly Asp
        35                  40                  45

Gly Asp Thr Asn Tyr Asn Gly Lys Phe Lys Gly Lys Ala Thr Leu Thr
    50                  55                  60

Ala Asp Lys Ser Ser Ser Thr Ala Tyr Met Gln Leu Ser Ser Leu Thr
65                  70                  75                  80

Ser Asp Asp Ser Ala Val Tyr Phe Cys Ala Arg Ser Met Val Thr Asn
                85                  90                  95

Tyr Tyr Phe Ala Met Asp Tyr Trp Gly Gln Gly Thr Ser Val Thr Val
            100                 105                 110

Ser Ser

<210> SEQ ID NO 24
<211> LENGTH: 434
<212> TYPE: DNA
<213> ORGANISM: Mus musculus
<220> FEATURE:
<221> NAME/KEY: misc_feature
<222> LOCATION: (425)..(425)
<223> OTHER INFORMATION: n is a, c, g, or t

<400> SEQUENCE: 24
ggggctgagc tggtgaggcc tgggtcctca gtgaagattt cctgcaaggc ttctggctat    60
acattcagta cctactggat gaactgggtg aagcagagac ctggacaggg tcttgagtgg   120
attggacaga tttatcctgg agatggtgat actaactaca tggaaaaatt caagggtaaa   180
gccacactga ctgcagacaa atcctccagc acagcctaca tgcagctcag cagcctaaca   240
tctgacgact ctgcggtcta tttctgtgca agatcgatgg taacgaacta ttactttgct   300
atggactact ggggtcaagg aacctcagtc accgtctcct cagccaaaac gacaccccca   360
tctgtctatc cactggcccc tggatctgct gcccaaacta actccatggt gaccctggga   420
tgccnggtca aggg    434

<210> SEQ ID NO 25
<211> LENGTH: 108
<212> TYPE: PRT
<213> ORGANISM: Mus musculus

<400> SEQUENCE: 25

Gly Gly Leu Val Lys Pro Gly Gly Ser Leu Lys Leu Ser Cys Ala Ala
1               5                   10                  15

Ser Gly Phe Thr Phe Ser Asp Tyr Tyr Met Tyr Trp Val Arg Gln Thr
            20                  25                  30

Pro Glu Lys Lys Leu Glu Trp Val Ala Thr Ile Ser Asp Gly Gly Ser
        35                  40                  45

Tyr Thr Tyr Tyr Pro Asp Ser Val Lys Gly Arg Phe Thr Ile Ser Arg

```
                50                   55                    60
Asp Asn Ala Lys Asn Asn Leu Tyr Leu Gln Met Ser Ser Leu Lys Ser
 65                  70                   75                   80

Glu Asp Thr Ala Met Tyr Tyr Cys Val Arg Gly Leu Leu Gly Phe Asp
                 85                   90                   95

Tyr Trp Gly Gln Gly Thr Thr Leu Thr Val Ser Ser
                100                 105

<210> SEQ ID NO 26
<211> LENGTH: 417
<212> TYPE: DNA
<213> ORGANISM: Mus musculus

<400> SEQUENCE: 26
ggggaggctt agtgaagcct ggagggtccc tgaaactctc ctgtgcagcc tctggattca      60
ctttcagtga ctattacatg tattgggttc gccagactcc ggaaaagaaa ctggagtggg     120
tcgcaaccat tagtgatggt ggtagttaca cctactatcc agacagtgtg aagggccgat     180
tcaccatctc cagagacaat gccaagaaca acctgtacct gcaaatgagc agtctgaagt     240
ctgaggacac agccatgtat tactgtgtaa gggggctact gggttttgac tactggggcc     300
aaggcaccac tctcacagtc tcctcagcca aaacgacacc cccatctgtc tatccactgg     360
cccctggatc tgctgcccaa actaactcca tggtgaccct gggatgcctg gtcaagg        417

<210> SEQ ID NO 27
<211> LENGTH: 113
<212> TYPE: PRT
<213> ORGANISM: Mus musculus
<220> FEATURE:
<221> NAME/KEY: misc_feature
<222> LOCATION: (48)..(48)
<223> OTHER INFORMATION: Xaa can be any naturally occurring amino acid

<400> SEQUENCE: 27

Gly Phe Val Lys Pro Gly Gly Ser Leu Lys Leu Ser Cys Ala Ala Ser
 1               5                  10                  15

Gly Phe Thr Phe Ser Ser Tyr Ala Met Ser Trp Val Arg Gln Thr Pro
                20                  25                  30

Glu Met Arg Leu Glu Trp Val Ala Ser Ile Ser Ser Gly Gly Ser Xaa
             35                  40                  45

Thr Tyr Tyr Pro Asp Ser Val Met Gly Arg Phe Thr Ile Ser Arg Asp
         50                  55                  60

Asn Ala Arg Asn Ile Leu Asn Leu Gln Met Ser Ser Leu Arg Ser Glu
 65                  70                  75                  80

Asp Thr Ala Met Tyr Tyr Cys Ala Arg Val Gly Leu Tyr Tyr Asp Tyr
                 85                  90                  95

Tyr Tyr Ser Met Asp Tyr Trp Gly Gln Gly Thr Ser Val Thr Val Ser
                100                 105                 110

Ser

<210> SEQ ID NO 28
<211> LENGTH: 340
<212> TYPE: DNA
<213> ORGANISM: Mus musculus
<220> FEATURE:
<221> NAME/KEY: misc_feature
<222> LOCATION: (141)..(143)
<223> OTHER INFORMATION: n is a, c, g, or t

<400> SEQUENCE: 28
```

-continued

```
ggcttcgtga agcctggagg gtccctgaaa ctctcctgtg cagcctctgg attcactttc      60
agtagctatg ccatgtcttg ggttcgccag actccagaga tgaggctgga gtgggtcgca     120
tccattagta gtggtggtag nnncacctac tatccagaca gtgtgatggg ccgattcacc     180
atctccagag ataatgccag gaacatcctg aacctgcaaa tgagcagtct gaggtctgag     240
gacacggcca tgtattactg tgcaagagtg ggtctctact atgattatta ctattctatg     300
gactactggg gtcaaggaac ctcagtcacc gtctcctcag                           340
```

<210> SEQ ID NO 29
<211> LENGTH: 114
<212> TYPE: PRT
<213> ORGANISM: Mus musculus

<400> SEQUENCE: 29

Glu Ser Gly Pro Glu Leu Val Lys Pro Gly Ala Ser Val Lys Ile Ser
1               5                   10                  15

Cys Lys Ala Ser Gly Tyr Thr Phe Thr Asp Tyr Asn Met His Trp Val
            20                  25                  30

Arg Gln Ser His Gly Lys Ser Leu Glu Trp Ile Gly Tyr Ile Tyr Pro
        35                  40                  45

Tyr Asn Gly Gly Thr Gly Tyr Asn Gln Lys Phe Lys Ser Lys Ala Thr
    50                  55                  60

Leu Thr Val Asp Asn Ser Ser Thr Ala Tyr Met Glu Leu Arg Ser
65                  70                  75                  80

Leu Thr Ser Glu Asp Ser Ala Val Tyr Tyr Cys Ala Arg Glu Asp Gly
                85                  90                  95

Tyr Tyr Gly Tyr Phe Asp Tyr Trp Gly Gln Gly Thr Thr Leu Thr Gly
            100                 105                 110

Ser Ser

<210> SEQ ID NO 30
<211> LENGTH: 343
<212> TYPE: DNA
<213> ORGANISM: Mus musculus

<400> SEQUENCE: 30

```
gagtcaggac ctgagctggt gaaacctggg gcctcagtga agatatcctg caaggcttct      60
ggatacacat tcactgacta taacatgcac tgggtgaggc agagccatgg aaagagcctt     120
gagtggattg gatatattta tccttacaat ggtggtactg gctacaacca gaagttcaag     180
agtaaggcca cattgactgt agacaattcc tccagcacag cctacatgga gctccgcagc     240
ctgacatctg aggactctgc agtctattac tgtgcaagag aggatggtta ctacggctac     300
tttgactact ggggccaagg caccactctc acaggctcct cag                        343
```

<210> SEQ ID NO 31
<211> LENGTH: 121
<212> TYPE: PRT
<213> ORGANISM: Mus musculus

<400> SEQUENCE: 31

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met

Gly Trp Ile Asn Thr Tyr Thr Gly Glu Pro Thr Tyr Ala Asp Asp Phe
                35                  40                  45
 50                                 55                  60

Lys Gly Arg Phe Ala Phe Ser Leu Glu Thr Ser Ala Ser Ala Ala Tyr
 65                  70                  75                  80

Leu Gln Ile Asn Asn Leu Lys Asn Glu Asp Thr Ala Thr Tyr Phe Cys
                 85                  90                  95

Ala Arg Asp Tyr Asp Gly Tyr Tyr Tyr Ala Met Asp Tyr Trp Gly
                100                 105                 110

Gln Gly Thr Ser Val Thr Val Ser Ser
        115                 120

<210> SEQ ID NO 32
<211> LENGTH: 364
<212> TYPE: DNA
<213> ORGANISM: Mus musculus

<400> SEQUENCE: 32
cagatccagt tggtgcagtc tggacctgag ctgaagaagc ctggagagac agtcaagatc    60
tcctgcaagg cttctgggta taccttcaca aactatggaa tgaactgggt gaagcaggct   120
ccaggaaagg gtttaaagtg gatgggctgg ataaacacct acactggaga gccaacatat   180
gctgatgact caagggacg gtttgccttc tctttggaaa cctctgccag cgctgcctat    240
ttgcagatca acaacctcaa aaatgaggac acggctacat atttctgtgc aagggactat   300
gatggttact attactatgc tatggactac tggggtcaag gaacctcagt caccgtctcc   360
tcag                                                                364

<210> SEQ ID NO 33
<211> LENGTH: 98
<212> TYPE: PRT
<213> ORGANISM: Mus musculus

<400> SEQUENCE: 33

Glu Asn Val Leu Thr Gln Ser Pro Ala Ile Met Ser Ala Ser Leu Gly
 1               5                  10                  15

Glu Lys Val Thr Met Thr Cys Arg Ala Ser Ser Ser Val Asn Tyr Met
                20                  25                  30

Phe Trp Phe Gln Gln Lys Ser Asp Ala Ser Pro Lys Leu Trp Ile Tyr
                35                  40                  45

Tyr Thr Ser Asn Leu Ala Pro Gly Val Pro Ala Arg Phe Ser Gly Ser
 50                  55                  60

Gly Ser Gly Asn Ser Tyr Ser Leu Thr Ile Ser Ser Met Glu Gly Glu
 65                  70                  75                  80

Asp Ala Ala Thr Tyr Tyr Cys Gln Glu Phe Thr Ser Phe Pro Tyr Thr
                 85                  90                  95

Phe Gly

<210> SEQ ID NO 34
<211> LENGTH: 324
<212> TYPE: DNA
<213> ORGANISM: Mus musculus
<220> FEATURE:
<221> NAME/KEY: misc_feature
<222> LOCATION: (1)..(1)
<223> OTHER INFORMATION: n is a, c, g, or t

<400> SEQUENCE: 34

```
ntcagtgtct cagttgtaat gtccagagga gaaaatgtgc tcacccagtc tccagcaatc    60
atgtctgcat ctctagggga gaaggtcacc atgacctgca gggccagctc aagtgtaaat   120
tacatgttct ggttccagca gaagtcagat gcctccccca aattgtggat ttattataca   180
tccaacctgg ctcctggagt cccagctcgc ttcagtggca gtgggtctgg gaactcttat   240
tctctcacaa tcagcagcat ggagggtgaa gatgctgcca cttattactg ccaggagttt   300 actagttttcc cgtacacgtt cgga                                         324
```

<210> SEQ ID NO 35
<211> LENGTH: 99
<212> TYPE: PRT
<213> ORGANISM: Mus musculus

<400> SEQUENCE: 35

```
Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Gln
                85                  90                  95

Tyr Thr Phe
```

<210> SEQ ID NO 36
<211> LENGTH: 331
<212> TYPE: DNA
<213> ORGANISM: Mus musculus

<400> SEQUENCE: 36

```
ttatgctttt ttggatttca gcctccagag gtgatattgt gctaactcag tctccagcca    60
ccctgtctgt gactccagga gatagcgtca gtctttcctg cagggccagc caaagtatta   120
gcaacaacct acactggtat caacaaaaat cacatgagtc tccaaggctt ctcatcaagt   180
atgcttccca gtccatctct gggatcccct ccaggttcag tggcagtgga tcagggacag   240
atttcactct cagtatcaac agtgtggaga ctgaagattt tggaatgtat ttctgtcaac   300
agagtaacag ctggcctcag tacacgttcg g                                  331
```

<210> SEQ ID NO 37
<211> LENGTH: 103
<212> TYPE: PRT
<213> ORGANISM: Mus musculus

<400> SEQUENCE: 37

```
Ser Ile Val Met Thr Gln Thr Pro Lys Phe Leu Leu Val Ser Ala Gly
1               5                   10                  15

Asp Arg Leu Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Thr Ser Asn Arg Tyr Thr Gly Val Pro Asp Arg Phe Thr Gly
    50                  55                  60
```

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Asn Ser Pro Trp
                85                  90                  95

Thr Phe Gly Gly Gly Thr Lys
            100

<210> SEQ ID NO 38
<211> LENGTH: 355
<212> TYPE: DNA
<213> ORGANISM: Mus musculus

<400> SEQUENCE: 38
ccaggtcttc gtatttctac tgctctgtgt gtctggtgct catgggagta ttgtgatgac      60
ccagactccc aaattcctgc ttgtatcagc aggagacagg cttaccataa cctgcaaggc     120
cagtcagagt gtgagtaatg atgtagcttg gtaccaacag aagccagggc agtctcctaa     180
actgctgata tactatacat ccaatcgcta cactggagtc cctgatcgct tcactggcag     240
tggatatggg acggatttca ctttcaccat cagcactgtg caggctgaag acctggcagt     300
ttatttctgt cagcaggatt ataactctcc gtggacgttc ggtggaggca ccaag          355

<210> SEQ ID NO 39
<211> LENGTH: 103
<212> TYPE: PRT
<213> ORGANISM: Mus musculus

<400> SEQUENCE: 39

Ser Ile Val Met Thr Gln Thr Pro Lys Phe Leu Leu Val Ser Ala Gly
1               5                   10                  15

Asp Arg Leu Thr Ile Thr Cys Lys Ala Ser Gln Ser Val Ser Asn Asp
                20                  25                  30

Val Ala Trp Tyr Gln Gln Lys Pro Gly Gln Ser Pro Lys Leu Leu Ile
            35                  40                  45

Tyr Tyr Thr Ser Asn Arg Tyr Thr Gly Val Pro Asp Arg Phe Thr Gly
        50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Asn Ser Pro Trp
                85                  90                  95

Thr Phe Gly Gly Gly Thr Lys
            100

<210> SEQ ID NO 40
<211> LENGTH: 323
<212> TYPE: DNA
<213> ORGANISM: Mus musculus

<400> SEQUENCE: 40
tggtgctcat gggagtattg tgatgaccca gactcccaaa ttcctgcttg tatcagcagg      60
agacaggctt accataacct gcaaggccag tcagagtgtg agtaatgatg tagcttggta     120
ccaacagaag ccagggcagt ctcctaaact gctgatatac tatacatcca atcgctacac     180
tggagtccct gatcgcttca ctggcagtgg atatgggacg gatttcactt tcaccatcag     240
cactgtgcag gctgaagacc tggcagttta tttctgtcag caggattata actctccgtg     300
gacgttcggt ggaggcacca agc                                             323

<210> SEQ ID NO 41
<211> LENGTH: 99
<212> TYPE: PRT
<213> ORGANISM: Mus musculus

<400> SEQUENCE: 41

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Arg Ser His Glu Ser Pro Arg Leu Leu Ile
        35                  40                  45

Lys Tyr Val Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly

<210> SEQ ID NO 42
<211> LENGTH: 336
<212> TYPE: DNA
<213> ORGANISM: Mus musculus

<400> SEQUENCE: 42
cttggacttt tgcttttctg gacttcagcc tccagatgtg acattgtgat gactcagtct     60
ccagccaccc tgtctgtgac tccaggagat agagtctctc tttcctgcag ggccagccag    120
agtattagcg actacttaca ctggtatcaa caaagatcac atgagtctcc aaggcttctc    180
atcaaatatg tttcccaatc catctctggg atcccctcca ggttcagtgg cagtggatca    240
gggtcagatt tcactctcag tatcaacagt gtggaacctg aagatgttgg agtgtattat    300
tgtcaaaatg gtcacagctt tccgtacacg ttcgga                              336

<210> SEQ ID NO 43
<211> LENGTH: 98
<212> TYPE: PRT
<213> ORGANISM: Mus musculus

<400> SEQUENCE: 43

Asp Ile Gln Met Thr Gln Ser Pro Ala Ser Leu Ser Val Ser Val Gly
1               5                   10                  15

Glu Thr Val Thr Ile Thr Cys Arg Thr Ser Glu Asn Ile Phe Ser Asn
            20                  25                  30

Phe Ala Trp Tyr Gln Gln Pro Gly Lys Ser Pro Gln Leu Leu Val
        35                  40                  45

Tyr Gly Ala Thr Asn Leu Ala Asp Gly Val Pro Ser Arg Phe Ser Gly
    50                  55                  60

Ser Gly Ser Gly Thr Gln Tyr Ser Leu Lys Ile Thr Ser Leu Gln Ser
65                  70                  75                  80

Glu Asp Phe Gly Ser Tyr Tyr Cys Gln His Phe Trp Gly Ser Pro Trp
                85                  90                  95

Thr Phe

<210> SEQ ID NO 44
<211> LENGTH: 313

<212> TYPE: DNA
<213> ORGANISM: Mus musculus

<400> SEQUENCE: 44

```
ttacagatgc cagatgtgac atccagatga ctcagtctcc agcctcccta tctgtatctg      60
tgggagaaac tgtcaccatc acatgtcgaa caagtgaaaa tattttcagt aatttcgcat     120
ggtatcagca gcaaccggga aaatctcctc agctcctggt ctatggtgca caaaacttag     180
cagatggtgt gccatcaagg ttcagtggca gtggatcagg cacacagtat ccctcaaga     240
tcaccagcct gcagtctgaa gattttggga gttattactg tcaacatttt tggggtagtc     300
cgtggacgtt cgg                                                         313
```

<210> SEQ ID NO 45
<211> LENGTH: 99
<212> TYPE: PRT
<213> ORGANISM: Mus musculus

<400> SEQUENCE: 45

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Tyr
                85                  90                  95

Thr Phe Gly

<210> SEQ ID NO 46
<211> LENGTH: 326
<212> TYPE: DNA
<213> ORGANISM: Mus musculus

<400> SEQUENCE: 46

```
tcagtgcctc agtcataatg tccaggggac aaattgttct cacccagtct ccagcactca      60
tgtctgcatc tccaggggag aaggtcacca tgacctgcag tgccagctca agtgtaagtt     120
acatgtactg gtaccagcag aagccaagat cctcccccaa accctggatt tatctcacat     180
ccaacctggc ttctggagtc cctgctcgct tcagtggcag tgggtctggg acctcttact     240
ctctcacaat cagcagcatg gaggctgaag atgctgccac ttattactgc agcagtgga     300
gtagtaaccc accctacacg ttcgga                                           326
```

<210> SEQ ID NO 47
<211> LENGTH: 100
<212> TYPE: PRT
<213> ORGANISM: Mus musculus

<400> SEQUENCE: 47

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Ser Asn Ser Trp Pro Ala
                 85                  90                  95

Leu Thr Phe Gly
            100

<210> SEQ ID NO 48
<211> LENGTH: 336
<212> TYPE: DNA
<213> ORGANISM: Mus musculus

<400> SEQUENCE: 48
ggacttttgc ttttctggat tccagcctcc agaggtgaca tcttgctgac tcagtctcca    60
gccatcctgt ctgtgagtcc aggagaaaga gtcagtttct cctgcagggc cagtcagagc   120
attggcacaa gcatacactg gtatcaacaa gaaacaaatg gttctccaag gcttctcata   180
aagtatgctt ctgagtctat ctctgggatc ccttccaggt ttagtggcag tggatcaggg   240
acagatttta ctcttagcat caacagtgtg gagtctgaag atattgcaga ttattactgt   300
caacaaagta atagctggcc agcgctcacg ttcggt                             336

<210> SEQ ID NO 49
<211> LENGTH: 98
<212> TYPE: PRT
<213> ORGANISM: Mus musculus

<400> SEQUENCE: 49

Asp Ile Gln Met Thr Gln Ser Pro Ala Ser Leu Ser Ala Ser Val Gly
  1               5                  10                  15

Asp Thr Val Thr Ile Thr Cys Arg Ala Ser Glu Asn Ile Tyr Ser Tyr
             20                  25                  30

Leu Ala Trp Tyr Gln Gln Lys Gln Gly Lys Ser Pro Gln Leu Leu Val
         35                  40                  45

Tyr Asn Ala Lys Thr Phe Ala Glu Gly Val Arg Ser Arg Phe Ser Gly
 50                  55                  60

Ser Gly Ser Gly Thr Gln Phe Ser Leu Gln Ile Thr Ser Leu Gln Pro
 65                  70                  75                  80

Glu Asp Phe Gly Ser Tyr Tyr Cys Gln His His Tyr Gly Ser Pro Tyr
                 85                  90                  95

Thr Phe

<210> SEQ ID NO 50
<211> LENGTH: 327
<212> TYPE: DNA
<213> ORGANISM: Mus musculus

<400> SEQUENCE: 50
tctgctgctg tggcttacag gtgccagatg tgacatccag atgactcagt ctccagcctc    60
cctatctgca tctgtgggag atactgtcac catcacatgt cgagcaagtg agaatattta   120
cagttattta gcatggtatc agcagaaaca gggaaaatct cctcagctcc tggtctataa   180
tgcaaaaacc ttcgcagaag gtgtgcgatc aaggttcagt ggcagtggat caggcacaca   240

```
gttttctctg cagatcacca gcctgcagcc tgaagatttt gggagttatt actgtcaaca    300
tcattatggt tctccgtaca cgttcgg                                        327
```

<210> SEQ ID NO 51
<211> LENGTH: 105
<212> TYPE: PRT
<213> ORGANISM: Mus musculus
<400> SEQUENCE: 51

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly
            100                 105
```

<210> SEQ ID NO 52
<211> LENGTH: 327
<212> TYPE: DNA
<213> ORGANISM: Mus musculus
<400> SEQUENCE: 52

```
ggtacctgtg gggacattgt gatgacgcag tctccatcct ccctgactgt gacagcagga    60
gagaaggtca ctatgagctg caagtccagt cagagtctgt taaacagtgg aaatcaaaaa    120
aactacttga cctggtacca gcagaaacca gggcagcctc ctaaactgtt gatctcctgg    180
gcatccacta gggaatctgg ggtccctgat cgcttcacag gcagtggatc tggaacagat    240
ttcactctca ccatcagcag tgtgcaggct gaagacctgg cagtttatta ctgtcagaat    300
gactatagtt atccattcac gttcggc                                        327
```

<210> SEQ ID NO 53
<211> LENGTH: 98
<212> TYPE: PRT
<213> ORGANISM: Mus musculus
<220> FEATURE:
<221> NAME/KEY: misc_feature
<222> LOCATION: (63)..(63)
<223> OTHER INFORMATION: Xaa can be any naturally occurring amino acid
<400> SEQUENCE: 53

```
Asp Ile Ala Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Ala Asp Arg Phe Xaa Gly
    50                  55                  60

Ser Arg Cys Gly Thr Asp Phe Thr Phe Pro Ile Ser Ser Val Gln Gly
65                  70                  75                  80
```

Glu Asp Leu Ala Val Tyr Tyr Cys Gln Gln His Tyr Ser Ile His Ser
                85                  90                  95

Arg Ser

<210> SEQ ID NO 54
<211> LENGTH: 331
<212> TYPE: DNA
<213> ORGANISM: Mus musculus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t

<400> SEQUENCE: 54
nctgctattc tgctatgggt atctggtgtt gacggagaca ttgcgatgac ccagtctcac    60
aaattcatgt ccacatcagt aggagacagg gtcagcatca cctgcaaggc cagtcaggat   120
gtgagtactg ctgtagcctg gtatcaacag aaaccaggac aatctcctaa actactgatt   180
tactcggcat cctaccggta cactggagtc cgtgatcgct tcantggcag tcgatgtggg   240
acggatttca ctttcccat cagcagtgtg cagggtgaag acctggcagt ttattactgt   300
cagcaacatt atagtatcca ttcacgttcg g                                   331

<210> SEQ ID NO 55
<211> LENGTH: 107
<212> TYPE: PRT
<213> ORGANISM: Mus musculus

<400> SEQUENCE: 55

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr
            100                 105

<210> SEQ ID NO 56
<211> LENGTH: 344
<212> TYPE: DNA
<213> ORGANISM: Mus musculus

<400> SEQUENCE: 56
tggatccctg cttccagcag tgatgttttg atgacccaaa ctccactctc cctgcctgtc    60
agtcttggag atcaagcctc catctcttgc agatctagtc agagcattgt acatagtaat   120
ggaaacacct atttagaatg gtacctgcag aaaccaggcc agtctccaaa gctcctgatc   180
tacagagttt ccaaccgatt ttctggggtc ccagacaggt tcagtggcag tggatcaggg   240

```
acagatttca cactcaagat cagcagagtg gaggctgagg atctgggagt ttattactgc    300
tttcaaggtt cacatgttcc gtggacgttc ggtggaggca ccaa                    344
```

<210> SEQ ID NO 57
<211> LENGTH: 113
<212> TYPE: PRT
<213> ORGANISM: Mus musculus

<400> SEQUENCE: 57

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Tyr Ser
            20                  25                  30

Gly Asn Gln Lys Asn Tyr Leu Thr Trp Tyr Gln Gln Lys Pro Gly Gln
        35                  40                  45

Pro Pro Lys Met Leu Ile Tyr Trp Ala Ser Thr Arg Glu Ser Gly Val
    50                  55                  60

Pro Asp Arg Phe Thr Gly Ser Gly Ser Gly Thr His Phe Thr Leu Thr
65                  70                  75                  80

Ile Ser Ser Val Gln Ala Glu Asp Leu Ala Ile Tyr Tyr Cys Gln Asn
                85                  90                  95

Asp Tyr Ser Tyr Pro Val Thr Phe Gly Ala Gly Thr Lys Leu Glu Leu
            100                 105                 110

Lys
```

<210> SEQ ID NO 58
<211> LENGTH: 340
<212> TYPE: DNA
<213> ORGANISM: Mus musculus

<400> SEQUENCE: 58

```
gacattgtga tgacacagtc tccatcctcc ctgactgtga cagcaggaga gaaggtcact     60
atgagctgca agtccagtca gagtctgtta tacagtggaa atcaaaagaa ctacttgacc    120
tggtaccagc agaaaccagg gcagcctcct aaaatgttga tctactgggc atccactagg    180
gaatctgggg tccctgatcg cttcacaggc agtggatctg gaacacattt cactctcacc    240
atcagcagtg tgcaggctga agacctggca atttattact gtcagaatga ttatagttat    300
ccggtcacgt tcggtgctgg gaccaagctg gagctgaaac                          340
```

<210> SEQ ID NO 59
<211> LENGTH: 106
<212> TYPE: PRT
<213> ORGANISM: Mus musculus

<400> SEQUENCE: 59

```
Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Ser Val Asn Tyr Met
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Tyr Pro Leu Ile Thr
```

-continued

```
                  85                  90                  95

Phe Gly Ala Gly Thr Lys Leu Glu Leu Lys
            100                 105

<210> SEQ ID NO 60
<211> LENGTH: 319
<212> TYPE: DNA
<213> ORGANISM: Mus musculus

<400> SEQUENCE: 60
gaaattgtgc tcactcagtc tccagccatc acagctgcat ctctgggggca aaaggtcacc      60 atcacctgca gtgccagctc aagtgtaaat tacatgcact ggtaccagca gaagtcaggc    120
acctccccca aaccatggat ttatgaaata tccaaactgg cttctggagt cccagctcgc    180
ttcagtggca gtgggtctgg gacctcttac tctctcacaa tcagcagcat ggaggctgaa    240
gatgctgcca tttattactg ccagcagtgg aattatcctc ttatcacgtt cggtgctggg    300
accaagctgg agctgaaac                                                 319

<210> SEQ ID NO 61
<211> LENGTH: 107
<212> TYPE: PRT
<213> ORGANISM: Mus musculus

<400> SEQUENCE: 61

Glu Asn Ala Leu Thr Gln Ser Pro Ala Ile Met Ser Ala Ser Pro Gly
1               5                  10                  15

Glu Lys Val Thr Met Thr Cys Ser Ala Ser Ser Ser Val Ser Tyr Met
            20                  25                  30

His Trp Tyr Gln Gln Lys Ser Ser Met Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Glu Val Ala Thr Tyr Tyr Cys Phe Gln Gly Ser Gly Phe Pro Val His
                85                  90                  95

Val Arg Arg Gly Asp Gln Val Gly Asn Lys Thr
            100                 105

<210> SEQ ID NO 62
<211> LENGTH: 321
<212> TYPE: DNA
<213> ORGANISM: Mus musculus

<400> SEQUENCE: 62
gaaaatgctc tcacccagtc tccagcaatc atgtctgcat ctccagggga aaaggtcacc      60
atgacctgca gtgccagctc aagtgtaagt tacatgcact ggtaccagca gaagtcaagc    120
atgtccccca aactctggat ttatgacaca tccaaactgg cttctggagt cccaggtcgc    180
ttcagtggca gtgggtctgg aaactcttac tctctcacga tcagcagcat ggaggctgaa    240
gaggttgcca cttattactg ttttcagggg tagtgggttc ccagtacacg ttcggagggg    300
ggaccaagtt ggaaataaaa c                                              321

<210> SEQ ID NO 63
<211> LENGTH: 107
<212> TYPE: PRT
<213> ORGANISM: Mus musculus
```

<400> SEQUENCE: 63

Asp Ile Gln Met Thr Gln Ser Pro Ala Ser Leu Ser Ala Ser Val Gly
1               5                   10                  15

Glu Thr Ile Thr Ile Thr Cys Arg Ala Ser Gly Asn Ile His Asn Tyr
            20                  25                  30

Leu Ala Trp Tyr Gln Gln Lys Gln Gly Lys Ser Pro His Leu Leu Val
        35                  40                  45

Phe His Ala Arg Ser Leu Ala Asp Gly Val Pro Ser Arg Phe Ser Gly
    50                  55                  60

Ser Gly Ser Gly Thr Gln Tyr Ser Leu Asn Ile Asn Ser Leu Gln Pro
65                  70                  75                  80

Glu Asp Phe Gly Ile Tyr Tyr Cys Gln His Phe Trp Tyr Thr Pro Tyr
                85                  90                  95

Thr Phe Gly Gly Gly Thr Lys Leu Glu Ile Lys
            100                 105

<210> SEQ ID NO 64
<211> LENGTH: 322
<212> TYPE: DNA
<213> ORGANISM: Mus musculus

<400> SEQUENCE: 64
gacatccaga tgactcagtc tccagcctcc ctatctgcat ctgtgggaga aactatcacc    60
atcacatgtc gagcaagtgg gaatattcac aattatttag catggtatca gcagaaacag   120
ggaaaatctc ctcacctcct ggtctttcat gcaagatcct tagcagatgg tgtgccatca   180
aggttcagtg gcagtggatc aggaacacaa tattctctca atatcaacag cctgcagcct   240
gaagattttg ggatttatta ctgtcaacat ttttggtata ctccgtacac gttcggaggg   300
gggaccaagc tggaaataaa ac                                            322

<210> SEQ ID NO 65
<211> LENGTH: 8
<212> TYPE: PRT
<213> ORGANISM: Artificial
<220> FEATURE:
<223> OTHER INFORMATION: Amd1.6Vh, CDR1

<400> SEQUENCE: 65

Gly Tyr Ser Phe Thr Asn Tyr Trp
1               5

<210> SEQ ID NO 66
<211> LENGTH: 8
<212> TYPE: PRT
<213> ORGANISM: Artificial
<220> FEATURE:
<223> OTHER INFORMATION: Amd1.6Vh, CDR2

<400> SEQUENCE: 66

Ile Tyr Pro Gly Asn Ser Asp Thr
1               5

<210> SEQ ID NO 67
<211> LENGTH: 8
<212> TYPE: PRT
<213> ORGANISM: Artificial
<220> FEATURE:
<223> OTHER INFORMATION: Amd1.6Vh, CDR3

<400> SEQUENCE: 67

```
Asp Asp Tyr Ser Arg Phe Ser Tyr
1               5

<210> SEQ ID NO 68
<211> LENGTH: 6
<212> TYPE: PRT
<213> ORGANISM: Artificial
<220> FEATURE:
<223> OTHER INFORMATION: Amd1.6Vl, CDR1

<400> SEQUENCE: 68

Gln Ser Val Ser Asn Asp
1               5

<210> SEQ ID NO 69
<211> LENGTH: 3
<212> TYPE: PRT
<213> ORGANISM: Artificial
<220> FEATURE:
<223> OTHER INFORMATION: Amd1.6Vl, CDR2

<400> SEQUENCE: 69

Tyr Thr Ser
1

<210> SEQ ID NO 70
<211> LENGTH: 8
<212> TYPE: PRT
<213> ORGANISM: Artificial
<220> FEATURE:
<223> OTHER INFORMATION: Amd2.1Vh, CDR1

<400> SEQUENCE: 70

Gly Phe Thr Phe Ser Ser Tyr Ala
1               5

<210> SEQ ID NO 71
<211> LENGTH: 8
<212> TYPE: PRT
<213> ORGANISM: Artificial
<220> FEATURE:
<223> OTHER INFORMATION: Amd2.1Vh, CDR2
<220> FEATURE:
<221> NAME/KEY: misc_feature
<222> LOCATION: (7)..(7)
<223> OTHER INFORMATION: Xaa can be any naturally occurring amino acid

<400> SEQUENCE: 71

Ile Ser Ser Gly Gly Ser Xaa Thr
1               5

<210> SEQ ID NO 72
<211> LENGTH: 13
<212> TYPE: PRT
<213> ORGANISM: Artificial
<220> FEATURE:
<223> OTHER INFORMATION: Amd2.1Vh, CDR3

<400> SEQUENCE: 72

Val Gly Leu Tyr Tyr Asp Tyr Tyr Tyr Ser Met Asp Tyr
1               5                   10

<210> SEQ ID NO 73
<211> LENGTH: 12
<212> TYPE: PRT
<213> ORGANISM: Artificial
<220> FEATURE:
```

<223> OTHER INFORMATION: Amd2.1V1, CDR1

<400> SEQUENCE: 73

Gln Ser Leu Leu Tyr Ser Gly Asn Gln Lys Asn Tyr
1               5                   10

<210> SEQ ID NO 74
<211> LENGTH: 3
<212> TYPE: PRT
<213> ORGANISM: Artificial
<220> FEATURE:
<223> OTHER INFORMATION: Amd2.1V1, CDR2

<400> SEQUENCE: 74

Trp Ala Ser
1

<210> SEQ ID NO 75
<211> LENGTH: 1257
<212> TYPE: PRT
<213> ORGANISM: staphylococcus aureus

<400> SEQUENCE: 75

Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu Thr
            20                  25                  30

Thr Gln Asp Gln Thr Thr Asn Lys Asn Val Leu Asp Ser Asn Lys Val
        35                  40                  45

Lys Ala Thr Thr Glu Gln Ala Lys Ala Glu Val Lys Asn Pro Thr Gln
50                  55                  60

Asn Ile Ser Gly Thr Gln Val Tyr Gln Asp Pro Ala Ile Val Gln Pro
65                  70                  75                  80

Lys Ala Ala Asn Lys Thr Gly Asn Ala Gln Val Asn Gln Lys Val Asp
                85                  90                  95

Thr Thr Gln Val Asn Gly Asp Thr Arg Ala Thr Gln Ser Thr Thr Ser
            100                 105                 110

Asn Asn Ala Lys Pro Val Thr Lys Ser Thr Asn Thr Thr Ala Pro Lys
        115                 120                 125

Thr Asn Asn Asn Val Thr Ser Ala Gly Tyr Ser Leu Val Asp Asp Glu
130                 135                 140

Asp Asp Asn Ser Glu Asn Gln Ile Asn Pro Glu Leu Ile Lys Ser Ala
145                 150                 155                 160

Ala Lys Pro Ala Ala Leu Glu Thr Gln Tyr Lys Ala Ala Pro Lys
                165                 170                 175

Ala Thr Pro Val Ala Pro Lys Ala Lys Thr Glu Ala Thr Pro Lys Val
            180                 185                 190

Thr Thr Phe Ser Ala Ser Ala Gln Pro Arg Ser Ala Ala Ala Pro
        195                 200                 205

Lys Thr Ser Leu Pro Lys Tyr Lys Pro Gln Val Asn Ser Ser Ile Asn
210                 215                 220

Asp Tyr Ile Arg Lys Asn Asn Leu Lys Ala Pro Lys Ile Glu Glu Asp
225                 230                 235                 240

Tyr Thr Ser Tyr Phe Pro Lys Tyr Ala Tyr Arg Asn Gly Val Gly Arg
                245                 250                 255

Pro Glu Gly Ile Val Val His Asp Thr Ala Asn Asp Arg Ser Thr Ile
            260                 265                 270

```
Asn Gly Glu Ile Ser Tyr Met Lys Asn Asn Tyr Gln Asn Ala Phe Val
            275                 280                 285
His Ala Phe Val Asp Gly Asp Arg Ile Ile Glu Thr Ala Pro Thr Asp
        290                 295                 300
Tyr Leu Ser Trp Gly Val Gly Ala Val Gly Asn Pro Arg Phe Ile Asn
305                 310                 315                 320
Val Glu Ile Val His Thr His Asp Tyr Ala Ser Phe Ala Arg Ser Met
                325                 330                 335
Asn Asn Tyr Ala Asp Tyr Ala Ala Thr Gln Leu Gln Tyr Tyr Gly Leu
            340                 345                 350
Lys Pro Asp Ser Ala Glu Tyr Asp Gly Asn Gly Thr Val Trp Thr His
        355                 360                 365
Tyr Ala Val Ser Lys Tyr Leu Gly Gly Thr Asp His Ala Asp Pro His
        370                 375                 380
Gly Tyr Leu Arg Ser His Asn Tyr Ser Tyr Asp Gln Leu Tyr Asp Leu
385                 390                 395                 400
Ile Asn Glu Lys Tyr Leu Ile Lys Met Gly Lys Val Ala Pro Trp Gly
            405                 410                 415
Thr Gln Ser Thr Thr Thr Pro Thr Thr Pro Ser Lys Pro Ser Thr Pro
        420                 425                 430
Ser Lys Pro Ser Thr Pro Ser Thr Gly Lys Leu Thr Val Ala Ala Asn
        435                 440                 445
Asn Gly Val Ala Gln Ile Lys Pro Thr Asn Ser Gly Leu Tyr Thr Thr
        450                 455                 460
Val Tyr Asp Lys Thr Gly Lys Ala Thr Asn Glu Val Gln Lys Thr Phe
465                 470                 475                 480
Ala Val Ser Lys Thr Ala Thr Leu Gly Asn Gln Lys Phe Tyr Leu Val
                485                 490                 495
Gln Asp Tyr Asn Ser Gly Asn Lys Phe Gly Trp Val Lys Glu Gly Asp
            500                 505                 510
Val Val Tyr Asn Thr Ala Lys Ser Pro Val Asn Val Asn Gln Ser Tyr
            515                 520                 525
Ser Ile Lys Pro Gly Thr Lys Leu Tyr Thr Val Pro Trp Gly Thr Ser
        530                 535                 540
Lys Gln Val Ala Gly Ser Val Ser Gly Ser Gly Asn Gln Thr Phe Lys
545                 550                 555                 560
Ala Ser Lys Gln Gln Gln Ile Asp Lys Ser Ile Tyr Leu Tyr Gly Ser
                565                 570                 575
Val Asn Gly Lys Ser Gly Trp Val Ser Lys Ala Tyr Leu Val Asp Thr
            580                 585                 590
Ala Lys Pro Thr Pro Thr Pro Thr Pro Lys Pro Ser Thr Pro Thr Thr
        595                 600                 605
Asn Asn Lys Leu Thr Val Ser Ser Leu Asn Gly Val Ala Gln Ile Asn
        610                 615                 620
Ala Lys Asn Asn Gly Leu Phe Thr Thr Val Tyr Asp Lys Thr Gly Lys
625                 630                 635                 640
Pro Thr Lys Glu Val Gln Lys Thr Phe Ala Val Thr Lys Glu Ala Ser
                645                 650                 655
Leu Gly Gly Asn Lys Phe Tyr Leu Val Lys Asp Tyr Asn Ser Pro Thr
            660                 665                 670
Leu Ile Gly Trp Val Lys Gln Gly Asp Val Ile Tyr Asn Asn Ala Lys
        675                 680                 685
Ser Pro Val Asn Val Met Gln Thr Tyr Thr Val Lys Pro Gly Thr Lys
```

```
                690              695              700
Leu Tyr Ser Val Pro Trp Gly Thr Tyr Lys Gln Glu Ala Gly Ala Val
705                      710                  715                  720

Ser Gly Thr Gly Asn Gln Thr Phe Lys Ala Thr Lys Gln Gln Ile
                    725                  730                  735

Asp Lys Ser Ile Tyr Leu Tyr Gly Thr Val Asn Gly Lys Ser Gly Trp
                740                  745                  750

Ile Ser Lys Ala Tyr Leu Ala Val Pro Ala Ala Pro Lys Lys Ala Val
            755                  760                  765

Ala Gln Pro Lys Thr Ala Val Lys Ala Tyr Ala Val Thr Lys Pro Gln
770                  775                  780

Thr Thr Gln Thr Val Ser Lys Ile Ala Gln Val Lys Pro Asn Asn Thr
785                  790                  795                  800

Gly Ile Arg Ala Ser Val Tyr Glu Lys Thr Ala Lys Asn Gly Ala Lys
                805                  810                  815

Tyr Ala Asp Arg Thr Phe Tyr Val Thr Lys Glu Arg Ala His Gly Asn
                820                  825                  830

Glu Thr Tyr Val Leu Leu Asn Asn Thr Ser His Asn Ile Pro Leu Gly
                835                  840                  845

Trp Phe Asn Val Lys Asp Leu Asn Val Gln Asn Leu Gly Lys Glu Val
        850                  855                  860

Lys Thr Thr Gln Lys Tyr Thr Val Asn Arg Ser Asn Gly Leu Ser
865                  870                  875                  880

Met Val Pro Trp Gly Thr Lys Asn Gln Val Ile Leu Thr Gly Asn Asn
                    885                  890                  895

Ile Ala Gln Gly Thr Phe Asn Ala Thr Lys Gln Val Ser Val Gly Lys
                900                  905                  910

Asp Val Tyr Leu Tyr Gly Thr Ile Asn Asn Arg Thr Gly Trp Val Asn
                915                  920                  925

Ser Lys Asp Leu Thr Ala Pro Thr Ala Val Lys Pro Thr Thr Ser Ala
930                  935                  940

Ala Lys Asp Tyr Asn Tyr Thr Tyr Val Ile Lys Asn Gly Asn Gly Tyr
945                  950                  955                  960

Tyr Tyr Val Thr Pro Asn Ser Asp Thr Ala Lys Tyr Ser Leu Lys Ala
                    965                  970                  975

Phe Asn Glu Gln Pro Phe Ala Val Val Lys Glu Gln Val Ile Asn Gly
                980                  985                  990

Gln Thr Trp Tyr Tyr Gly Lys Leu  Ser Asn Gly Lys Leu  Ala Trp Ile
                995                 1000                 1005

Lys Ser  Thr Asp Leu Ala Lys  Glu Leu Ile Lys Tyr  Asn Gln Ile
    1010                 1015                 1020

Gly Met  Thr Leu Asn Gln Val  Ala Gln Ile Gln Ala  Gly Leu Gln
    1025                 1030                 1035

Tyr Lys  Pro Gln Val Gln Arg  Val Pro Gly Lys Trp  Thr Asp Ala
    1040                 1045                 1050

Asn Phe  Asn Asp Val Lys His  Ala Met Asp Thr Lys  Arg Leu Ala
    1055                 1060                 1065

Gln Asp  Pro Ala Leu Lys Tyr  Gln Phe Leu Arg Leu  Asp Gln Pro
    1070                 1075                 1080

Gln Asn  Ile Ser Ile Asp Lys  Ile Asn Gln Phe Leu  Lys Gly Lys
    1085                 1090                 1095

Gly Val  Leu Glu Asn Gln Gly  Ala Ala Phe Asn Lys  Ala Ala Gln
    1100                 1105                 1110
```

-continued

```
Met Tyr Gly Ile Asn Glu Val Tyr Leu Ile Ser His Ala Leu Leu
    1115                1120                1125

Glu Thr Gly Asn Gly Thr Ser Gln Leu Ala Lys Gly Ala Asp Val
    1130                1135                1140

Val Asn Asn Lys Val Val Thr Asn Ser Asn Thr Lys Tyr His Asn
    1145                1150                1155

Val Phe Gly Ile Ala Ala Tyr Asp Asn Asp Pro Leu Arg Glu Gly
    1160                1165                1170

Ile Lys Tyr Ala Lys Gln Ala Gly Trp Asp Thr Val Ser Lys Ala
    1175                1180                1185

Ile Val Gly Gly Ala Lys Phe Ile Gly Asn Ser Tyr Val Lys Ala
    1190                1195                1200

Gly Gln Asn Thr Leu Tyr Lys Met Arg Trp Asn Pro Ala His Pro
    1205                1210                1215

Gly Thr His Gln Tyr Ala Thr Asp Val Asp Trp Ala Asn Ile Asn
    1220                1225                1230

Ala Lys Ile Ile Lys Gly Tyr Tyr Asp Lys Ile Gly Glu Val Gly
    1235                1240                1245

Lys Tyr Phe Asp Ile Pro Gln Tyr Lys
    1250                1255

<210> SEQ ID NO 76
<211> LENGTH: 580
<212> TYPE: PRT
<213> ORGANISM: staphylococcus aureus

<400> SEQUENCE: 76

Ser Ala Gln Pro Arg Ser Ala Ala Ala Pro Lys Thr Ser Leu Pro
1               5                   10                  15

Lys Tyr Lys Pro Gln Val Asn Ser Ser Ile Asn Asp Tyr Ile Arg Lys
            20                  25                  30

Asn Asn Leu Lys Ala Pro Lys Ile Glu Glu Asp Tyr Thr Ser Tyr Phe
            35                  40                  45

Pro Lys Tyr Ala Tyr Arg Asn Gly Val Gly Arg Pro Glu Gly Ile Val
        50                  55                  60

Val His Asp Thr Ala Asn Asp Arg Ser Thr Ile Asn Gly Glu Ile Ser
65                  70                  75                  80

Tyr Met Lys Asn Asn Tyr Gln Asn Ala Phe Val His Ala Phe Val Asp
                85                  90                  95

Gly Asp Arg Ile Ile Glu Thr Ala Pro Thr Asp Tyr Leu Ser Trp Gly
            100                 105                 110

Val Gly Ala Val Gly Asn Pro Arg Phe Ile Asn Val Glu Ile Val His
            115                 120                 125

Thr His Asp Tyr Ala Ser Phe Ala Arg Ser Met Asn Asn Tyr Ala Asp
    130                 135                 140

Tyr Ala Ala Thr Gln Leu Gln Tyr Tyr Gly Leu Lys Pro Asp Ser Ala
145                 150                 155                 160

Glu Tyr Asp Gly Asn Gly Thr Val Trp Thr His Tyr Ala Val Ser Lys
                165                 170                 175

Tyr Leu Gly Gly Thr Asp His Ala Asp Pro His Gly Tyr Leu Arg Ser
            180                 185                 190

His Asn Tyr Ser Tyr Asp Gln Leu Tyr Asp Leu Ile Asn Glu Lys Tyr
            195                 200                 205

Leu Ile Lys Met Gly Lys Val Ala Pro Trp Gly Thr Gln Ser Thr Thr
```

```
            210                 215                 220
Thr Pro Thr Thr Pro Ser Lys Pro Ser Thr Pro Ser Lys Pro Ser Thr
225                 230                 235                 240

Pro Ser Thr Gly Lys Leu Thr Val Ala Ala Asn Asn Gly Val Ala Gln
                245                 250                 255

Ile Lys Pro Thr Asn Ser Gly Leu Tyr Thr Thr Val Tyr Asp Lys Thr
                260                 265                 270

Gly Lys Ala Thr Asn Glu Val Gln Lys Thr Phe Ala Val Ser Lys Thr
            275                 280                 285

Ala Thr Leu Gly Asn Gln Lys Phe Tyr Leu Val Gln Asp Tyr Asn Ser
290                 295                 300

Gly Asn Lys Phe Gly Trp Val Lys Glu Gly Asp Val Val Tyr Asn Thr
305                 310                 315                 320

Ala Lys Ser Pro Val Asn Val Asn Gln Ser Tyr Ser Ile Lys Pro Gly
                325                 330                 335

Thr Lys Leu Tyr Thr Val Pro Trp Gly Thr Ser Lys Gln Val Ala Gly
                340                 345                 350

Ser Val Ser Gly Ser Gly Asn Gln Thr Phe Lys Ala Ser Lys Gln Gln
            355                 360                 365

Gln Ile Asp Lys Ser Ile Tyr Leu Tyr Gly Ser Val Asn Gly Lys Ser
370                 375                 380

Gly Trp Val Ser Lys Ala Tyr Leu Val Asp Thr Ala Lys Pro Thr Pro
385                 390                 395                 400

Thr Pro Thr Pro Lys Pro Ser Thr Pro Thr Thr Asn Asn Lys Leu Thr
                405                 410                 415

Val Ser Ser Leu Asn Gly Val Ala Gln Ile Asn Ala Lys Asn Asn Gly
            420                 425                 430

Leu Phe Thr Thr Val Tyr Asp Lys Thr Gly Lys Pro Thr Lys Glu Val
                435                 440                 445

Gln Lys Thr Phe Ala Val Thr Lys Glu Ala Ser Leu Gly Gly Asn Lys
450                 455                 460

Phe Tyr Leu Val Lys Asp Tyr Asn Ser Pro Thr Leu Ile Gly Trp Val
465                 470                 475                 480

Lys Gln Gly Asp Val Ile Tyr Asn Asn Ala Lys Ser Pro Val Asn Val
            485                 490                 495

Met Gln Thr Tyr Thr Val Lys Pro Gly Thr Lys Leu Tyr Ser Val Pro
                500                 505                 510

Trp Gly Thr Tyr Lys Gln Glu Ala Gly Ala Val Ser Gly Thr Gly Asn
                515                 520                 525

Gln Thr Phe Lys Ala Thr Lys Gln Gln Gln Ile Asp Lys Ser Ile Tyr
            530                 535                 540

Leu Tyr Gly Thr Val Asn Gly Lys Ser Gly Trp Ile Ser Lys Ala Tyr
545                 550                 555                 560

Leu Ala Val Pro Ala Ala Pro Lys Lys Ala Val Ala Gln Pro Lys Thr
                565                 570                 575

Ala Val Lys Ala
            580

<210> SEQ ID NO 77
<211> LENGTH: 480
<212> TYPE: PRT
<213> ORGANISM: staphylococcus aureus

<400> SEQUENCE: 77
```

-continued

```
Tyr Ala Val Thr Lys Pro Gln Thr Thr Gln Thr Val Ser Lys Ile Ala
 1               5                  10                  15
Gln Val Lys Pro Asn Asn Thr Gly Ile Arg Ala Ser Val Tyr Glu Lys
            20                  25                  30
Thr Ala Lys Asn Gly Ala Lys Tyr Ala Asp Arg Thr Phe Tyr Val Thr
        35                  40                  45
Lys Glu Arg Ala His Gly Asn Glu Thr Tyr Val Leu Leu Asn Asn Thr
    50                  55                  60
Ser His Asn Ile Pro Leu Gly Trp Phe Asn Val Lys Asp Leu Asn Val
65                  70                  75                  80
Gln Asn Leu Gly Lys Glu Val Lys Thr Thr Gln Lys Tyr Thr Val Asn
                85                  90                  95
Arg Ser Asn Asn Gly Leu Ser Met Val Pro Trp Gly Thr Lys Asn Gln
            100                 105                 110
Val Ile Leu Thr Gly Asn Asn Ile Ala Gln Gly Thr Phe Asn Ala Thr
        115                 120                 125
Lys Gln Val Ser Val Gly Lys Asp Val Tyr Leu Tyr Gly Thr Ile Asn
    130                 135                 140
Asn Arg Thr Gly Trp Val Asn Ser Lys Asp Leu Thr Ala Pro Thr Ala
145                 150                 155                 160
Val Lys Pro Thr Thr Ser Ala Ala Lys Asp Tyr Asn Tyr Thr Tyr Val
                165                 170                 175
Ile Lys Asn Gly Asn Gly Tyr Tyr Val Thr Pro Asn Ser Asp Thr
            180                 185                 190
Ala Lys Tyr Ser Leu Lys Ala Phe Asn Glu Gln Pro Phe Ala Val Val
        195                 200                 205
Lys Glu Gln Val Ile Asn Gly Gln Thr Trp Tyr Tyr Gly Lys Leu Ser
    210                 215                 220
Asn Gly Lys Leu Ala Trp Ile Lys Ser Thr Asp Leu Ala Lys Glu Leu
225                 230                 235                 240
Ile Lys Tyr Asn Gln Ile Gly Met Thr Leu Asn Gln Val Ala Gln Ile
                245                 250                 255
Gln Ala Gly Leu Gln Tyr Lys Pro Gln Val Gln Arg Val Pro Gly Lys
            260                 265                 270
Trp Thr Asp Ala Asn Phe Asn Asp Val Lys His Ala Met Asp Thr Lys
        275                 280                 285
Arg Leu Ala Gln Asp Pro Ala Leu Lys Tyr Gln Phe Leu Arg Leu Asp
    290                 295                 300
Gln Pro Gln Asn Ile Ser Ile Asp Lys Ile Asn Gln Phe Leu Lys Gly
305                 310                 315                 320
Lys Gly Val Leu Glu Asn Gln Gly Ala Ala Phe Asn Lys Ala Ala Gln
                325                 330                 335
Met Tyr Gly Ile Asn Glu Val Tyr Leu Ile Ser His Ala Leu Leu Glu
            340                 345                 350
Thr Gly Asn Gly Thr Ser Gln Leu Ala Lys Gly Ala Asp Val Val Asn
        355                 360                 365
Asn Lys Val Val Thr Asn Ser Asn Thr Lys Tyr His Asn Val Phe Gly
    370                 375                 380
Ile Ala Ala Tyr Asp Asn Asp Pro Leu Arg Glu Gly Ile Lys Tyr Ala
385                 390                 395                 400
Lys Gln Ala Gly Trp Asp Thr Val Ser Lys Ala Ile Val Gly Gly Ala
                405                 410                 415
Lys Phe Ile Gly Asn Ser Tyr Val Lys Ala Gly Gln Asn Thr Leu Tyr
```

```
            420                 425                 430
Lys Met Arg Trp Asn Pro Ala His Pro Gly Thr His Gln Tyr Ala Thr
        435                 440                 445

Asp Val Asp Trp Ala Asn Ile Asn Ala Lys Ile Ile Lys Gly Tyr Tyr
    450                 455                 460

Asp Lys Ile Gly Glu Val Gly Lys Tyr Phe Asp Ile Pro Gln Tyr Lys
465                 470                 475                 480

<210> SEQ ID NO 78
<211> LENGTH: 600
<212> TYPE: PRT
<213> ORGANISM: Artificial
<220> FEATURE:
<223> OTHER INFORMATION: His-labeled, N-acetylmuramoyl-L-alanine
      amidase from Staphylococcus aureus with BirA biotinylation site

<400> SEQUENCE: 78

Met His His His His His Ser Ala Ser Ala Gln Pro Arg Ser Val
1               5                   10                  15

Ala Ala Thr Pro Lys Thr Ser Leu Pro Lys Tyr Lys Pro Gln Val Asn
                20                  25                  30

Ser Ser Ile Asn Asp Tyr Ile Arg Lys Asn Asn Leu Lys Ala Pro Lys
            35                  40                  45

Ile Glu Glu Asp Tyr Thr Ser Tyr Phe Pro Lys Tyr Ala Tyr Arg Asn
50                  55                  60

Gly Val Gly Arg Pro Glu Gly Ile Val Val His Asp Thr Ala Asn Asp
65                  70                  75                  80

Arg Ser Thr Ile Asn Gly Glu Ile Ser Tyr Met Lys Asn Asn Tyr Gln
                85                  90                  95

Asn Ala Phe Val His Ala Phe Val Asp Gly Asp Arg Ile Ile Glu Thr
            100                 105                 110

Ala Pro Thr Asp Tyr Leu Ser Trp Gly Val Gly Ala Val Gly Asn Pro
        115                 120                 125

Arg Phe Ile Asn Val Glu Ile Val His Thr His Asp Tyr Ala Ser Phe
130                 135                 140

Ala Arg Ser Met Asn Asn Tyr Ala Asp Tyr Ala Ala Thr Gln Leu Gln
145                 150                 155                 160

Tyr Tyr Gly Leu Lys Pro Asp Ser Ala Glu Tyr Asp Gly Asn Gly Thr
                165                 170                 175

Val Trp Thr His Tyr Ala Val Ser Lys Tyr Leu Gly Gly Thr Asp His
            180                 185                 190

Ala Asp Pro His Gly Tyr Leu Arg Ser His Asn Tyr Ser Tyr Asp Gln
        195                 200                 205

Leu Tyr Asp Leu Ile Asn Glu Lys Tyr Leu Ile Lys Met Gly Lys Val
    210                 215                 220

Ala Pro Trp Gly Thr Gln Ser Thr Thr Thr Pro Thr Thr Pro Ser Lys
225                 230                 235                 240

Pro Thr Thr Pro Ser Lys Pro Ser Thr Gly Lys Leu Thr Val Ala Ala
                245                 250                 255

Asn Asn Gly Val Ala Gln Ile Lys Pro Thr Asn Ser Gly Leu Tyr Thr
            260                 265                 270

Thr Val Tyr Asp Lys Thr Gly Lys Ala Thr Asn Glu Val Gln Lys Thr
        275                 280                 285

Phe Ala Val Ser Lys Thr Ala Thr Leu Gly Asn Gln Lys Phe Tyr Leu
    290                 295                 300
```

```
Val Gln Asp Tyr Asn Ser Gly Asn Lys Phe Gly Trp Val Lys Glu Gly
305                 310                 315                 320

Asp Val Val Tyr Asn Thr Ala Lys Ser Pro Val Asn Val Asn Gln Ser
            325                 330                 335

Tyr Ser Ile Lys Pro Gly Thr Lys Leu Tyr Thr Val Pro Trp Gly Thr
            340                 345                 350

Ser Lys Gln Val Ala Gly Ser Val Gly Ser Gly Asn Gln Thr Phe
            355                 360                 365

Lys Ala Ser Lys Gln Gln Gln Ile Asp Lys Ser Ile Tyr Leu Tyr Gly
            370                 375                 380

Ser Val Asn Gly Lys Ser Gly Trp Val Ser Lys Ala Tyr Leu Val Asp
385                 390                 395                 400

Thr Ala Lys Pro Thr Pro Thr Pro Thr Pro Lys Pro Ser Thr Pro Thr
            405                 410                 415

Thr Asn Asn Lys Leu Thr Val Ser Ser Leu Asn Gly Val Ala Gln Ile
            420                 425                 430

Asn Ala Lys Asn Asn Gly Leu Phe Thr Thr Val Tyr Asp Lys Thr Gly
            435                 440                 445

Lys Pro Thr Lys Glu Val Gln Lys Thr Phe Ala Val Thr Lys Glu Ala
            450                 455                 460

Ser Leu Gly Gly Asn Lys Phe Tyr Leu Val Lys Asp Tyr Asn Ser Pro
465                 470                 475                 480

Thr Leu Ile Gly Trp Val Lys Gln Gly Asp Val Ile Tyr Asn Asn Ala
            485                 490                 495

Lys Ser Pro Val Asn Val Met Gln Thr Tyr Thr Val Lys Pro Gly Thr
            500                 505                 510

Lys Leu Tyr Ser Val Pro Trp Gly Thr Tyr Lys Gln Glu Ala Gly Ala
            515                 520                 525

Val Ser Gly Thr Gly Asn Gln Thr Phe Lys Ala Thr Lys Gln Gln Gln
530                 535                 540

Ile Asp Lys Ser Ile Tyr Leu Phe Gly Thr Val Asn Gly Lys Ser Gly
545                 550                 555                 560

Trp Val Ser Lys Ala Tyr Leu Ala Val Pro Ala Ala Pro Lys Lys Ala
            565                 570                 575

Val Ala Gln Pro Lys Thr Ala Val Lys Gly Leu Asn Asp Ile Phe Glu
            580                 585                 590

Ala Gln Lys Ile Glu Trp His Glu
            595                 600

<210> SEQ ID NO 79
<211> LENGTH: 503
<212> TYPE: PRT
<213> ORGANISM: Artificial
<220> FEATURE:
<223> OTHER INFORMATION: His-labeled, glucosaminidase from
      Staphylococcus aureus with BirA biotinylation site

<400> SEQUENCE: 79

Met Gly His His His His His His Ala Tyr Thr Val Thr Lys Pro Gln
1               5                   10                  15

Thr Thr Gln Thr Val Ser Lys Ile Ala Gln Val Lys Pro Asn Asn Thr
            20                  25                  30

Gly Ile Arg Ala Ser Val Tyr Glu Lys Thr Ala Lys Asn Gly Ala Lys
        35                  40                  45

Tyr Ala Asp Arg Thr Phe Tyr Val Thr Lys Glu Arg Ala His Gly Asn
    50                  55                  60
```

-continued

Glu Thr Tyr Val Leu Leu Asn Asn Thr Ser His Asn Ile Pro Leu Gly
65                  70                  75                  80

Trp Phe Asn Val Lys Asp Leu Asn Val Gln Asn Leu Gly Lys Glu Val
                85                  90                  95

Lys Thr Thr Gln Lys Tyr Thr Val Asn Lys Ser Asn Asn Gly Leu Ser
            100                 105                 110

Met Val Pro Trp Gly Thr Lys Asn Gln Val Ile Leu Thr Gly Asn Asn
        115                 120                 125

Ile Ala Gln Gly Thr Phe Asn Ala Thr Lys Gln Val Ser Val Gly Lys
130                 135                 140

Asp Val Tyr Leu Tyr Gly Thr Ile Asn Asn Arg Thr Gly Trp Val Asn
145                 150                 155                 160

Ala Lys Asp Leu Thr Ala Pro Thr Ala Val Lys Pro Thr Thr Ser Ala
                165                 170                 175

Ala Lys Asp Tyr Asn Tyr Thr Tyr Val Ile Lys Asn Gly Asn Gly Tyr
            180                 185                 190

Tyr Tyr Val Thr Pro Asn Ser Asp Thr Ala Lys Tyr Ser Leu Lys Ala
        195                 200                 205

Phe Asn Glu Gln Pro Phe Ala Val Val Lys Glu Gln Val Ile Asn Gly
210                 215                 220

Gln Thr Trp Tyr Tyr Gly Lys Leu Ser Asn Gly Lys Leu Ala Trp Ile
225                 230                 235                 240

Lys Ser Thr Asp Leu Ala Lys Glu Leu Ile Lys Tyr Asn Gln Thr Gly
                245                 250                 255

Met Thr Leu Asn Gln Val Ala Gln Ile Gln Ala Gly Leu Gln Tyr Lys
            260                 265                 270

Pro Gln Val Gln Arg Val Pro Gly Lys Trp Thr Asp Ala Asn Phe Asn
        275                 280                 285

Asp Val Lys His Ala Met Asp Thr Lys Arg Leu Ala Gln Asp Pro Ala
290                 295                 300

Leu Lys Tyr Gln Phe Leu Arg Leu Asp Gln Pro Gln Asn Ile Ser Ile
305                 310                 315                 320

Asp Lys Ile Asn Gln Phe Leu Lys Gly Lys Gly Val Leu Glu Asn Gln
                325                 330                 335

Gly Ala Ala Phe Asn Lys Ala Ala Gln Met Tyr Gly Ile Asn Glu Val
            340                 345                 350

Tyr Leu Ile Ser His Ala Leu Leu Glu Thr Gly Asn Gly Thr Ser Gln
        355                 360                 365

Leu Ala Lys Gly Ala Asp Val Val Asn Asn Lys Val Val Thr Asn Ser
370                 375                 380

Asn Thr Lys Tyr His Asn Val Phe Gly Ile Ala Ala Tyr Asp Asn Asp
385                 390                 395                 400

Pro Leu Arg Glu Gly Ile Lys Tyr Ala Lys Gln Ala Gly Trp Asp Thr
                405                 410                 415

Val Ser Lys Ala Ile Val Gly Gly Ala Lys Phe Ile Gly Asn Ser Tyr
            420                 425                 430

Val Lys Ala Gly Gln Asn Thr Leu Tyr Lys Met Arg Trp Asn Pro Ala
        435                 440                 445

His Pro Gly Thr His Gln Tyr Ala Thr Asp Val Asp Trp Ala Asn Ile
450                 455                 460

Asn Ala Lys Ile Ile Lys Gly Tyr Tyr Asp Lys Ile Gly Glu Val Gly
465                 470                 475                 480

-continued

```
Lys Tyr Phe Asp Ile Pro Gln Tyr Gly Leu Asn Asp Ile Phe Glu Ala
            485                 490                 495
Gln Lys Ile Glu Trp His Glu
        500
```